United States Patent [19]
Weyrauch et al.

[11] Patent Number: 5,314,825
[45] Date of Patent: May 24, 1994

[54] CHEMICAL ANALYZER

[75] Inventors: Bruce Weyrauch, Newman Lake; Norman Kelln; Thomas Tiffany, both of Spokane; Robin Olson, Veradale, all of Wash.

[73] Assignee: Schiapparelli Biosystems, Inc., Fairfield, N.J.

[21] Appl. No.: 916,466

[22] Filed: Jul. 16, 1992

[51] Int. Cl.⁵ ............................................ G01N 35/00
[52] U.S. Cl. ...................................... 436/43; 436/45; 436/48; 436/49; 422/63; 422/64; 422/67; 356/246
[58] Field of Search ............... 422/64, 67, 63; 436/43, 436/45, 48, 49; 356/246

[56] References Cited

U.S. PATENT DOCUMENTS

| | | | |
|---|---|---|---|
| Re. 31,150 | 2/1983 | Ginsberg et al. | 422/64 |
| 4,234,538 | 11/1980 | Ginsberg et al. | 422/64 |
| 4,322,216 | 3/1982 | Lillig et al. | 23/230 R |
| 4,344,768 | 8/1982 | Parker et al. | 23/230 R |
| 4,388,279 | 7/1982 | Orimo et al. | 422/64 |
| 4,406,547 | 9/1983 | Aihara | 356/414 |
| 4,451,433 | 5/1984 | Yamashita et al. | 422/63 |
| 4,612,289 | 9/1986 | Furuta et al. | 436/34 |
| 4,634,575 | 1/1987 | Kawakami et al. | 422/63 |
| 4,687,638 | 8/1987 | Benajam | 422/73 |
| 4,764,342 | 8/1988 | Kelln et al. | 422/72 |
| 4,774,055 | 9/1988 | Wakatake et al. | 422/64 |
| 4,844,887 | 7/1989 | Galle et al. | 422/65 |
| 4,919,887 | 4/1990 | Wakatake | 422/67 |
| 4,939,095 | 7/1990 | Yokotani | 436/47 |
| 4,961,906 | 10/1990 | Andersen et al. | 422/102 |
| 4,965,049 | 10/1990 | Lillig et al. | 422/68.1 |

FOREIGN PATENT DOCUMENTS

WO88704 1/1988 World Int. Prop. O.

Primary Examiner—James C. Housel
Assistant Examiner—N. Bhat
Attorney, Agent, or Firm—Wells, St. John, Roberts, Gregory & Matkin

[57] ABSTRACT

The automatic chemical analyzer includes a turntable adapted to hold a plurality of disposable cuvettes. An optical system adjacent to the turntable can perform analytical absorbance or fluorescence tests on the contents of each cuvette as they are rotated on the turntable. A sample/reagent tray is rotatably mounted about an axis parallel to the turntable axis. A common probe arm pivoted about a third parallel axis mounts a pipette that can be moved along an arcuate path intersecting a cuvette access station on the turntable and at least one container access station on the sample/reagent tray for transferring liquids as required by specific test procedures. A sample tube entry port is provided to support individual draw tubes that are manually delivered to the analyzer at a sample access station and to facilitate removal of samples by the pipette without exposing operating personnel to accidental contact with liquid materials in the draw tube.

43 Claims, 53 Drawing Sheets

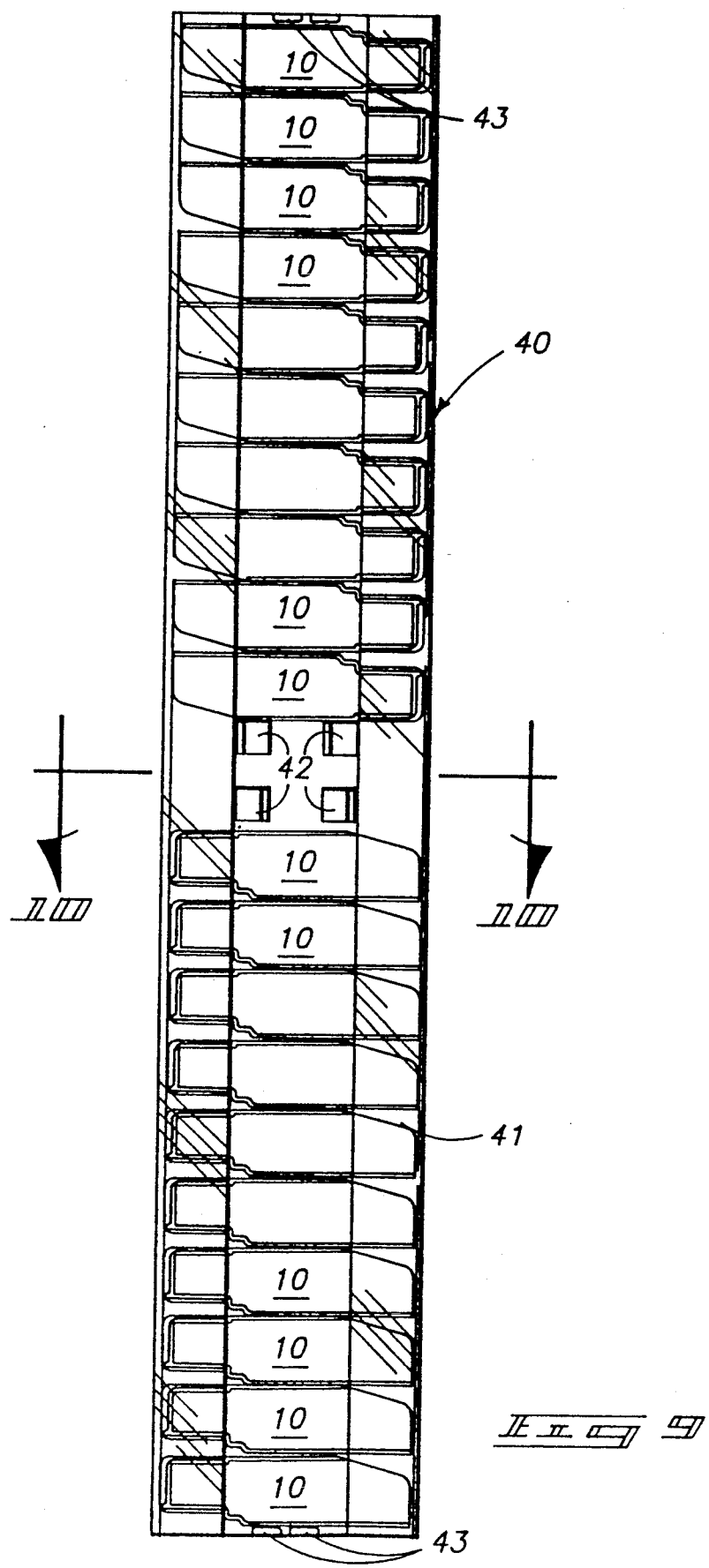

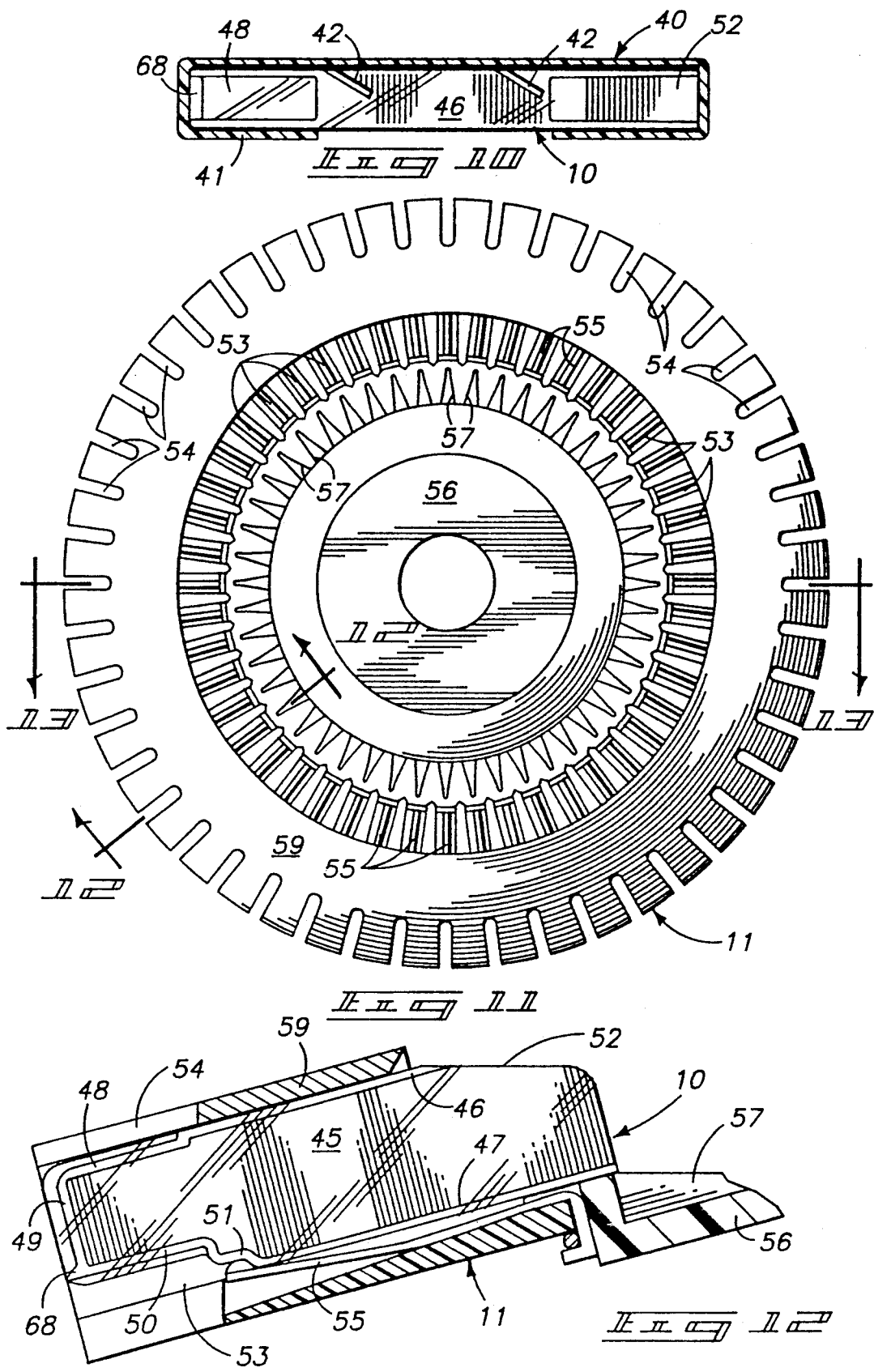

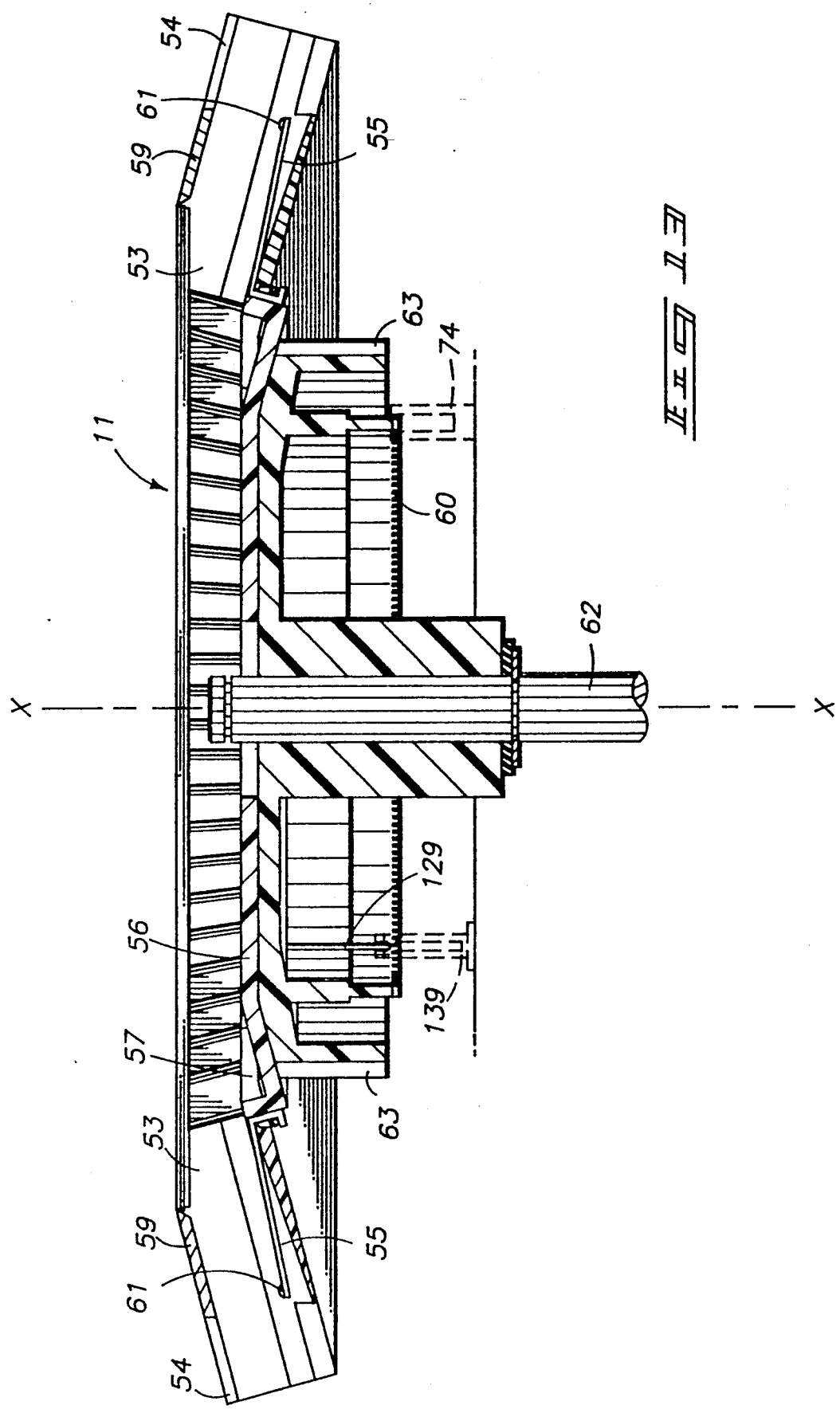

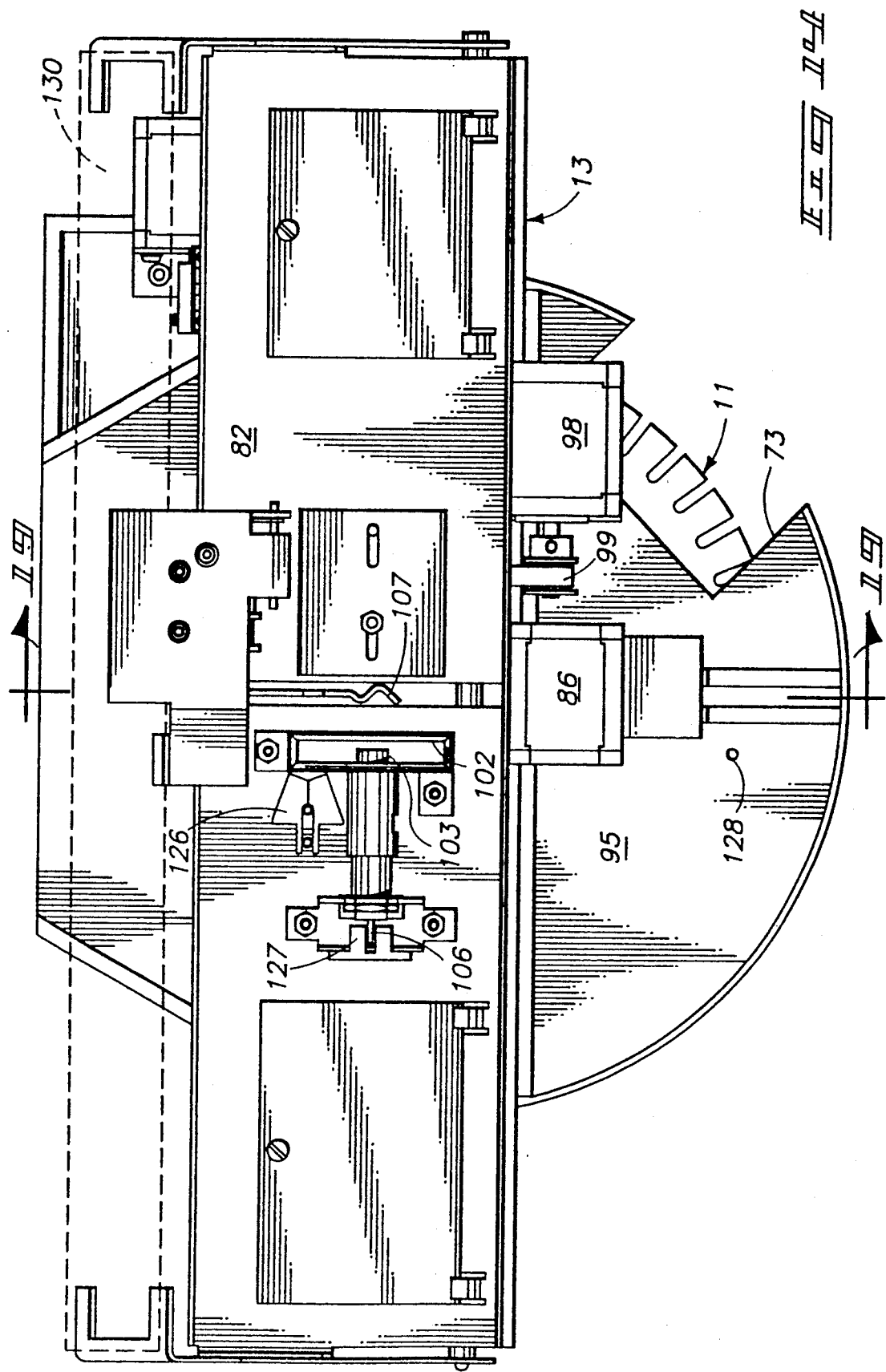

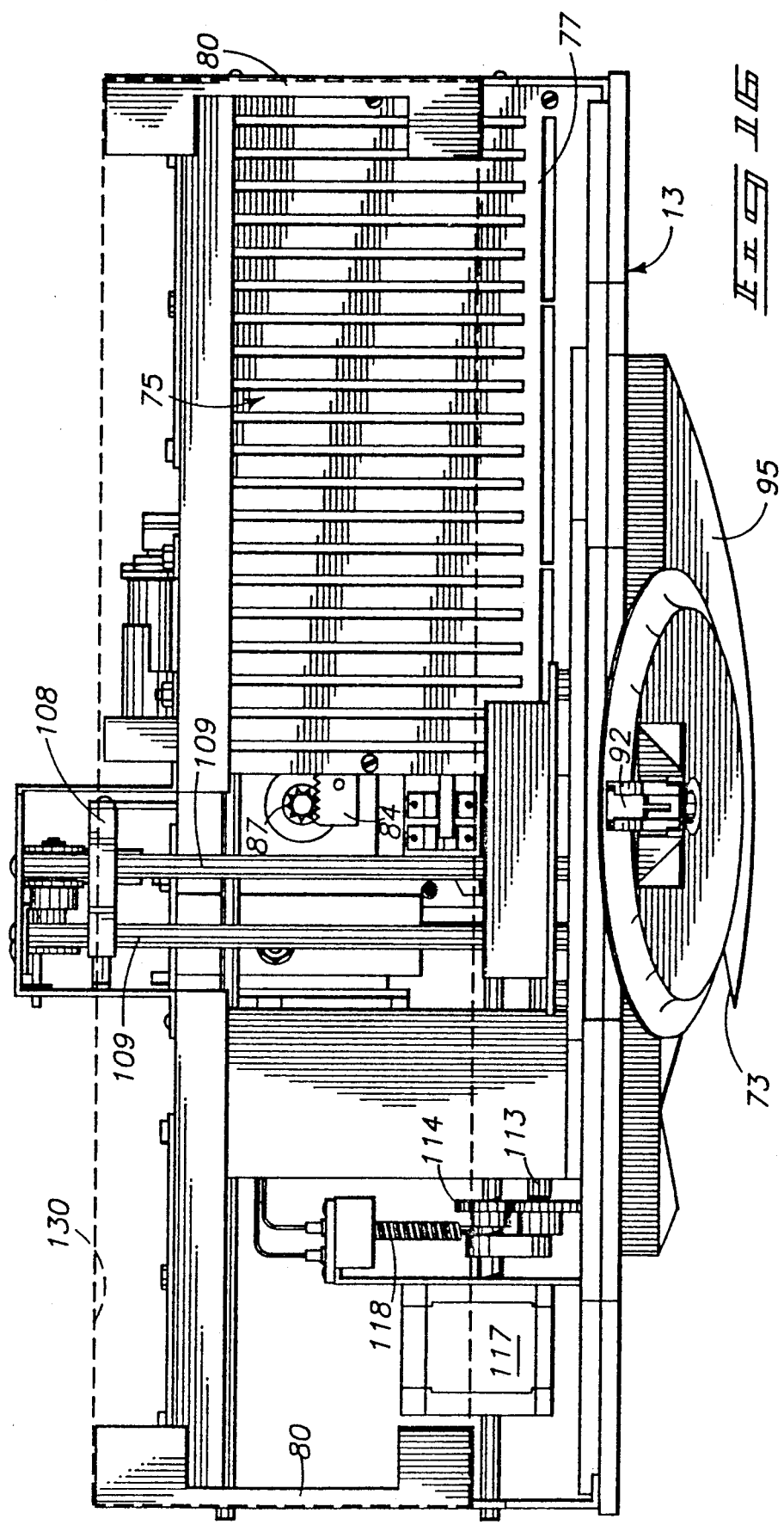

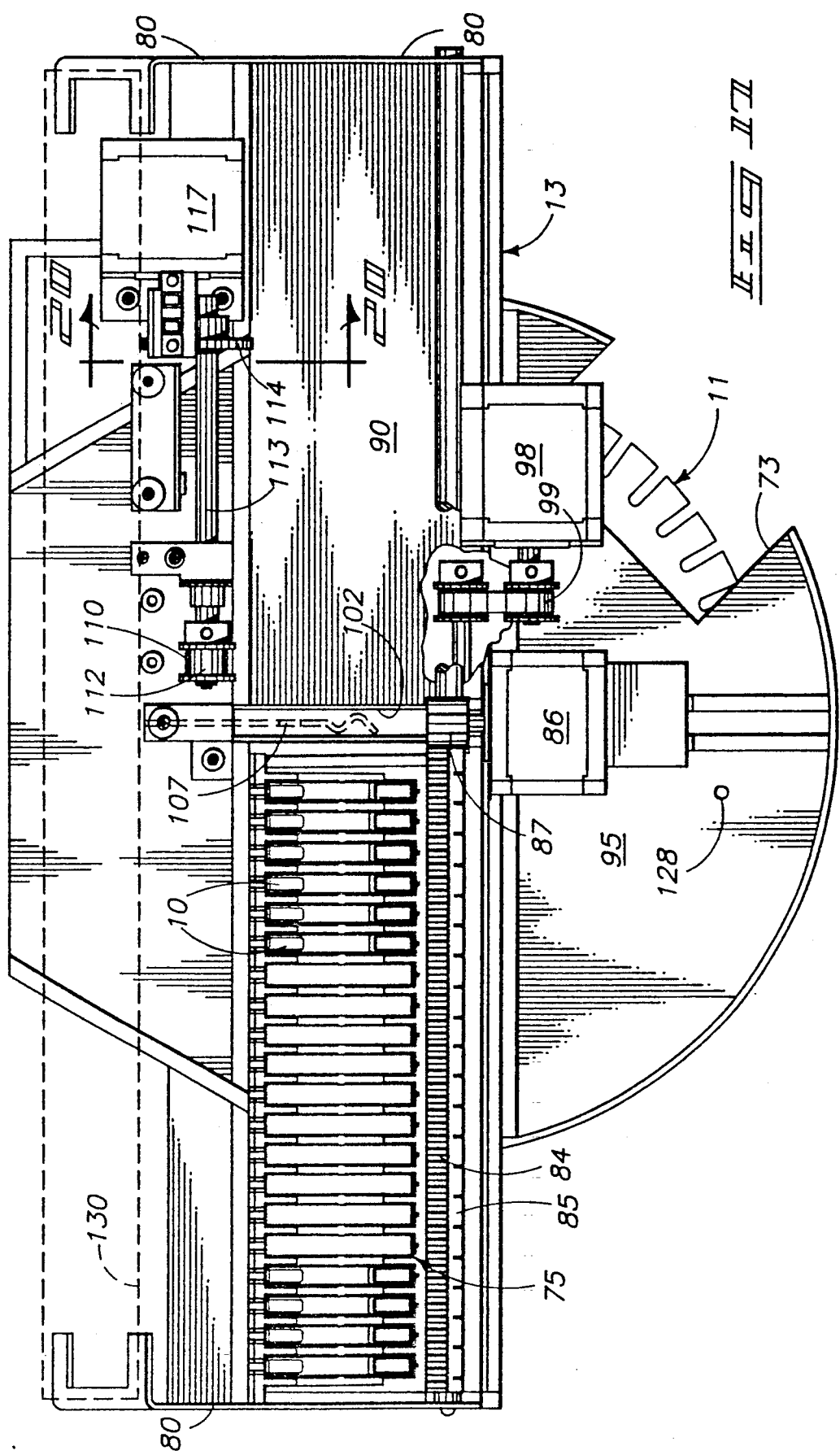

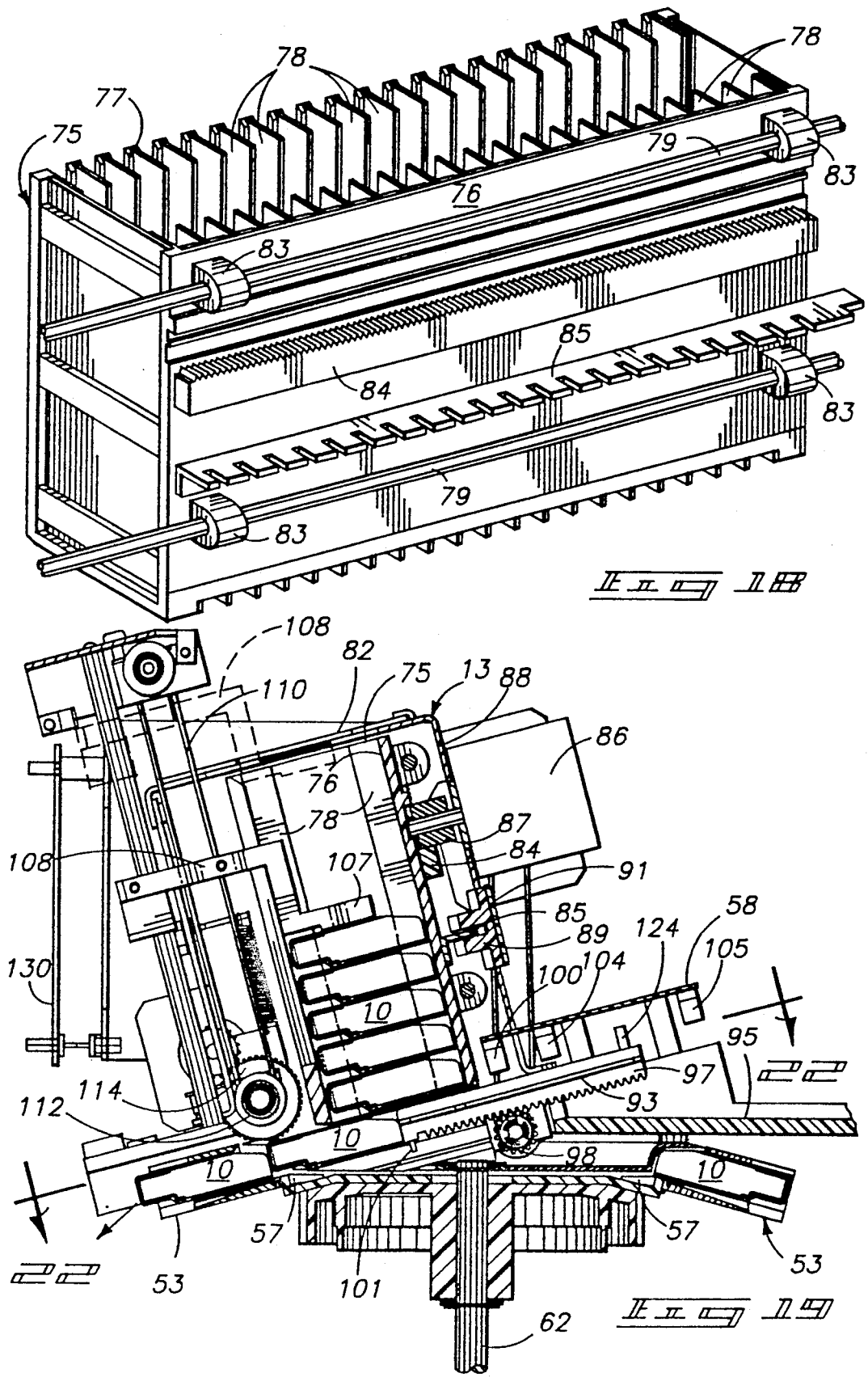

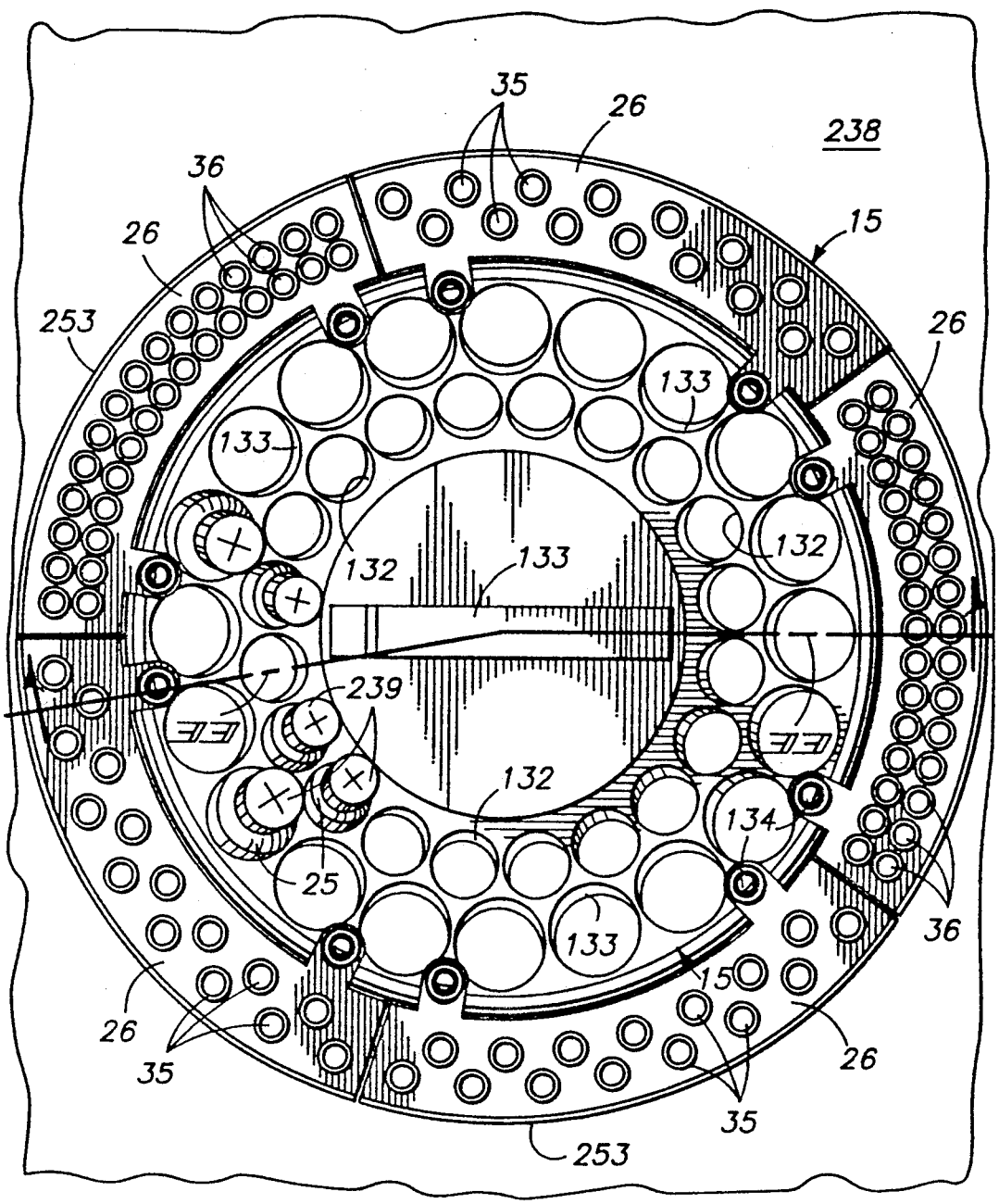

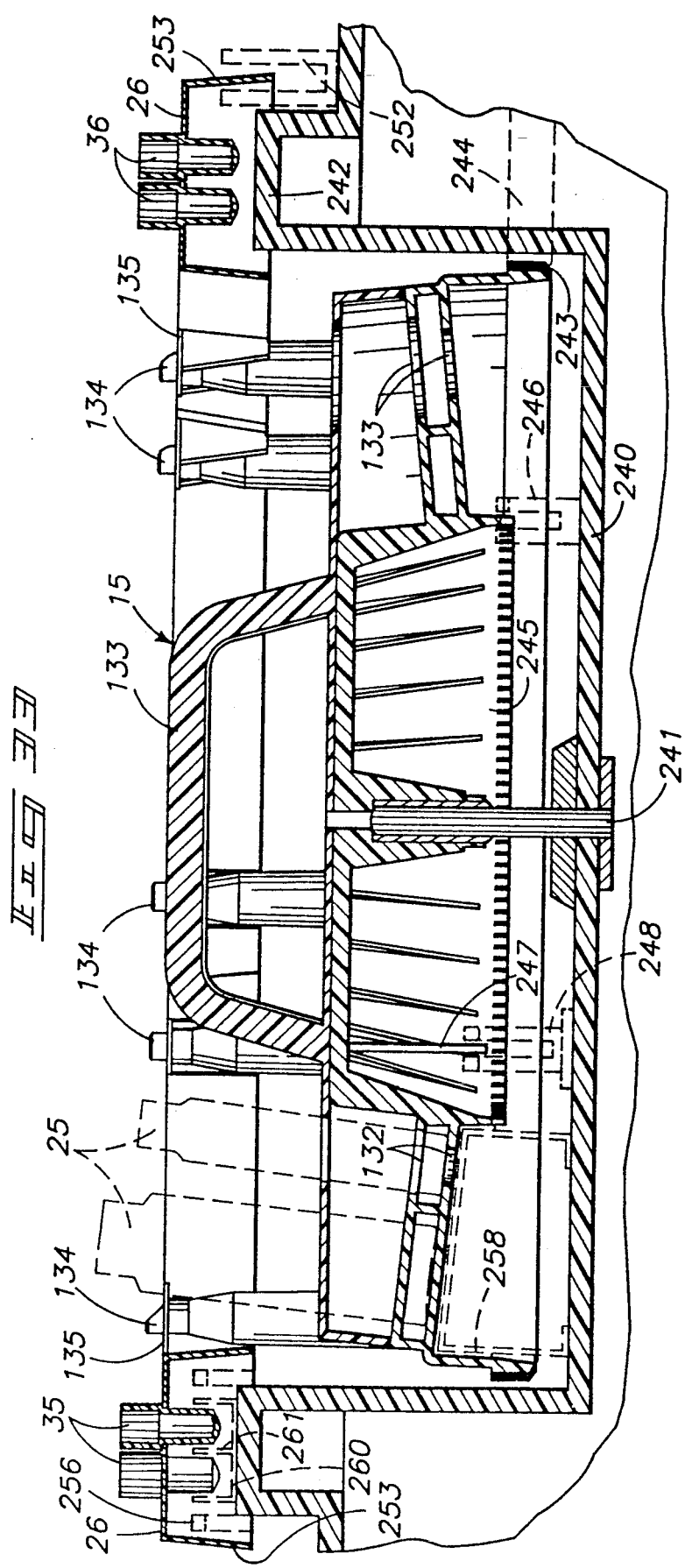

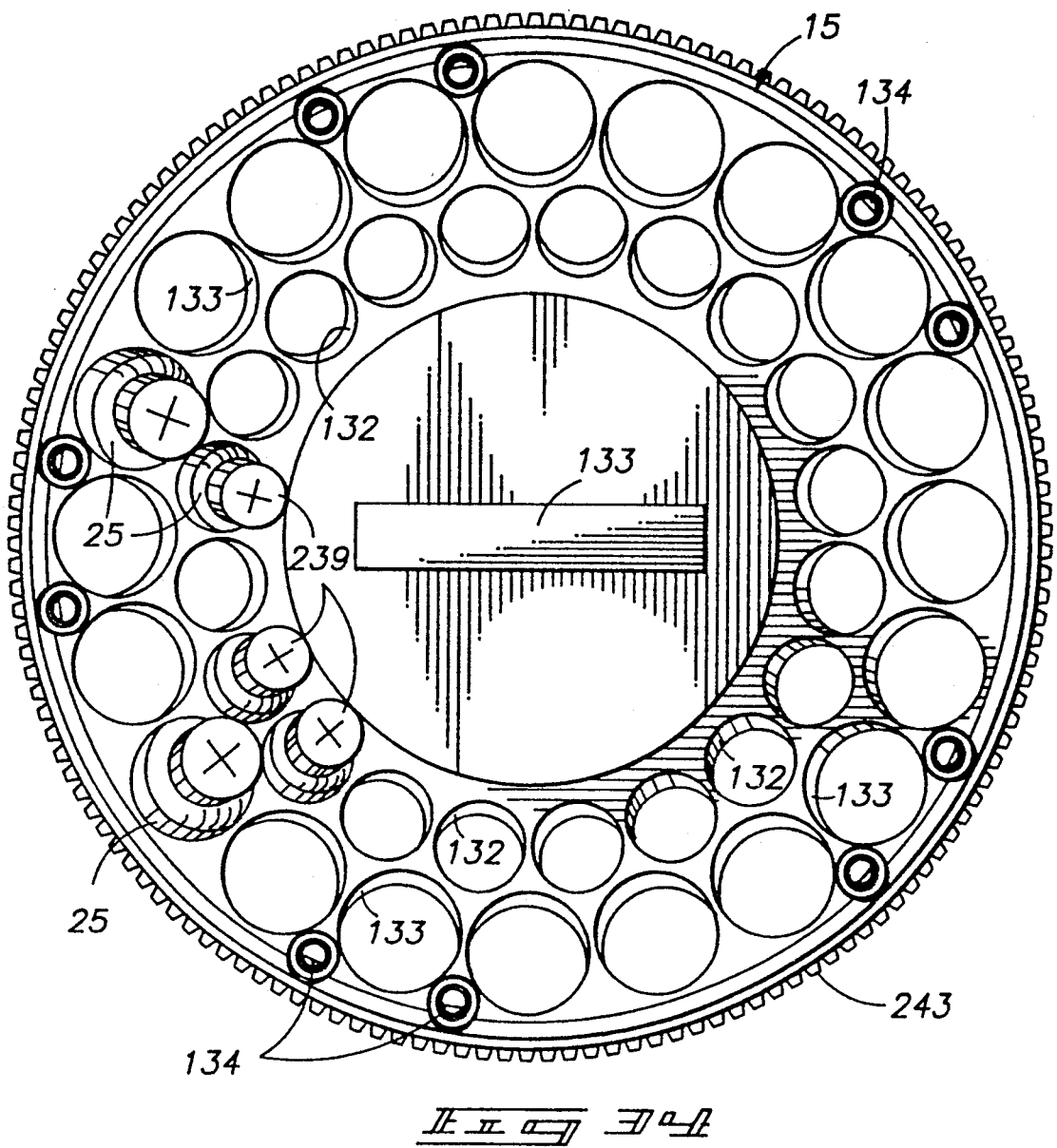
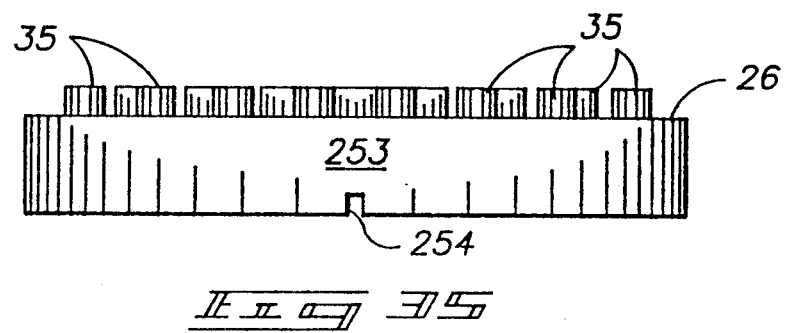

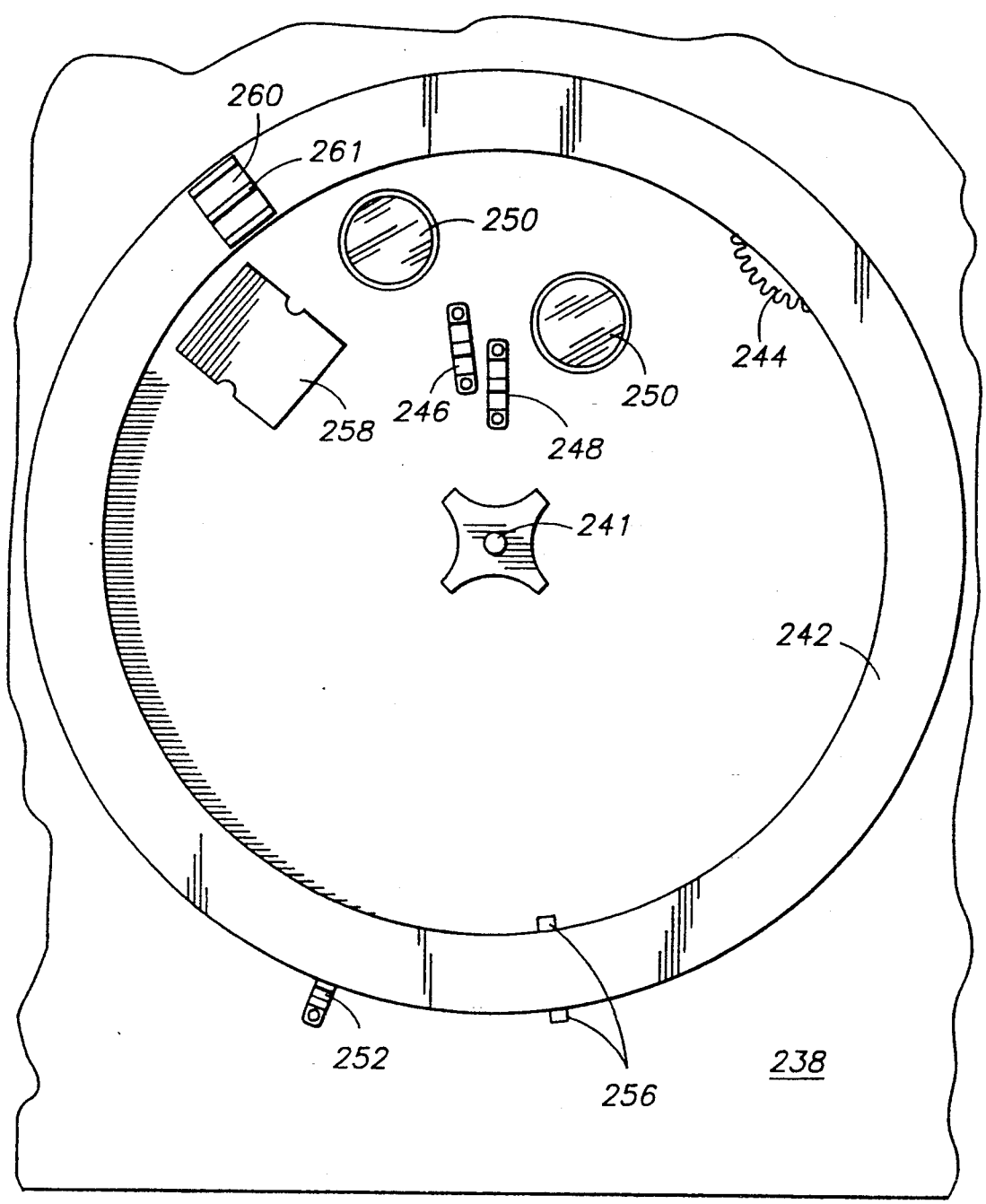

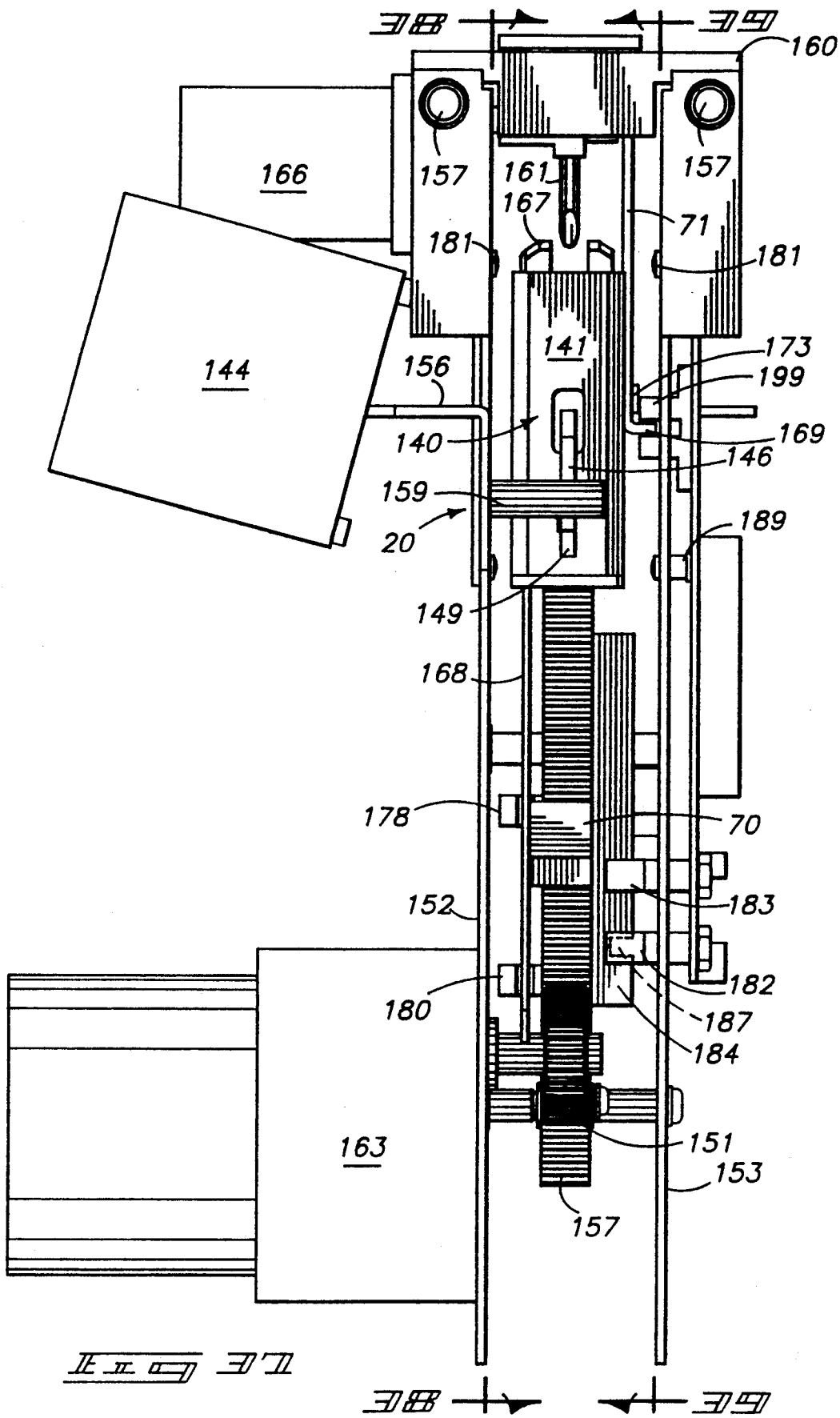

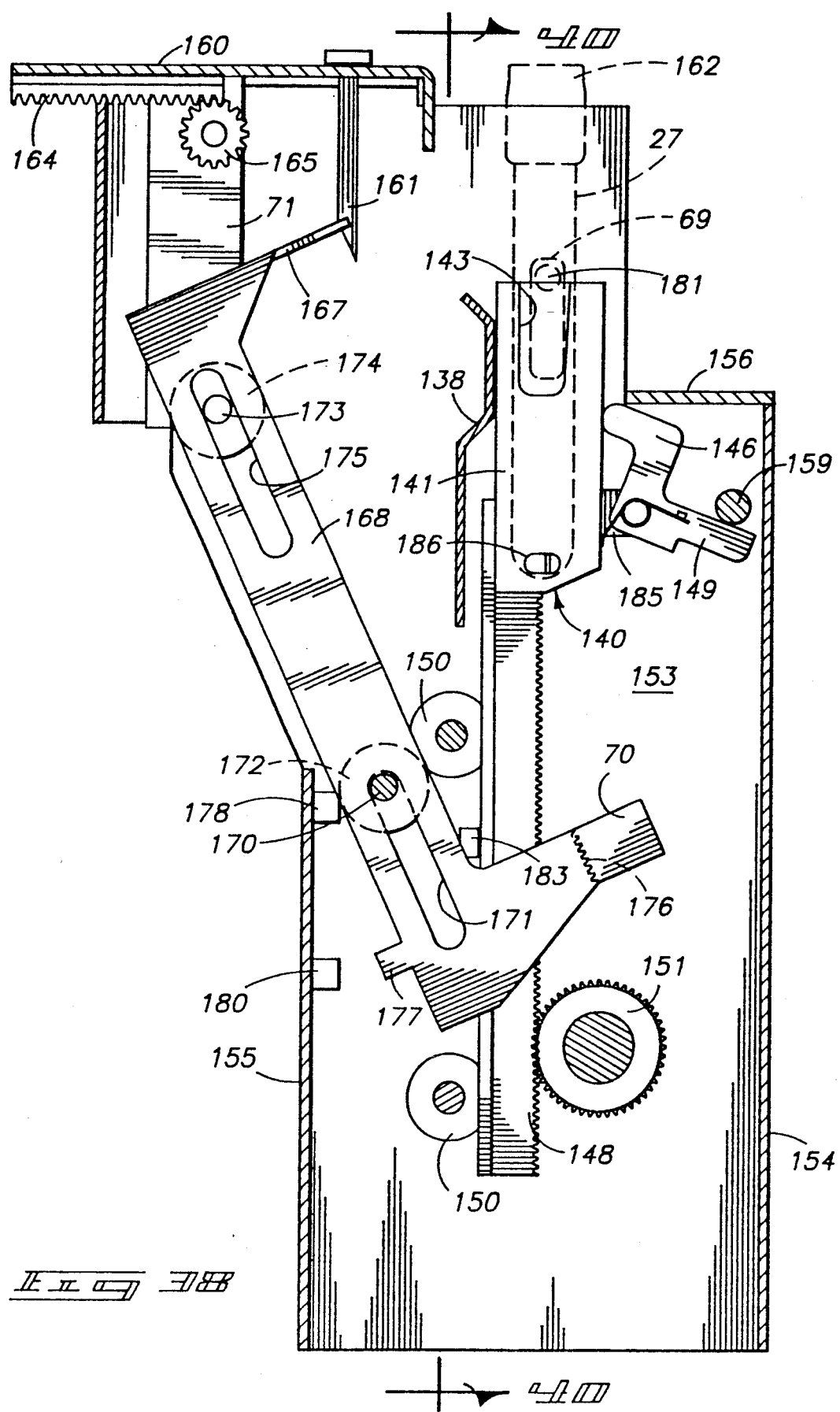

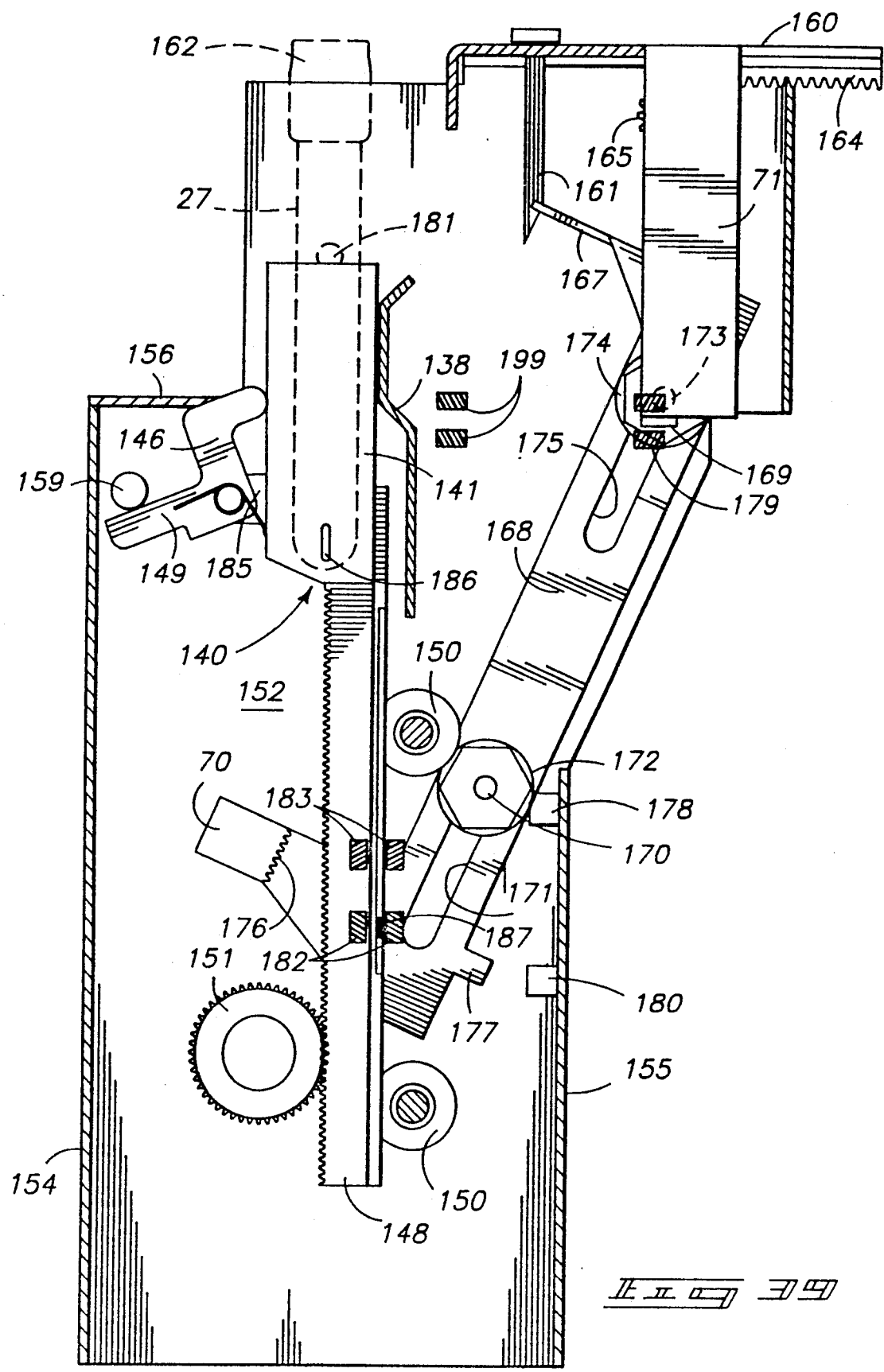

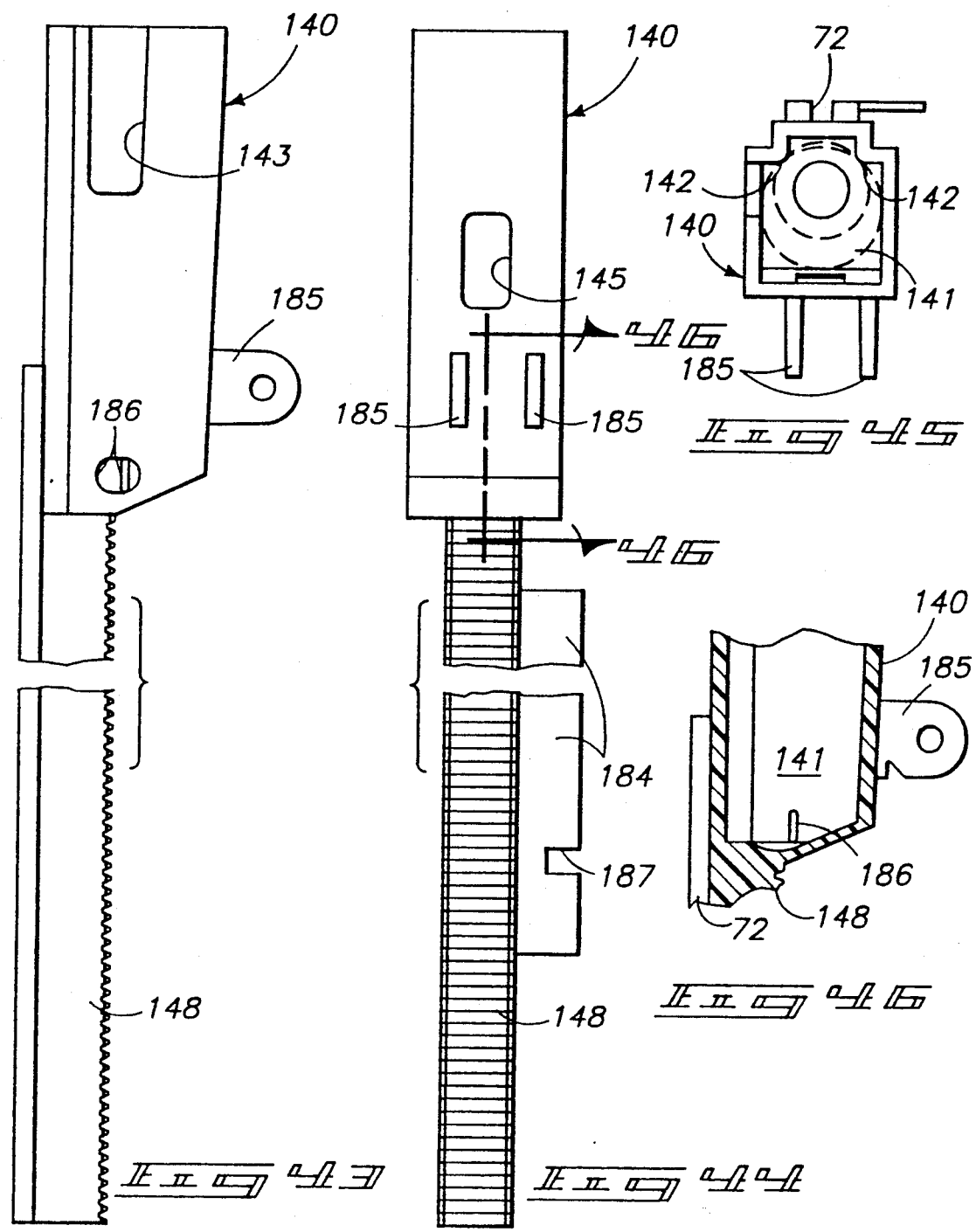

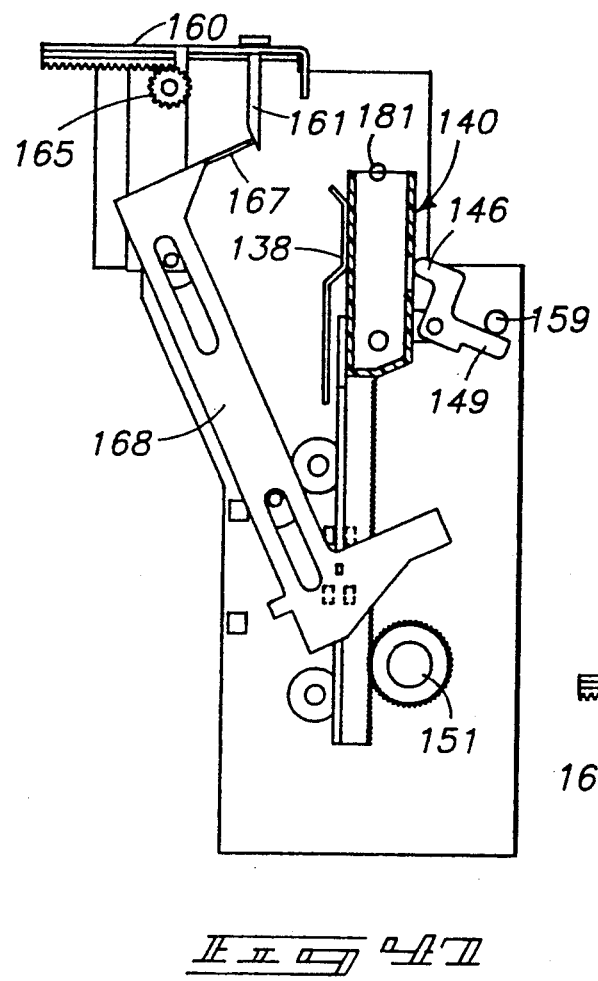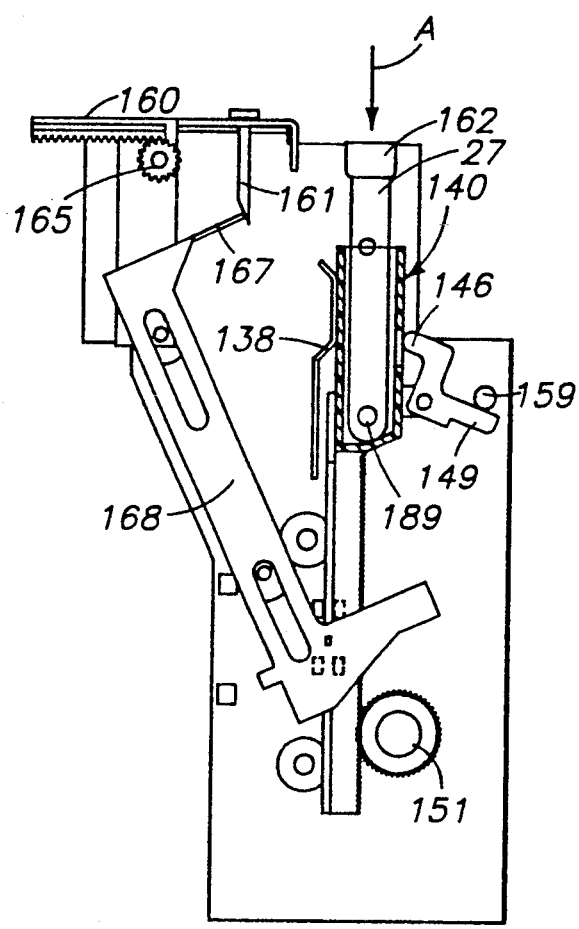

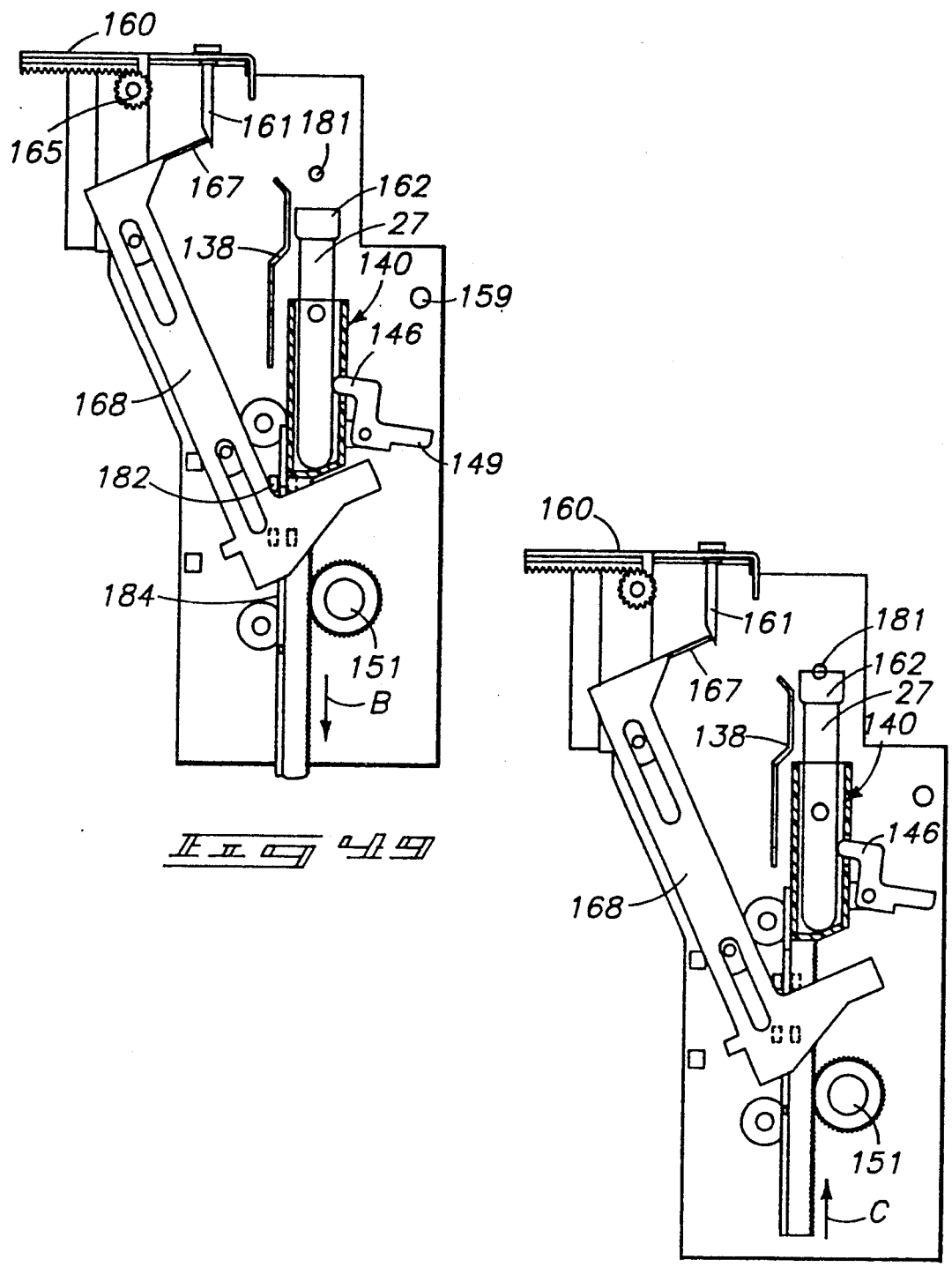

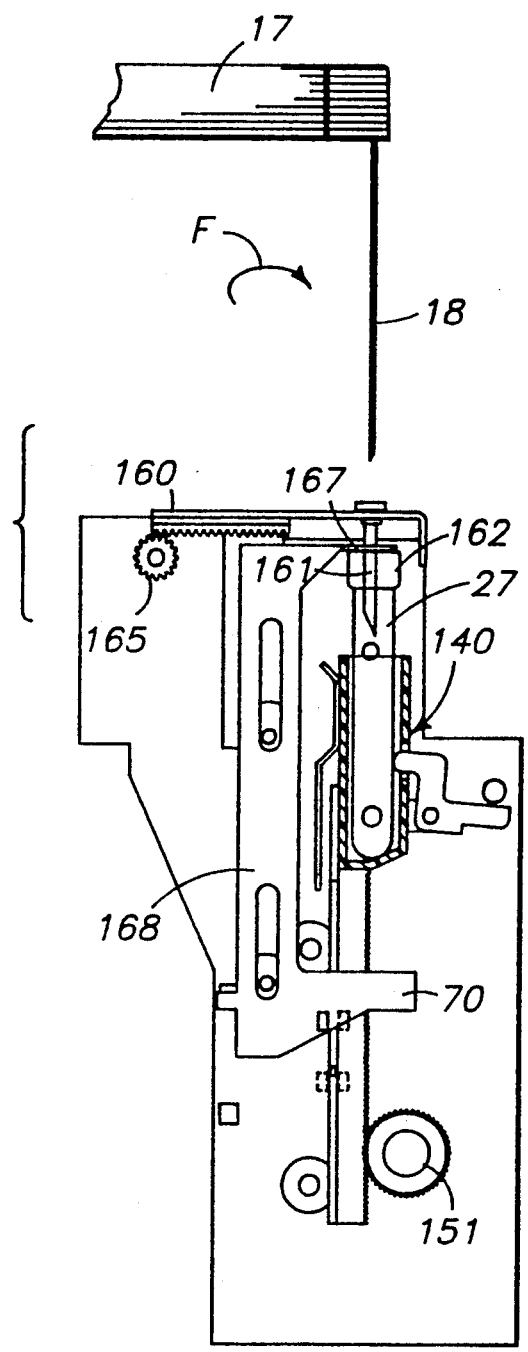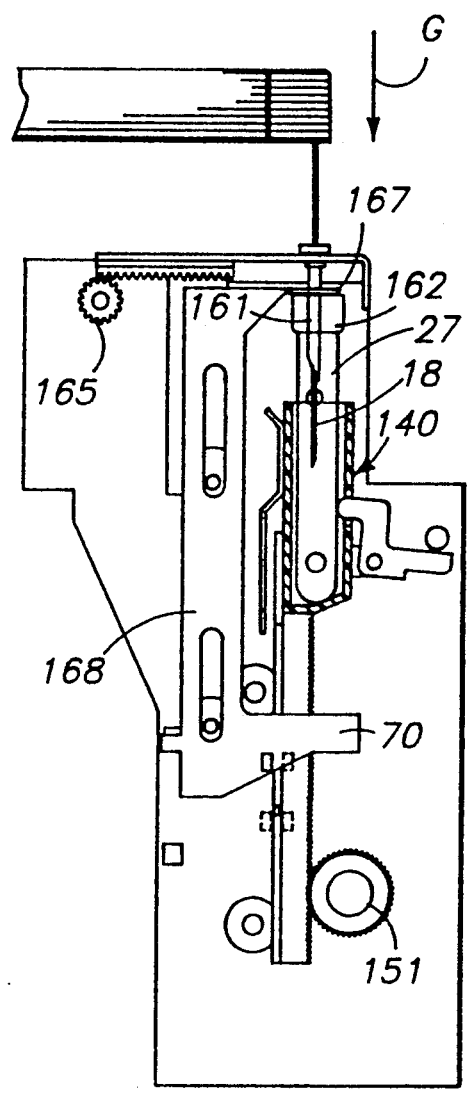
Fig 53
Fig 54

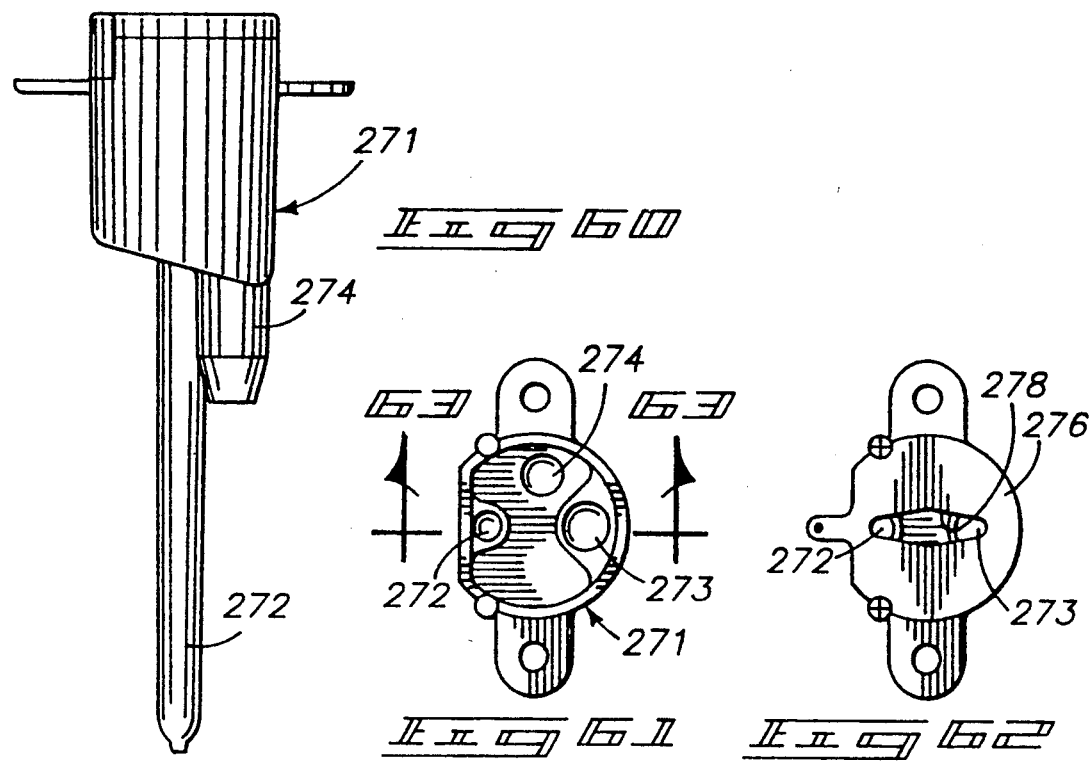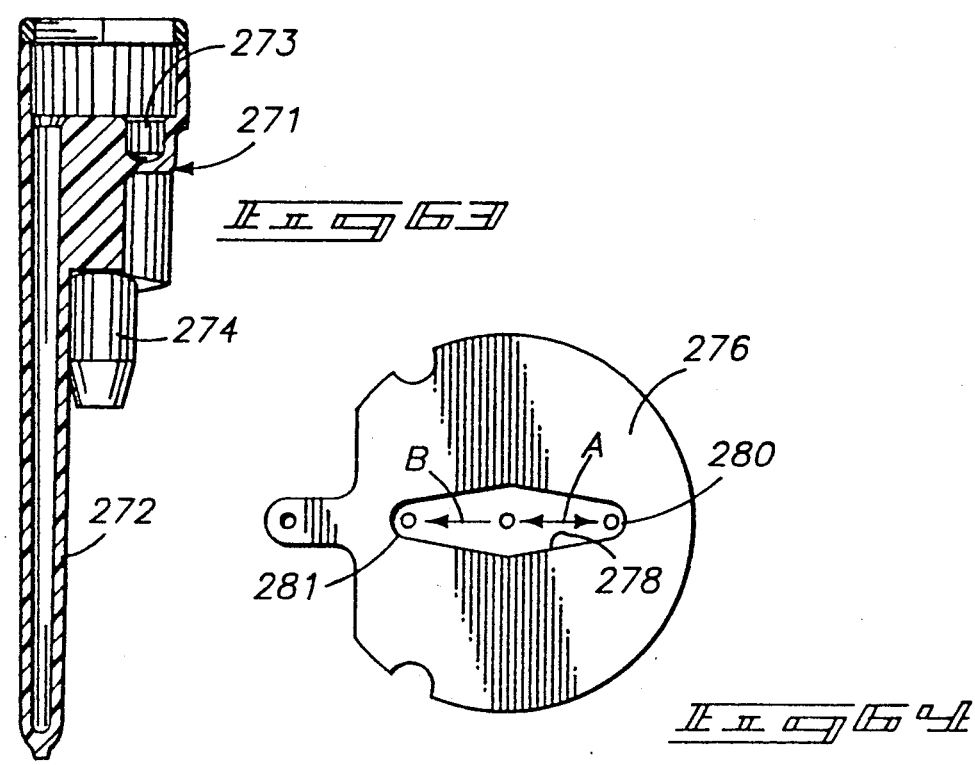

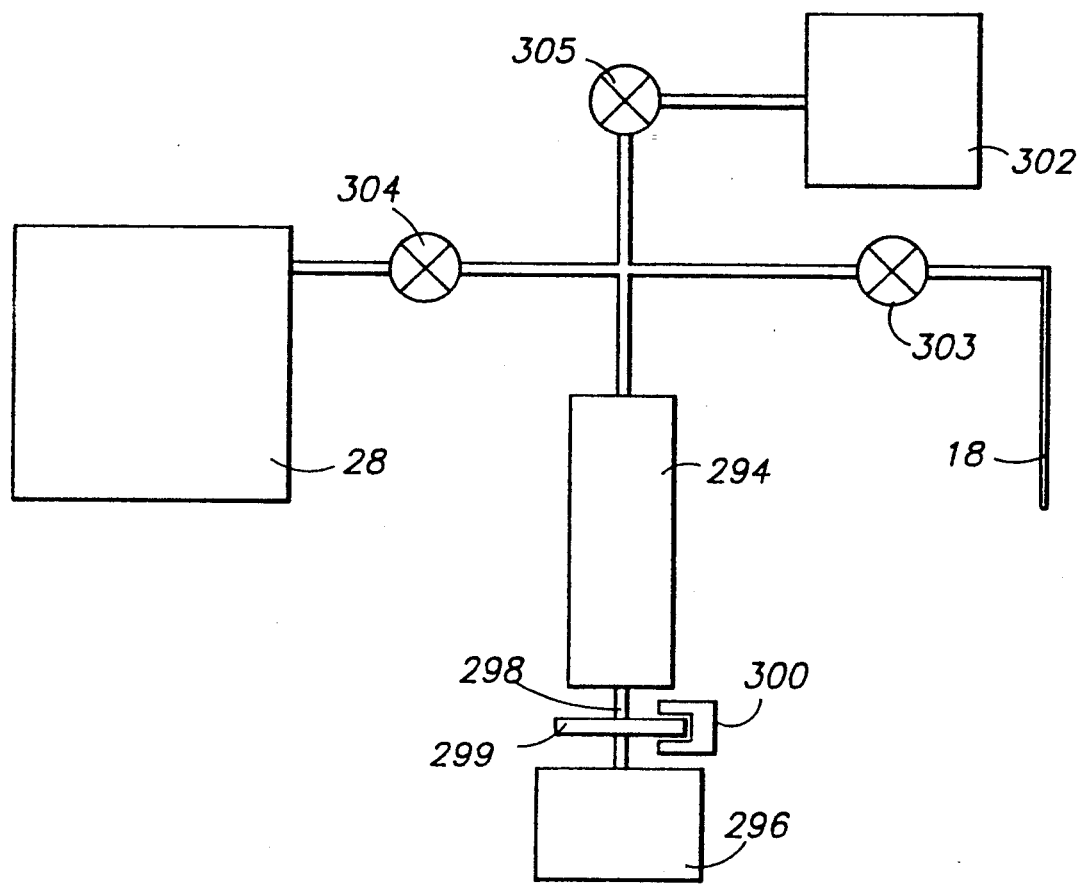

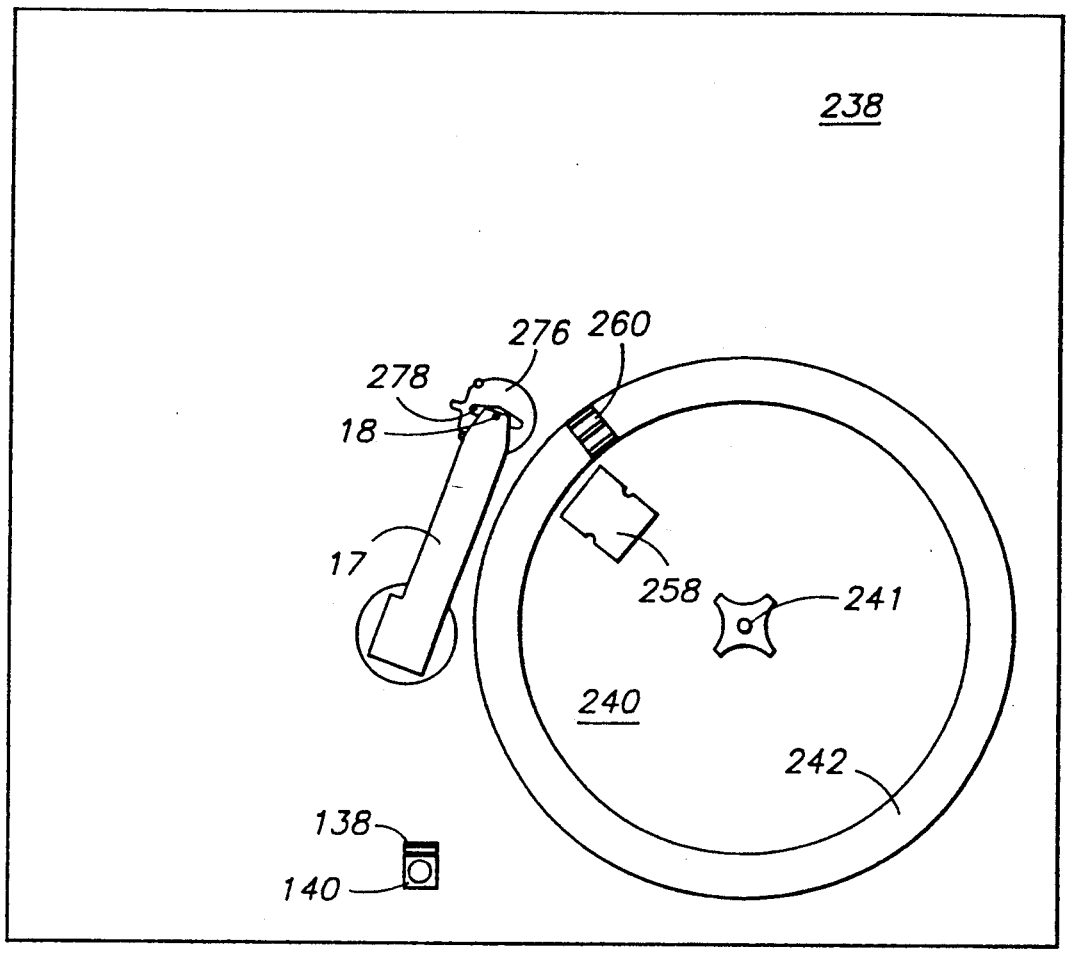
_FIG 66_
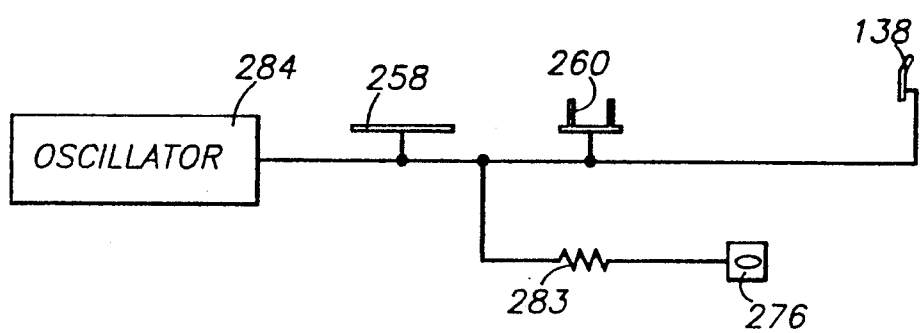
_FIG 67_

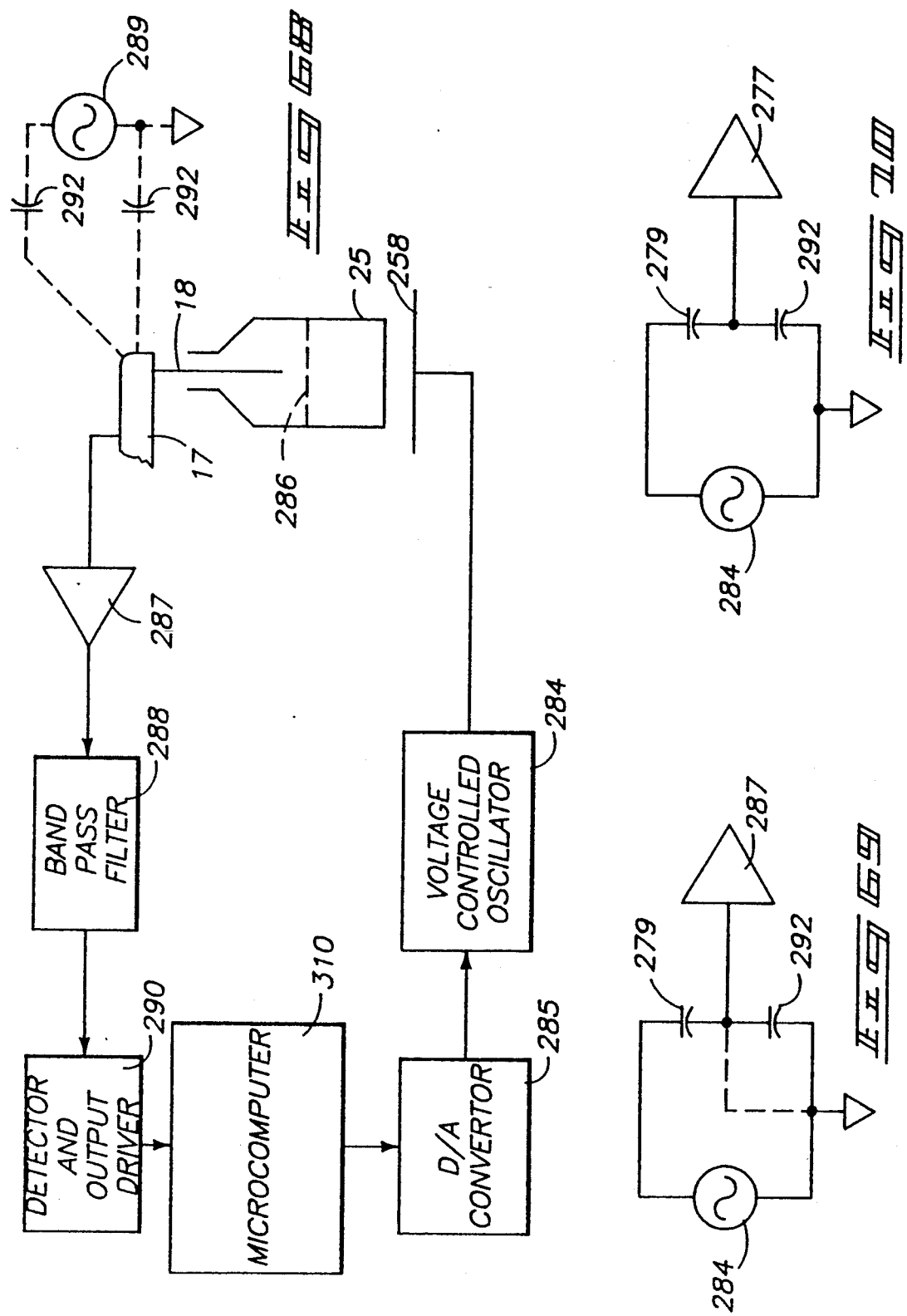

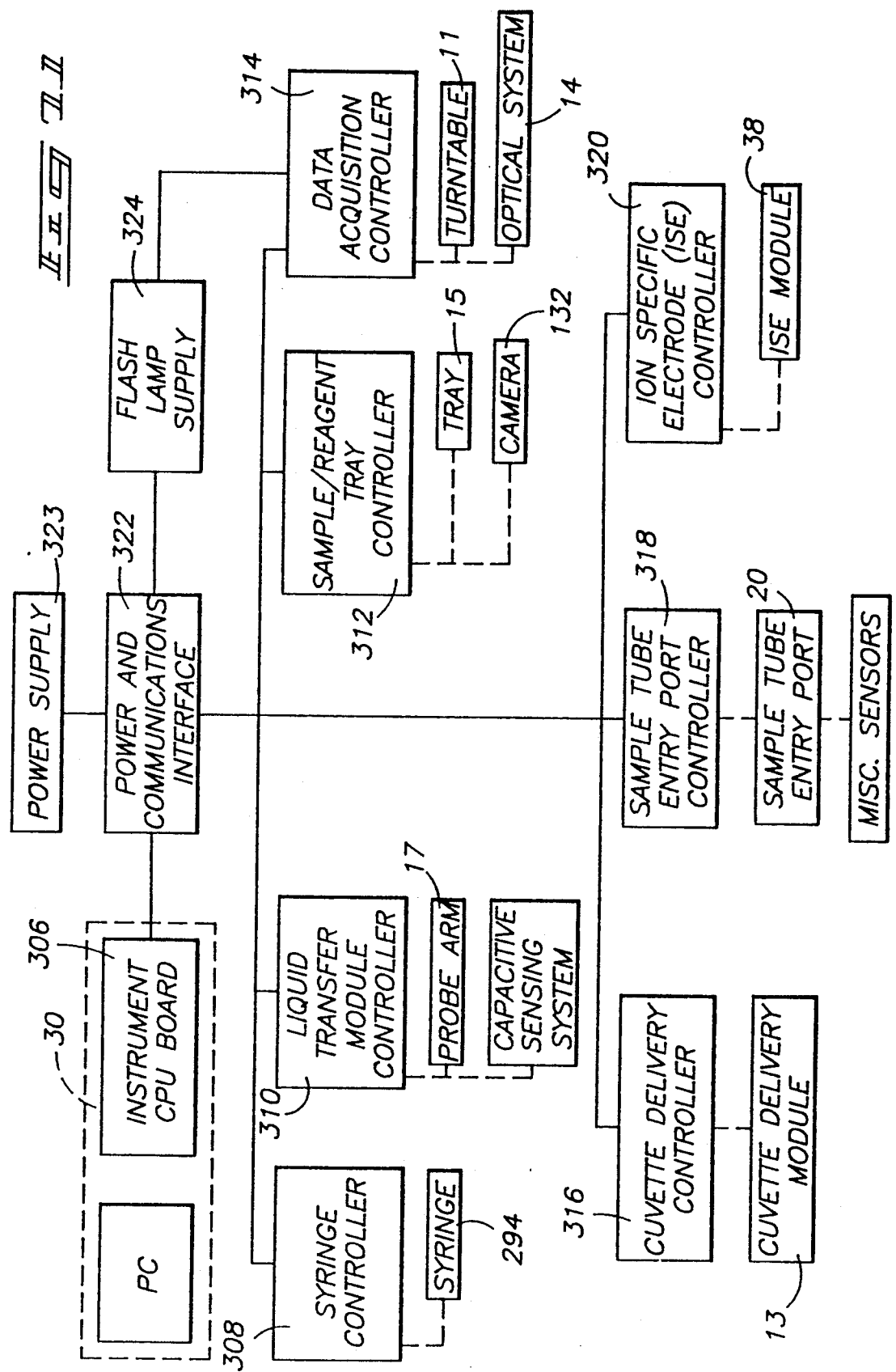

| TURNTABLE 11 | STATIONARY | MIX | ACCEL-ERATE | SPIN | DECEL-ERATE |
|---|---|---|---|---|---|
| PROBE ARM 17 | DISPENSE FLUID | WASH (SHORT) | | | |
| MAGAZINE 75 | INSERT CUVETTE | | | | |
| OPTICAL SYSTEM 14 | MOVE FILTER OUT / TRANSMIT DATA | | | ABSORBANCE READINGS | MOVE FILTER IN / FLOUR-ESCENCE READINGS |

FIG. 72

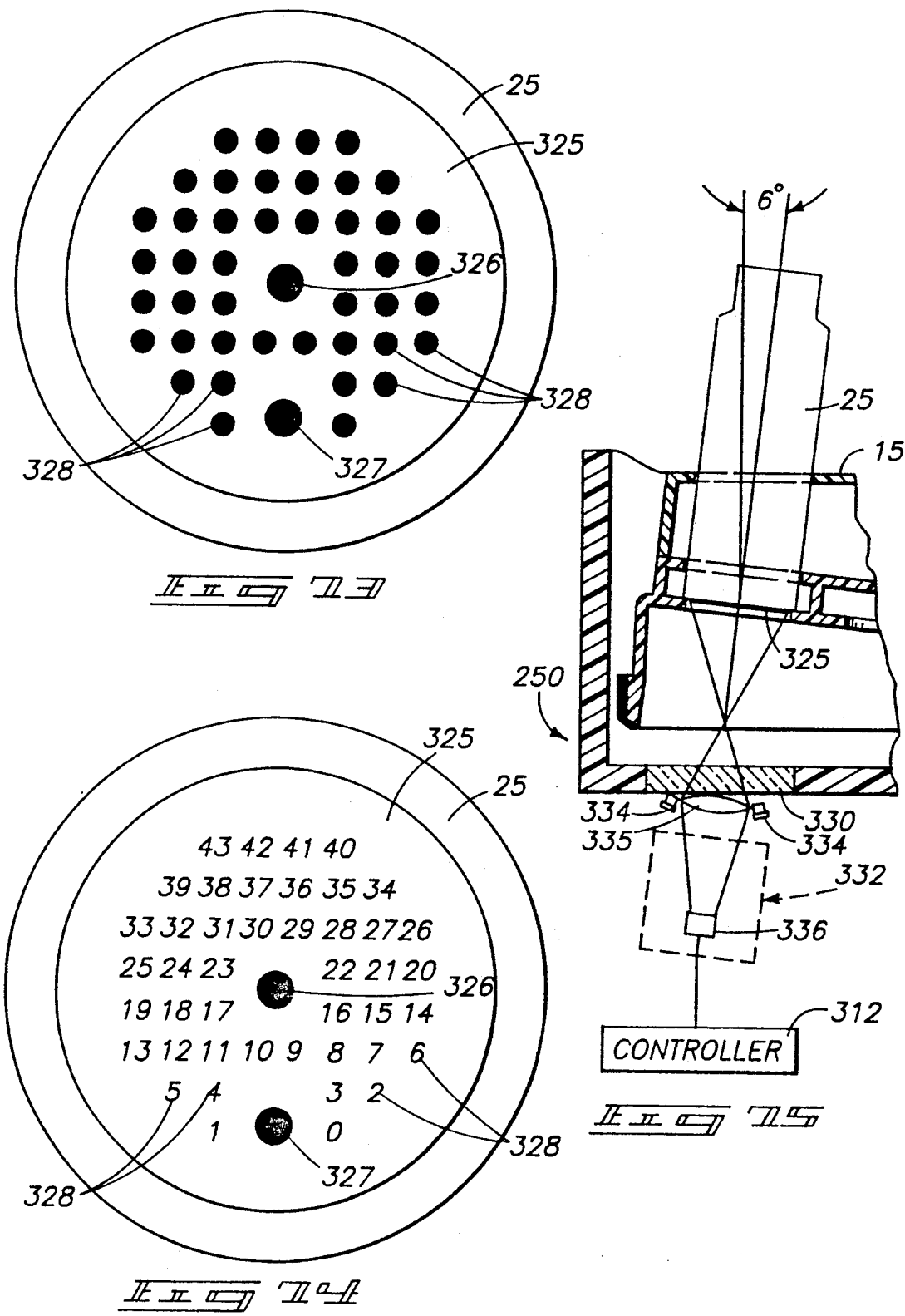

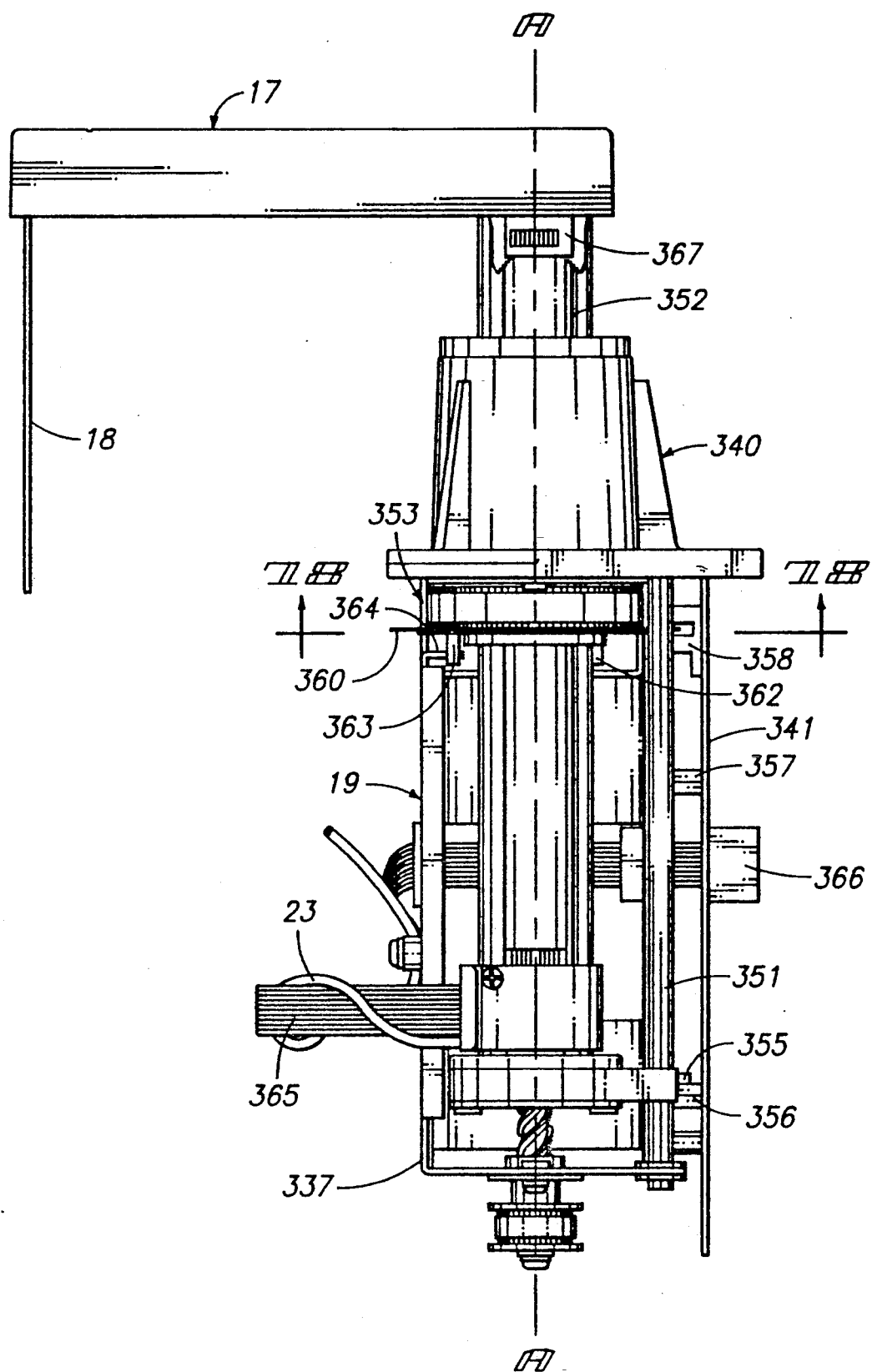

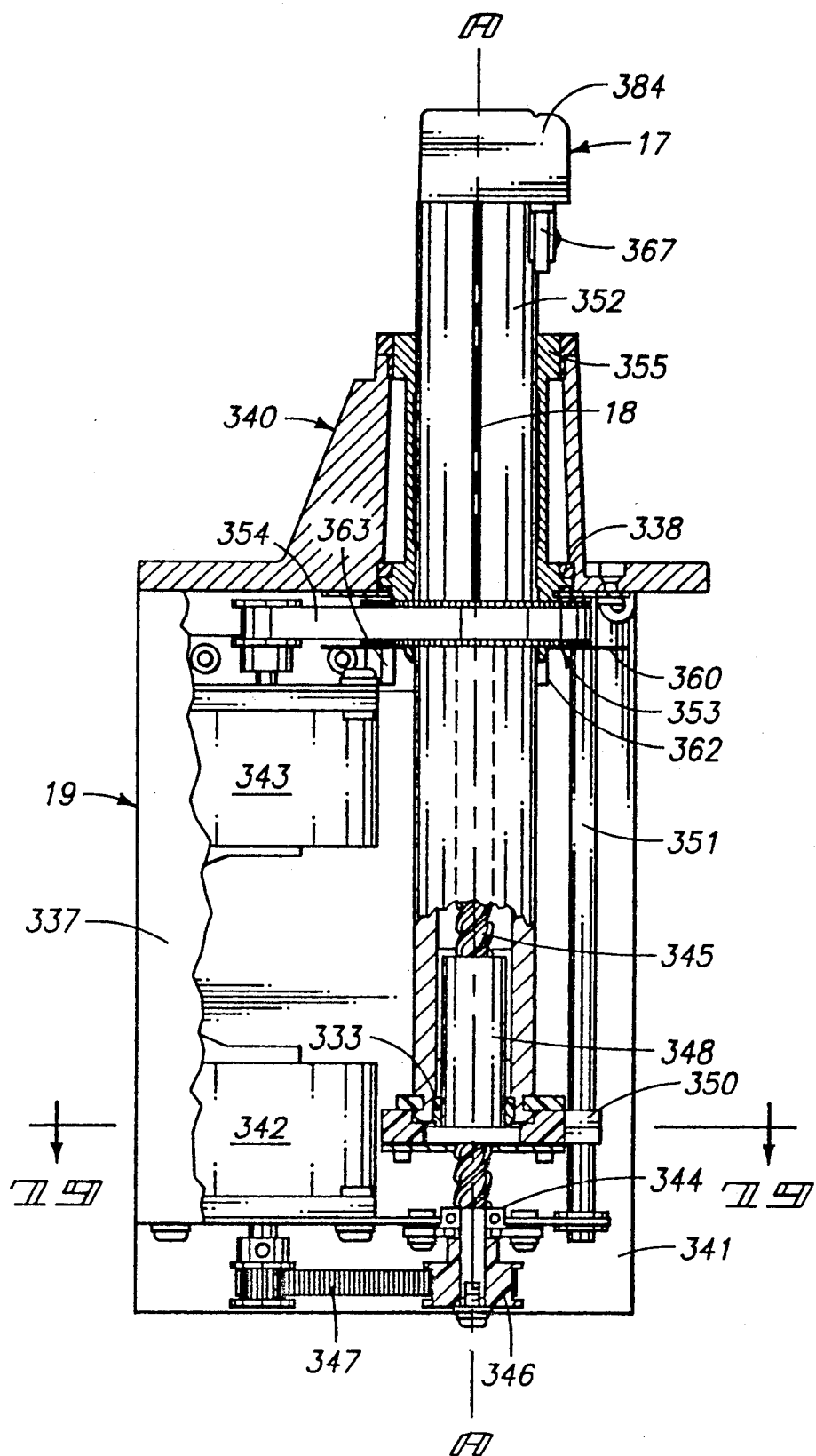

CHEMICAL ANALYZER

TECHNICAL FIELD

This disclosure pertains to a clinical chemistry analyzer for testing of patient samples, such as blood or urine. It generally relates to automatic chemical analyzers for directly measuring properties of reacted liquids by photometric systems to determine optical absorbency and/or fluorescence of samples. The equipment and the disclosed method of operation produces qualitative and quantitative analyses of tested samples.

BACKGROUND OF THE INVENTION

Automated analyzers have been developed for biochemical analysis of patient samples, such as whole blood, serum, urine, plasma and cerebral spinal fluid. Most such equipment available today is large, complicated to operate, and high in cost.

Operation of existing analyzers is technically complicated. the analyzers typically require specialized operators to be available at all times. They are usually designed for use by large laboratories serving a wide geographic area or by a large medical facility. These existing analyzers carry out tests in an inflexible predefined sequence of operations designed only for efficient, high volume usage.

Such large scale capacity is not always required, particularly in smaller medical clinics where large volumes of blood samples are not tested on a daily basis. The present chemical analyzer was developed to meet the varying practical needs of smaller medical settings. It is designed as a flexible desk-top unit that can be operated by one not having extensive laboratory training. Its throughput is adequate for meeting typical clinical applications. As an example, it can be designed to produce a maximum of 164 test results per hour for routine, single reagent chemistries. Its capacity can be effectively doubled by utilizing two of the chemistry instruments in tandem, both being controlled by a common workstation. To provide a representative wide number of reagents, the analyzer has been designed to have a capacity of 40 reagent containers of two different sizes.

The compact nature of the analyzer can be partially attributed to the fact that a single probe arm and pipette service all of the functional liquid-handling components included within it. The common pipette is used for transferring samples and reagents, as well as for diluting liquids as needed by particular test requirements.

To obtain large volumes of tests, conventional laboratory analyzers are programmed to conduct test procedures in a fixed sequence of events. While the use of predetermined test sequences is practical in high volume chemical analyzer applications, there is a need for more flexible operation when scaling such test procedures to meet the needs of smaller medical facilities.

The present invention provides testing flexibility by permitting random access to each cuvette on a test turntable and to each container (cups, wells and reagent bottles) on a sample/reagent tray. It is therefore not necessary for the instrument to sequence through any predetermined processing steps—the controlling software can tailor the required steps to the tests currently requisitioned. This permits a greater number of tests to be conducted while using a minimum number of containers, cuvettes and reagent bottles. The software controls the sequencing of tests based upon predetermined priority schedules, rather than defined test sequences dictated by the nature of the tests being conducted.

Increased versatility is also provided in the present chemical analyzer by providing the capability of inserting pre-loaded reagents within cuvettes fed to a dispensing magazine that directs them to the turntable. Flexibility is further enhanced by providing random access to a plurality of stacks of incoming cuvettes, some of which can be preloaded and some of which can be empty. This provides the capability of random access to prepackaged chemistry involving powdered or solid reagents to supplement the liquid reagents available on the sample/reagent tray.

Most existing analyzers are limited to accomplishing either photometric tests or potentiometric tests, but not both. The present chemistry analyzer, designed about a photometric testing system, has the capability of servicing a second analytical system, such as a potentiometric system. A single liquid transfer system provides samples to both analytical systems. Their operations are controlled by a common workstation, which also processes all resulting data.

The present chemical analyzer also provides the ability to use two chemical instruments in tandem, both being controlled by a single workstation. Using two chemical instruments increases analyzer dependability by providing redundancy of mechanical components. It also allows one chemical instrument to be dedicated to more specialized analytical applications that might require greater time periods or more fragile reagents. Because the two chemical instruments are controlled by a single workstation to minimize duplication, greater volumes of tests can be conducted at a lower additional capital investment than would be required to purchase a larger test system or a duplicate system.

To meet the intermittent needs of medical offices and clinics, as well as the needs of small or specialized hospitals, serum samples can be introduced to the analyzer one at a time in conventional draw tubes, as well as in batches or single units on sample ring segments that are removable from the sample/reagent tray. The latter method of sample introduction is more likely to be utilized in small or specialized hospital settings where the analyzer is associated with more automated sample handling systems.

Most automated analyzers that accommodate samples provided in conventional draw tubes require that such tubes be delivered into the machine in carrousels or on a dedicated conveyor. The draw tubes are then processed as a group over a significant dwell time within the equipment. One feature desirable in many clinical settings is the ability to aliquot samples from a conventional draw tube without requiring the continued presence of the draw tube during the resulting test sequences. This permits the sample material in the tube to be used simultaneously in other equipment during conduct of complementary test procedures.

A sample tube entry port has been designed to facilitate automatic aliquoting of samples from conventional sealed draw tubes without destroying the seals closing the draw tubes or exposing personnel to accidental contact with the sampled materials. It automatically accommodates draw tubes differing from one another in both tube diameter and length.

The present sample tube entry port has been designed to remove a sample promptly upon receipt of a draw tube. It then immediately releases the draw tube for any other current purposes required in the setting in which the chemical analyzer is used.

The automated controls for the present chemical analyzer minimize the need for extensive operator training. Reagent bottles are automatically read and identified by applied computer coded labels. Sample and reagent sensing that occurs automatically during operation of the analyzer notifies the operator of depleted liquid conditions as they occur.

Disposable cuvettes are provided automatically within the analyzer by a cuvette dispenser. Reloading of the cuvettes into a dispensing magazine included in the chemistry instrument is physically organized to meet the supply needs of the instrument with minimum cuvette handling by the operator.

A reaction turntable is capable of handling a maximum of 48 cuvettes at any given time. Both absorbance and fluorescence polarization tests can be carried out with respect to selected cuvettes through use of a single optical system.

Capacitive sensing of liquid levels is used within the chemistry instrument to maintain updated inventory information. A unique capacitive sensing system is used in conjunction with a probe alignment module to monitor both radial and axial positioning of the pipette. These procedures detect bent conditions of the pipette prior to damage of associated equipment.

Further details concerning the system will be evident from the following description.

BRIEF DESCRIPTION OF THE DRAWINGS

The preferred embodiment of the invention is illustrated in the accompanying drawings, in which:

FIG. 9 is a front elevation view of a loaded cuvette cartridge;

FIG. 10 is a transverse sectional view through a loaded cartridge as seen along line 10—10 in FIG. 9;

FIG. 11 is a plan view of the cuvette turntable;

FIG. 12 is an enlarged sectional view taken along line 12—12 in FIG. 11;

FIG. 13 is a transverse sectional view through the turntable as seen along line 13—13 in FIG. 11;

FIG. 14 is a plan view of the cuvette delivery module;

FIG. 16 is a similar rear elevation view, the turntable being removed;

FIG. 17 is a plan of the delivery module with its cover removed;

FIG. 18 is a perspective view of the cuvette magazine;

FIG. 19 is a transverse vertical sectional view of the delivery module as seen along line 19—19 in FIG. 14;

FIG. 32 is a plan view of the assembled sample/reagent tray;

FIG. 33 is a sectional view taken along line 33—33 in FIG. 32;

FIG. 34 is a plan view of the reagent tray;

FIG. 35 is a side elevation view of a cup segment removed from the tray;

FIG. 36 is a plan view of the supporting platform well;

FIG. 37 is a front view of the sample tube entry port module, its front wall being removed;

FIG. 38 is a sectional view taken along line 38—38 in FIG. 36;

FIG. 39 is a sectional view taken along line 39—39 in FIG. 36;

FIG. 43 is a fragmentary side elevation of the ram;

FIG. 44 is a front view;

FIG. 45 is a top view;

FIG. 46 is a sectional view taken along line 46—46 in FIG. 44;

FIGS. 47-59 are a series of diagrammatic views illustrating operation of the sample tube entry port;

FIG. 47 illustrates the initial "home" position;

FIG. 48 illustrates reception of a draw tube;

FIG. 49 illustrates the extreme lowered position of the ram;

FIG. 50 illustrates initial elevation of the draw tube;

FIG. 51 illustrates closing of the cover;

FIG. 52 illustrates puncturing of the tube stopper;

FIG. 53 illustrates initial placement of the probe arm;

FIG. 54 illustrates insertion of the pipette;

FIG. 55 illustrates initial lowering of the draw tube;

FIG. 56 illustrates removal of the pipette;

FIG. 57 illustrates opening of the cover;

FIG. 58 illustrates removal of the draw tube;

FIG. 59 illustrates the final "home" position of the ram;

FIG. 60 is a front view of the wash/alignment module;

FIG. 61 is a top view with the alignment plate removed;

FIG. 62 is a top view with the alignment plate in place;

FIG. 63 is a sectional elevation view taken along line 63—63 in FIG. 61;

FIG. 64 is an enlarged diagrammatic view illustrating use of the pipette alignment plate;

FIG. 65 is a schematic view of the syringe module;

FIG. 66 is a simplified plan view of the sensing components arranged on the supporting platform;

FIG. 67 is a simplified diagram of the wiring connections between the sensing plates and oscillator;

FIG. 68 is a block wiring diagram of the sensing circuit;

FIG. 69 is a simplified equivalent circuit diagram;

FIG. 70 is a second equivalent circuit diagram;

FIG. 71 is a block diagram of the instrument controllers;

FIG. 72 is a timing diagram for the instrument components;

FIG. 73 is a bottom view of a labelled bottle;

FIG. 74 is a similar view, showing the label encoding pattern;

FIG. 75 is a diagrammatic view of the label reading equipment in a chemical instrument;

FIG. 76 is a front elevation view of the liquid transfer module;

FIG. 77 is a side elevation view, with portions of the module frame being broken away;

DETAILED DESCRIPTION OF THE PREFERRED EMBODIMENT

Figure 1:
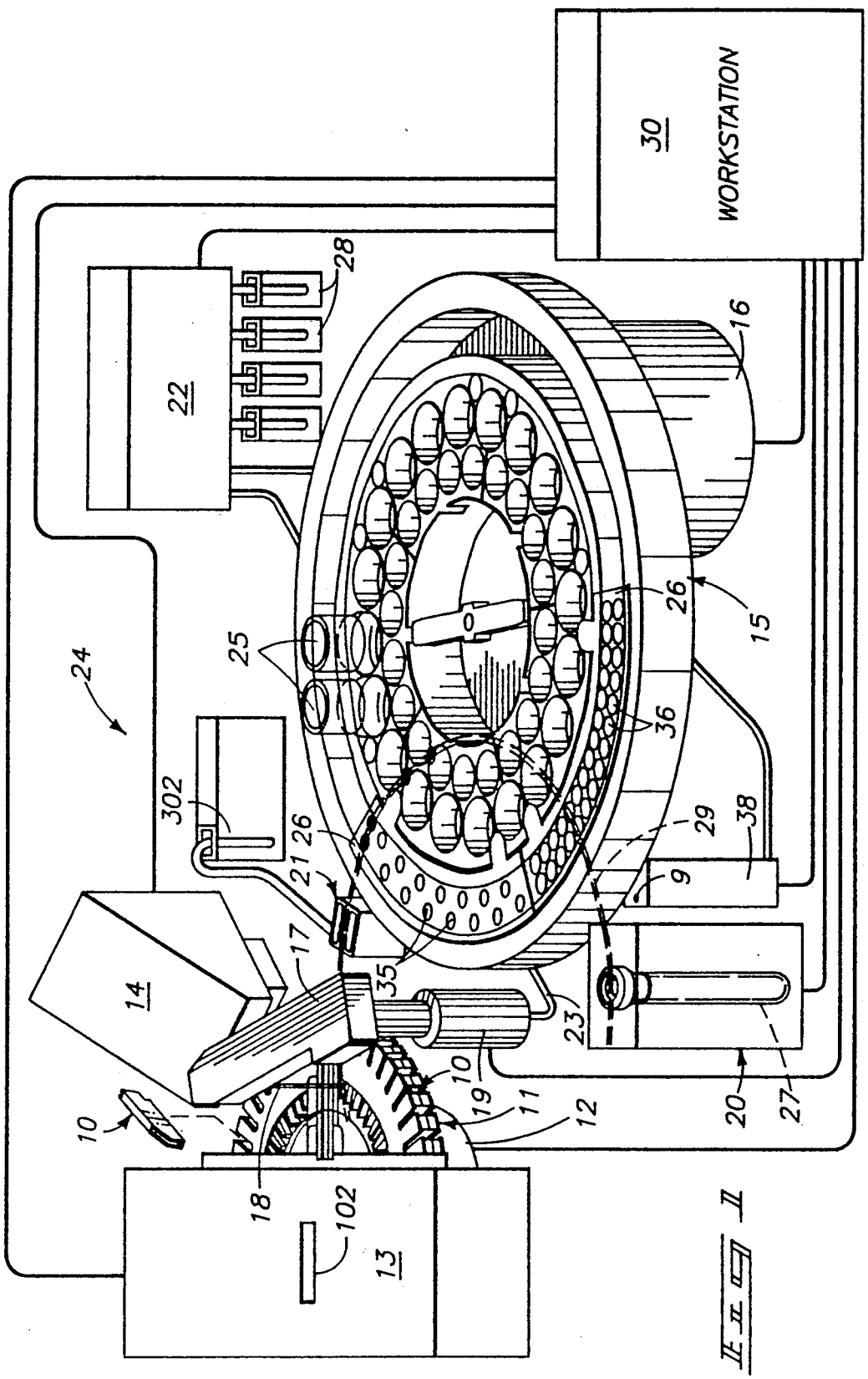
FIG. 1 is a diagrammatic perspective view of the principal components in the analyzer.

This disclosure of the invention is submitted in furtherance of the constitutional purposes of the U.S. Patent Laws "to promote the progress of science and useful arts" (Article 1, Section 8).

EQUIPMENT DESCRIPTION

System Overview

The automatic chemical analyzer (generally illustrated in FIGS. 1-3) includes a turntable 11 rotatably mounted about a first vertical axis. A plurality of disposable cuvettes 10 are releasably mounted to the turntable 11. A first power means, shown as motor 12, is operably connected to turntable 11 for alternately (1) indexing it at a stationary angular position about the first axis with a selected cuvette 10 positioned at a cuvette access station A or (2) turning it about the first axis while mixing or centrifuging contents of cuvettes mounted to it.

First analytical means, illustrated as an optical system 14, is provided adjacent to the turntable 11 for performing tests on the contents of the cuvettes 10 as they rotate about the turntable axis.

A tray 15 is rotatably mounted about a second vertical axis parallel to and spaced from the first axis. A plurality of containers 25, 35, and 36 are positioned about tray 15 for reception of samples and reagent liquids. Second power means, illustrated as motor 16, is operably connected to the tray 15. The motor 16 indexes tray 15 to a stationary angular position about the second axis with a selected container positioned at a container access station C.

The analyzer also includes a probe arm 17 movable about a third vertical axis parallel to the first axis. Probe arm 17 supports a downwardly-extending open pipette 18. The vertical pipette 18 is movable along an arcuate path centered about the third axis and intersecting both the cuvette access station A and container access station C. It can move along the arcuate path in a random fashion to transfer liquid from a container positioned on the tray at the container access station C to a cuvette 10 positioned on the turntable 11 at the cuvette access station A. The arcuate path of the pipette 18 can be visualized along a protective groove 29 formed at the exterior of the enclosure 39 housing the chemistry instrument 24.

The illustrated embodiment of the clinical chemistry analyzer consists of two major components: a chemistry instrument 24 and a workstation 30. The chemical instrument accepts liquid patient samples for testing purposes, performs appropriate optical and/or potentiometric measurements on the samples, and communicates the resulting test data to workstation 30. Workstation 30 is used by the operator to enter data, control operation of instrument components, accept data generated by the instrument, manage and maintain system information, and generate visual and printed reports about assays and instrument performance.

The chemistry instrument 24 is a separate unit with minimal operator controls. Either one or two identical chemistry instruments 24 can be linked to a single workstation 30, as required in a particular setting. The chemistry instrument 24 can perform several types of analysis. These include routine chemistries, electrolytes, therapeutic drug monitoring, drugs of abuse in urine, and other specialized tests.

The liquid-handling components that make up the chemistry instrument 24 are housed within enclosure 39 (FIGS. 2-5). It separates along a peripheral parting line 37 defining a lower supporting base 33 and an upper hinged cover 34.

The principal modular components of the chemistry instrument 24 are diagrammatically illustrated in FIG. 1. The illustrated components are specifically designed for use in association with a specially designed liquid cuvette 10, detailed in FIGS. 6-8. Supplies of new cuvettes 10 are introduced into the system in stacks within a cartridge 40, which is shown in FIGS. 9 and 10.

A computerized operator interface to the chemistry instrument 24 is provided through connections to the programmable workstation 30. Most of the operator interactions with the analyzer take place at workstation 30. It is an external desktop computer located near the chemistry instrument(s) 24. It uses an industry standard operating system and bus structure, plus a hard disk. It is also provided with a custom instrument interface board for each associated chemistry instrument, diagrammatically illustrated in FIG. 71.

Operations required for sample testing of cuvette contents are not carried out in any predetermined sequence dictated by insertion of a sample into the chemistry instrument 24. Instead, workstation 30 serves as random access control means operably connected to the turntable 11, tray 15 and probe arm 17 for selectively transferring liquid from any container on the tray 15 to any cuvette 10 on the turntable 11 according to defined logical priority rules programmed into the workstation.

Operations carried out within the chemistry instrument 24 are timed about a repetitious cycle of operations shown in FIG. 72. Each cycle involves sequentially transferring liquids to an awaiting cuvette 10 on the turntable 11, mixing the liquids, and centrifuging them for test purposes.

A monitor 31 is included within workstation 30 to display data, messages and optional menus for the operator. A keyboard 32 is included for operator input of data and instructions. A printer (not shown) of conventional design can also be provided in the system to record tests results and reports as required.

A plurality of test cuvettes 10 are releasably located within a motor-controlled turntable 11 shown in FIGS. 11–13. It is powered by a DC motor 12. Motor 12 can be accurately controlled to (1) selectively index turntable 11 at a chosen angular position about its vertical axis for access to a particular cuvette and/or insertion of new cuvettes or (2) intermittently or reversibly rotate turntable 11 about its axis for mixing the contents of the cuvettes or (3) spin turntable 11 for centrifuging the contents of the cuvettes during photometric analysis.

A liquid transfer module (FIGS. 76–84) includes a single probe arm 17 movably supported on the instrument 24 about a vertical axis. The outer end of probe arm 17 carries a downwardly extending pipette 18. Pipette 18 is used for transferring liquids between various locations about the chemistry instrument. Its lower or outer end is open for receiving or discharging liquids.

Probe arm 17 is supported and powered by a positioning assembly 19. The positioning assembly 19 has two stepper motors—one for imparting rotational motion to probe arm 17 and one for imparting vertical motion to it. Positioning assembly 19 can selectively move probe arm 17 and pipette 18 both angularly and axially relative to the vertical axis of probe arm 17.

The tip or lower end of pipette 18, while in an elevated condition permitting angular movement about the chemistry instrument 24, projects slightly into an open arcuate groove 29 (FIGS. 2, 3) formed about the cover 34 of the instrument enclosure. Groove 29 is centered about the axis of probe arm 17 and is recessed within cover 34. It overlaps the bottom of pipette 18 to prevent its accidental engagement with the hands of an operator as the pipette travels from one station to the next. The protective overlap of the pipette tip eliminates the danger of accidently impaling adjacent personnel when pipette 18 is subsequently lowered.

A cuvette dispenser module 13 (FIGS. 14–23) is arranged on the framework of the equipment in a position immediately above the turntable 11. It includes a storage magazine for a plurality of stacks of curvettes 10. It also includes an apparatus for transferring individual cuvettes 10 from a randomly selectable stack within the magazine 75 to a receiving compartment on turntable 11. Used cuvettes 10 are discarded into a removable cuvette disposal container (not shown0 as new cuvettes are delivered to the turntable 11 by operation of a reciprocating ram. The cuvette disposal container can be a bag or bin into which used cuvettes drop when ejected from turntable 11.

The optical system 14 (FIGS. 24–31) is contained within a housing positioned next to turntable 11. Optical system 14 performs photometric tests on the contents of cuvettes 10 while they are being spun about the turntable axis. The optical system 14 measures both fluorescent emissions and light absorbance by cuvette contents within the turntable 11. Photometric test groups typically supported include routine chemistries, special proteins, therapeutic drugs, and drugs of abuse.

For absorbency tests, the optical system 14 measures radiation at 180 degrees to the incident light. Readings are made at several wavelengths on a diode array, but only those points requested in specified test parameters are processed by the instrument 24. System offsets are subtracted from the results and the sample signal is divided by a reference signal. The negative logarithm of this ratio is the absorbance.

When conducting fluorescent tests, emitted radiation at a wavelength longer than that of the source is measured at 90 degrees to the incident beam. System offsets are subtracted and the intensity is then normalized using a reference signal.

A sample/reagent tray 15 (FIGS. 32–35) is rotatably mounted about a vertical axis parallel to and spaced from the axis of turntable 11. It is rotatably powered by a stepper motor 16. Tray 15 consists of a circular reagent bottle support surrounded by separate interlocking ring segments 26. The removable ring segments 26 are used to hold reagents and samples required for assay procedures during operation of chemistry instrument 24.

Tray 15 supports a plurality of liquid containers, namely the reagent bottles 25, open cups 35 and open wells 36. The interchangeable ring segments 26 have two alternate configurations. One includes apertures for removably supporting individual sample cups 35. The other includes a plurality of integrally molded sample wells 36.

The individually removable cups 35 serve as containers for test samples supplied to the instrument 24 by the operator within one or more cups within a ring segment 26. Wells 36 are used by the instrument components in conjunction with operation of probe arm 17 for aliquoting of samples from a draw tube and for sample dilution purposes. The probe arm 17 can selectively transfer liquids from one well 36 to a second well 36, from a cup 35 to a well 36, or from a reagent bottle 25 to a well 36.

Access to the sample/reagent tray 15 is provided by a hinged tray access cover 8 formed in the enclosure cover 34. More limited manual access to a single ring segment 26 located at the front of the chemistry instrument 24 is provided by a hinged segment access port 7, which is a sub-assembly of cover 8.

Figure 3:
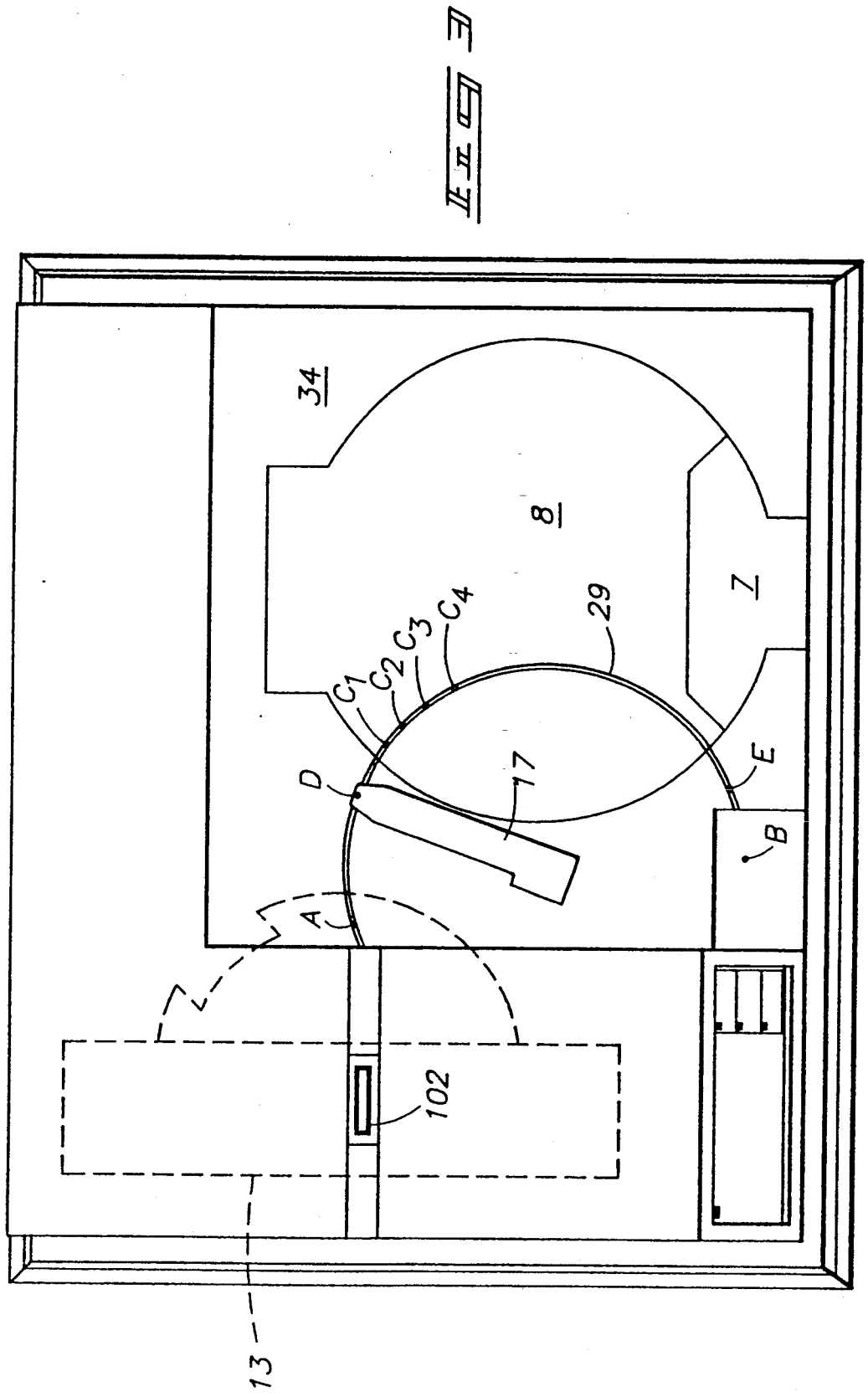
FIG. 3 is a plan view of the chemical instrument enclosure.

A stepper motor 16 can be operated to index sample/reagent tray 15 to a selected position about its axis with one or more selected containers at one of four container access stations shown in FIG. 3 at locations $C_1$, $C_2$, $C_3$, $C_4$ on the equipment framework. Each container access station intersects the path of pipette 18, which is coincident with groove 29.

Scanning means is provided next to the tray 15 for capturing identifying information from encoded indicia on a container positioned on it.

A cooling system (not shown) for the chemistry instrument 24 incorporates multiple thermoelectric cooling units. These are needed in the areas of the sample/- reagent tray 15 and the turntable 11. Heat can be removed from the system by air exchange through a plurality of heat sinks.

A sample tube entry port 20 (FIGS. 37-59) is provided on the framework for receiving and supporting successive individual draw tubes 27 as they are introduced into the instrument by the operator. Its primary use is to permit the taking of aliquots from positively identified, sealed patient draw tubes. It can also be used for delivery of control liquids from tubes of a similar exterior configuration, whether covered or open. Positive identification can be provided by an encoded label on each draw tube 27. The label is scanned by a bar code reader included within the sample tube entry port 20.

Each draw tube 27, of conventional design, is sealed by a closure at its upper end. Sample tube entry port 20 supports each manually inserted draw tube 27 while pipette 18 pierces the closure 162 to access liquid sample material from the tube interior. Liquid removal from successive tubes 27 occurs at a sample access station B along the arcuate path 29.

Puncturing means are provided within the sample tube entry port 20 for temporarily forming an opening through a closure on a manually-delivered draw tube 27 placed within it. A ram positioned below the puncturing means receives and coaxially orients a manually placed draw tube 27 relative to the puncturing means. It moves the draw tube parallel to a fourth vertical axis (centered along the puncturing means) between a lowered position wherein the draw tube 27 is clear of the puncturing means and a raised position wherein the puncturing means forms a temporary opening through the draw tube closure for subsequent coaxial insertion of the pipette 18. The interior of the draw tube 27 is then accessible by subsequently inserting pipette 18 coaxially through the puncturing means.

A wash/alignment module 21 (FIGS. 60-64) is located at a fixed position on the framework. Its first purpose is to provide vertical basins within which the lower end surfaces of pipette 18 can be flushed clean during or after liquid transfer cycles. It also supports a conductive sensing plate that verifies both the radial alignment and elevational position of pipette 18 about the pipette axis on the probe arm 17 for monitoring alignment of the pipette. These operations occur at a wash/alignment station D along the arcuate path 29 of pipette 18.

A capacitive sensing circuit (FIGS. 66-70) is operably connected to the pipette 18 and to conductive members located next to the tray 15 and within the sample tube entry port 20. The sensing circuit detects the level of liquid in a container on the tray or a draw tube 27 as it is approached by the pipette.

A second analytical means, shown as an Ion Specific Electrode (ISE) module 38 of conventional design and operation, is included within the chemistry instrument 24. It is illustrated generally in FIG. 1. Potentiometric tests may be requested and run by the ISE module 38 simultaneously with photometric tests being conducted by the optical system 14.

Samples are delivered to the ISE module 38 by pipette 18 at a sample delivery station E along the arcuate path 29 (FIG. 3). Module 38 can include tests for the presence of a variety of analytes, such as sodium, potassium, chloride, lithium or calcium. For each analyte, all sample types are analyzed in the same manner. The different sample types can be loaded using different dilution factors.

The ISE module 38 consists of electrodes specific to the chosen analyte, a reference electrode and the associated fluid system required to process tested samples. The potentiometric measurement consists of a voltage difference between the analyte's electrode and the reference electrode.

Water is supplied to pipette 18 from a syringe module 22 connected to a water supply container in a container rack 28. The syringe module 22 consists of a volume displacement syringe and associated valves leading to a source of water and a waste water container (not shown). It is used for all aspirations of samples, reagents and diluents in the chemistry instrument 24. The syringe module, of conventional design, is diagrammatically illustrated in FIG. 65.

Tubing 23 (FIG. 1) connects syringe module 22 to pipette 18. Tubing 23 contains water that can be moved in opposite directions to receive or discharge liquids at the lower end of pipette 18.

The above components are individually operable under control of a distributed computerized controller system (FIG. 71) governed by the programmable workstation 30. Workstation 30 is electronically linked to the instrument via a bi-directional communications interface. This interface is used to communicate patient requisitions to the chemistry instrument 24 and to receive the associated test results from the instrument 24. All control functions can be randomly initiated under control of scheduling software and logic to match pending requisition requirements and current instrument status conditions.

The external computer can send patient requisitions to the workstation either individually or in ring segment groups. The workstation can send test results to the external computer.

The control system associated with chemistry instrument 24 includes several dedicated microprocessors and programmable memory devices. They individually operate the system components as prioritized by scheduling software residing in the instrument CPU board 306. The workstation 30 includes monitoring means for maintaining a current record of the amount of liquid in containers on the sample/reagent tray 15. Controlling software associated with the microprocessors causes the mechanical components of the chemistry instrument 24 to carry out all operations efficiently and effectively without operator intervention, using a random sequence of movements dictated by outstanding test requirements.

The arrangement of operational stations along the arcuate path of pipette 18 permits transfer of liquids from a draw tube 27 at the sample access station B to a well 36 at a container access station $C_1$ or $C_2$ on the sample/reagent tray or from a well 36 to a cuvette 10 at the cuvette access station A on turntable 11. Alternately, pipette 18 can transfer sample diluents (buffers) from the reagent bottles 25 at container access stations $C_3$ or $C_4$ on the sample/reagent tray 15 to a well 36 at a container access station $C_1$ or $C_2$. In addition, it can transfer liquids from one well 36 to another, or from a cup 35 to a well 36 for dilution purposes at container access stations $C_1$ or $C_2$. Direct transfer of reagents from bottles 25 to cuvettes 10 can also take place at cuvette access station A. A wash or pipette alignment procedure can also be periodically accomplished at wash/alignment station D as required. ISE tests are initiated by optional delivery of sample liquids to the ISE station E.

Cuvettes

Figure 6:
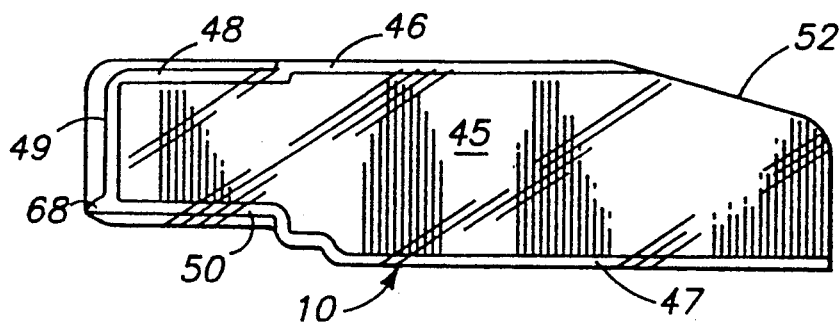
FIG. 6 is a side elevation view of a cuvette.
Figure 7:
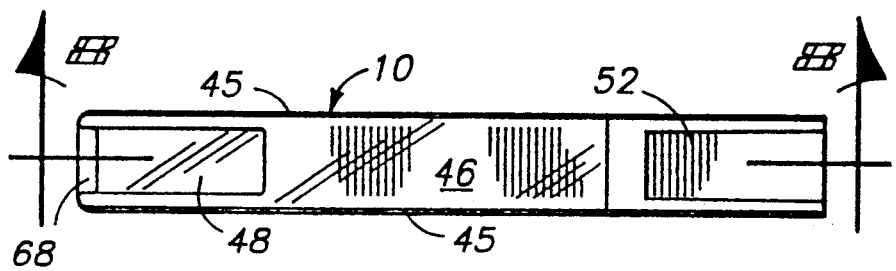
FIG. 7 is a top view.
Figure 8:
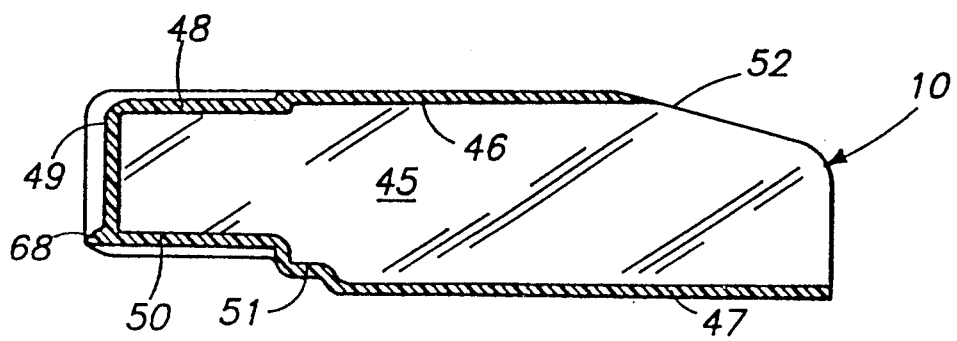
FIG. 8 is a sectional elevation view taken along line 8—8 in FIG. 7.

The disposable cuvettes 10 designed for use in turntable 11 are illustrated in detail in FIGS. 6-8. A complementary cartridge 40 for handling and storing the cuvettes is shown in FIGS. 9 and 10.

Cuvettes 10 are molded from a suitable transparent rigid plastic material that is liquid impervious and inert to the liquids which they are to contain. The cross-sectional configuration of each cuvette is rectangular.

Each cuvette 10 includes two identical side walls 45 having parallel top and bottom edges. The straight top and bottom edges along each side wall 45 longitudinally overlap one another to facilitate stacking of the cuvettes in abutting parallel positions. Side walls 45 are transversely joined by parallel spaced top and bottom walls 46 and 47.

One end of each cuvette 10, termed its "upper end", includes an opening 52 between the end edges of the side walls 45. Opening 52 provides access to the interior of cuvette 10 for receipt of liquids. The edges of side walls 45 that form the opening 52 include angular edges intersecting the straight top edges of the respective side walls 45. The angular edges assume horizontal orientations when positioned in turntable 11 (FIG. 12). The end edges along the opening 52 are perpendicular to the top and bottom walls 46 and 47. In the case of cuvettes that are pre-loaded with reagents or other materials prior to usage in the chemistry instrument 24, opening 52 can optionally be sealed by a suitable film or other cover (not shown) capable of being pierced by the descending tip of pipette 18.

The opposite end of each cuvette 10, termed its "lower end", includes perpendicular optical surfaces for transmission of light in conjunction with operation of the optical system 14. These surfaces comprise top, end and bottom optical surfaces 48, 49 and 50, respectively. Each optical surface area is slightly recessed inwardly from the outer edges of side walls 45 to protect it from abrasion or contact during handling.

The lower end of each cuvette 10 also is provided with a transverse protruding wall 68 extending across the two side walls 45. Wall 68 provides a continuous transverse surface for abutment of the upper end of an adjacent cuvette 10 when one cuvette pushes another into position within turntable 11.

A small downwardly-facing recess 51 is provided within the bottom wall 47 of each cuvette 10 adjacent to the inner end of lower optical surface 50. The recess 51 serves as a detent in conjunction with a spring-biased enlargement (see FIG. 12) that yieldably holds cuvette 10 within a receiving compartment on the turntable 11.

The cuvettes are preferably packaged within elongated disposable cartridges 40 (FIGS. 9 and 10). The parallel stacked cuvettes 10 face oppositely at the respective ends of cartridge 40, which is designed for insertion into the open slots of a receiving cuvette magazine 75 detailed in FIG. 18.

The cuvette cartridge 40 is formed from a C-shaped channel 41 having interior surfaces complementary to the exterior shape and size of the individual cuvettes 10. Cartridge 40 can be formed from any suitable stiff, resilient plastic sheet or can be extruded in the shape generally illustrated in FIGS. 9 and 10. Its purpose is to facilitate handling and storage of the large quantities of cuvettes 10 required by each chemistry instrument 24. Its use expedites manual entry of cuvettes 10 into the storage magazine 75.

Cuvettes 10 fit transversely within the elongated channel 41 in abutting parallel positions within two groups. Each group of cuvettes 10 at the respective ends of cartridge 40 equals a full stack of cuvettes within the receiving magazine 75. Two pairs of inwardly bent stops 42 near the center of cartridge 40 limit inward motion of cuvettes along the length of the magazine. Outward movement of cuvettes at each end of the cartridge 40 is resisted by smaller end stops 43 bent inwardly in the path of cuvettes 10 as they exit the cartridge 40.

Turntable

Turntable 11 is generally detailed in FIGS. 11-13. It comprises a circular, radially-slotted wheel rotatably mounted about a vertical axis X—X (FIG. 13). The outer periphery of the turntable 11 presents a series of equiangularly spaced radial compartments 53. Each compartment 53 individually receives a cuvette 10 in the manner shown in FIG. 12.

Each compartment 53 comprises a radial slot having an interior cross-sectional shape and size that is complementary to the exterior cross-sectional shape and size of a cuvette 10. The compartments 53 are arranged about turntable 11 at an oblique angle such that the angular upper edge of each cuvette opening will be oriented horizontally and perpendicular to the axis X—X. The oblique nature of each compartment also positions the optical end of each cuvette 10 at a lower elevation than opening 52 so that liquids will be contained within each cuvette without spilling, even when the turntable 11 is stationary.

An axial slot 54 intersects each compartment 53 across its outer end. Slots 54 extend through the upper and lower surfaces of the turntable 11. They provide light access to the optical surfaces 48-50 of cuvettes 10. Slots 54 permit passage of light through the individual cuvettes 10 and are used in conjunction with operation of the optical system 14 to facilitate photometric testing of cuvette contents while within the turntable 11.

The cuvettes are yieldably held within the radial compartments 53 by spring 55 (FIGS. 12, 13). The outer ends 61 of the longitudinal springs 55 are enlarged to enable them to fit within the recesses 51 formed in the cuvettes 10. The spring ends 61 constitute yieldable detentes that radially limit outward movement of each cuvette 10 relative to the turntable 11.

Springs 55 also serve as interior supports within compartments 53. They yieldably maintain the top walls 46 of cuvettes 10 in engagement with the upper inside surfaces of the compartments 53. The cover 59 about turntable 11 is fabricated of an electrically conductive plastic material. Springs 55 maintain firm surface-to-surface contact between the top wall 46 of each cuvette 10 and the interior surface of cover 59. This provides effective heat transfer to each cuvette to minimize the time required to warm it in preparation for receipt of a test sample. The cover 59 can be heated as the turntable 11 is rotated, using an adjacent stationary source of controlled heat (not shown).

Cuvettes 10 held within the turntable 11 are individually accessible and open for reception of samples and reagents as required by requisitioned assays. Liquids are introduced through the openings 52 of the respective cuvettes 10 by operation of probe arm 17 and pipette 18 at the previously-identified cuvette access station A. All incubation of samples involved in an assay occurs within cuvettes 10 in the turntable 11.

The upper surface of the supporting central plate 56 on turntable 11 is provided with a plurality of tapered radial guide surfaces 57. Surfaces 57 are centered between each radial compartment 53 and are obliquely aligned with the respective compartments 53. They are utilized to accurately index turntable 11 during reception of incoming cuvettes. This indexing feature will be described in conjunction with the interaction between the cuvette dispenser module 13 and turntable 11.

As can be seen in FIG. 12, the turntable 11 holds cuvettes 10 in elevationally tilted radial positions with their openings 52 exposed for reception of liquid materials. At the same time, their optical surfaces 48, 49 and 50 are exposed through slots 54 for transmission of light as required by operation of optical system 14. Turntable 11 is rotatably supported about a stationary vertical shaft 62 (FIG. 13) fixed to the supporting framework of the chemistry instrument 24. It is rotated by peripheral gear teeth 63 that are drivingly engaged with a motor-driven gear (not shown) operatively powered by motor 12.

Indexing of turntable 11 is accomplished by a circular slotted rim 60 that rotates between a light sensor 74 on the framework of the chemistry instrument. A rotational "home" position of turntable 11 is defined be a depending flag 129 and a second sensor 139.

Cuvette Delivery Module

The cuvette delivery module 13 is located across the left hand end of the enclosure for the chemistry instrument, as shown in FIG. 3. A plan view of the cuvette delivery module 13 is illustrated in FIG. 14. It is further illustrated in FIGS. 15–23. It overlies turntable 11 at an oblique angle aligned with the compartments 53 (see FIG. 19).

Cuvette delivery module 13 provides automated storage for a plurality of stacks of cuvettes 10 delivered to it from manually-inserted cartridges 40. The cuvettes 10 are stored in parallel upright stacks within a longitudinally shiftable magazine 75. The magazine 75 is separately illustrated at FIG. 18.

Cuvettes discharged from a selected stack within magazine 75 are individually inserted into a selected compartment 53 on the turntable 11. Insertion of a cuvette 10 into a turntable compartment 53 in turn ejects the cuvette 10 previously within it (see FIG. 19). Ejected cuvettes can be temporarily stored within a rigid or flexible container (not shown) on the framework of the chemistry instrument 24. The receiving container should be upwardly open, allowing the ejected cuvettes 11 to drop freely into it from the turntable 11.

Magazine 75 is capable of randomly accessing individual cuvettes from the lower end of any one of its multiple stacks. This capability is of particular value when stacks of pre-loaded cuvettes containing differing reagents are stored in magazine 75. When simply using empty stored cuvettes 10, the stacks of cuvettes within magazine 75 will be accessed in sequence, with all of the cuvettes in a stack being delivered to the turntable 11 before a subsequent stack is used.

Magazine 75 comprises an elongated, rectangular, box-like structure including transversely spaced side walls 76 and 77. Walls 76 and 77 support opposed inner upright walls 78. The inner walls 78 define a series of upright slots, each slot having a width and thickness complementary in size to the corresponding dimensions of a cuvette cartridge 40. The slots are therefore sized to complement the exterior length and thickness of the stacked cuvettes 10. The stacked cuvettes 10 fit loosely within the receiving slots. They are fed downwardly within the slots for eventual individual discharge at the bottom of each stack.

The stationary support for the movable magazine 75 is fixed within the hinged cover 34 of the exterior enclosure for the chemistry instrument 24. It includes a base 81 and attached vertical end walls 80. An arcuate hood 95 is integral with base 81 and covers most of the protruding portions of turntable 11. It is interrupted about a portion of its periphery by an opening 73 to expose an arcuate section of the turntable 11, as can be seen in FIGS. 14–17.

Hood 95 has an open aperture 128 formed through it. Aperture 128 is positioned at the cuvette access station A shown in FIG. 3. Pipette 18 can freely pass through aperture 128 to locate its lower end or tip within the opening 52 at the upper end of an indexed cuvette 10 on turntable 11 for discharge of fluid.

Magazine 75 is covered by a top wall 82 arranged between the end walls 80 in close proximity to the upper ends of the magazine slots. The top wall 82, which can include removable access panels, prevents cuvettes from falling from the magazine when the cover 34 of the enclosure is lifted about its hinges.

Magazine 75 is longitudinally guided on a pair of horizontal rods 79 extending between the end walls 80. Side wall 76 of magazine 75 is provided with spaced bushings 83 that slidably support magazine 75 along the horizontal rods 79.

An exterior rack 84 along the outer surface of the magazine wall 76 imparts longitudinal motion to it. The longitudinal position of magazine 75 relative to the module base 81 is controlled by operation of a stepper motor 86 that drives magazine 75 through a gear 87 in mesh with rack 84 (see FIG. 19). Motor 86 is fixed to an upstanding side plate 88 at the center of module 13.

A longitudinal indexing strip 85 along the wall 76 of magazine 75 is periodically slotted to facilitate optical indexing of magazine 75 relative to its supporting structure within the cuvette delivery module 13. Plate 88 mounts a light sensor 89 that straddles the indexing strip 85 to detect the positions of the slots in indexing strip 85. Associated electronic components for the sensor 89 can be provided on a circuitboard shown at 91.

Cuvettes 10 located within magazine 75 freely rest on a smooth planar upper surface 90 presented across the module base 81. The surface 90 is interrupted only by a central transverse slot 92 through which the lowermost cuvette 10 in a stack aligned above it within magazine 75 is delivered for entry into a compartment 53 in turntable 11 (See FIGS. 19, 22 and 23).

Slot 92 is closed or opened by movement of a flush-mounted ram 93 slidably guided within it. Ram 93 is transversely guided within base 81 for movement along slot 92. It moves between an extended inner position, an outer position, and a cuvette inserting position.

Figure 22:
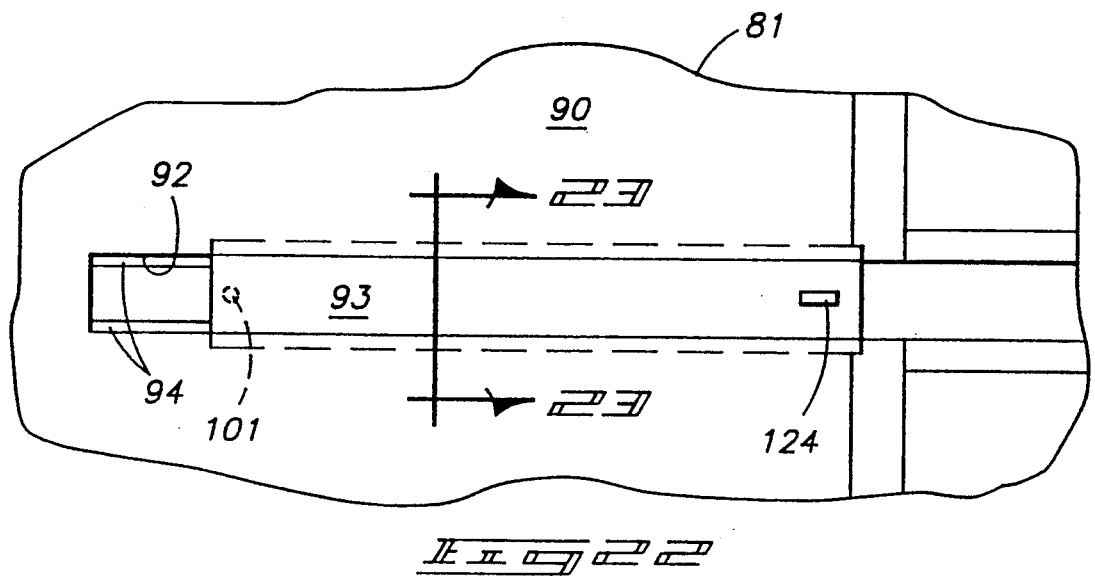
FIG. 22 is an enlarged fragmentary view taken along the cuvette-receiving slot as seen along line 22—22 in FIG. 19.
Figure 23:
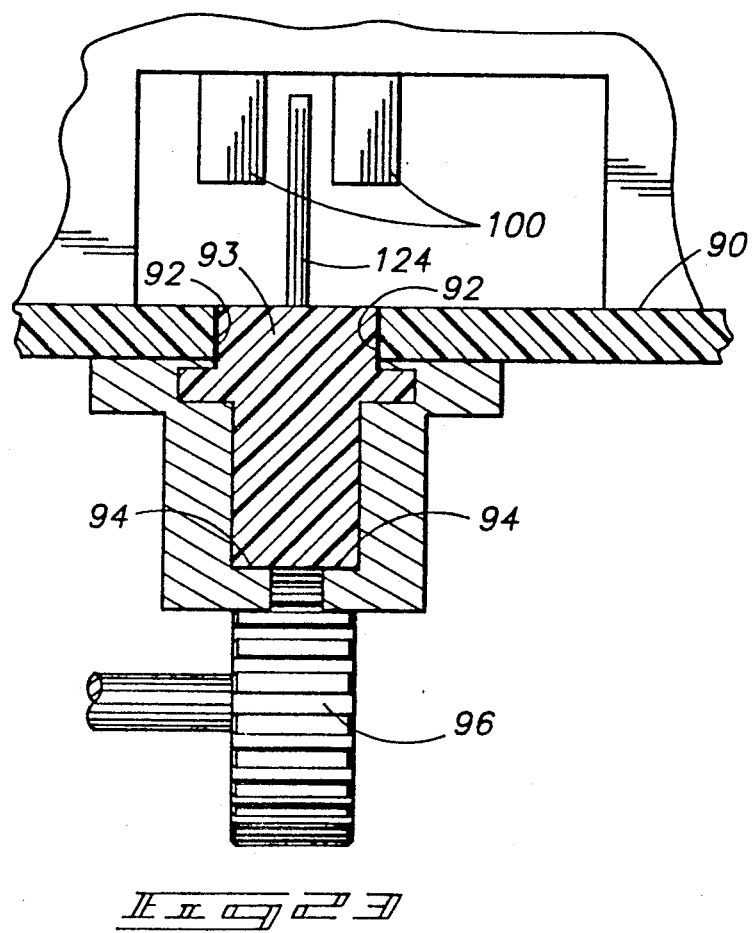
FIG. 23 is a sectional view taken along line 23—23 in FIG. 22.
Figure 24:
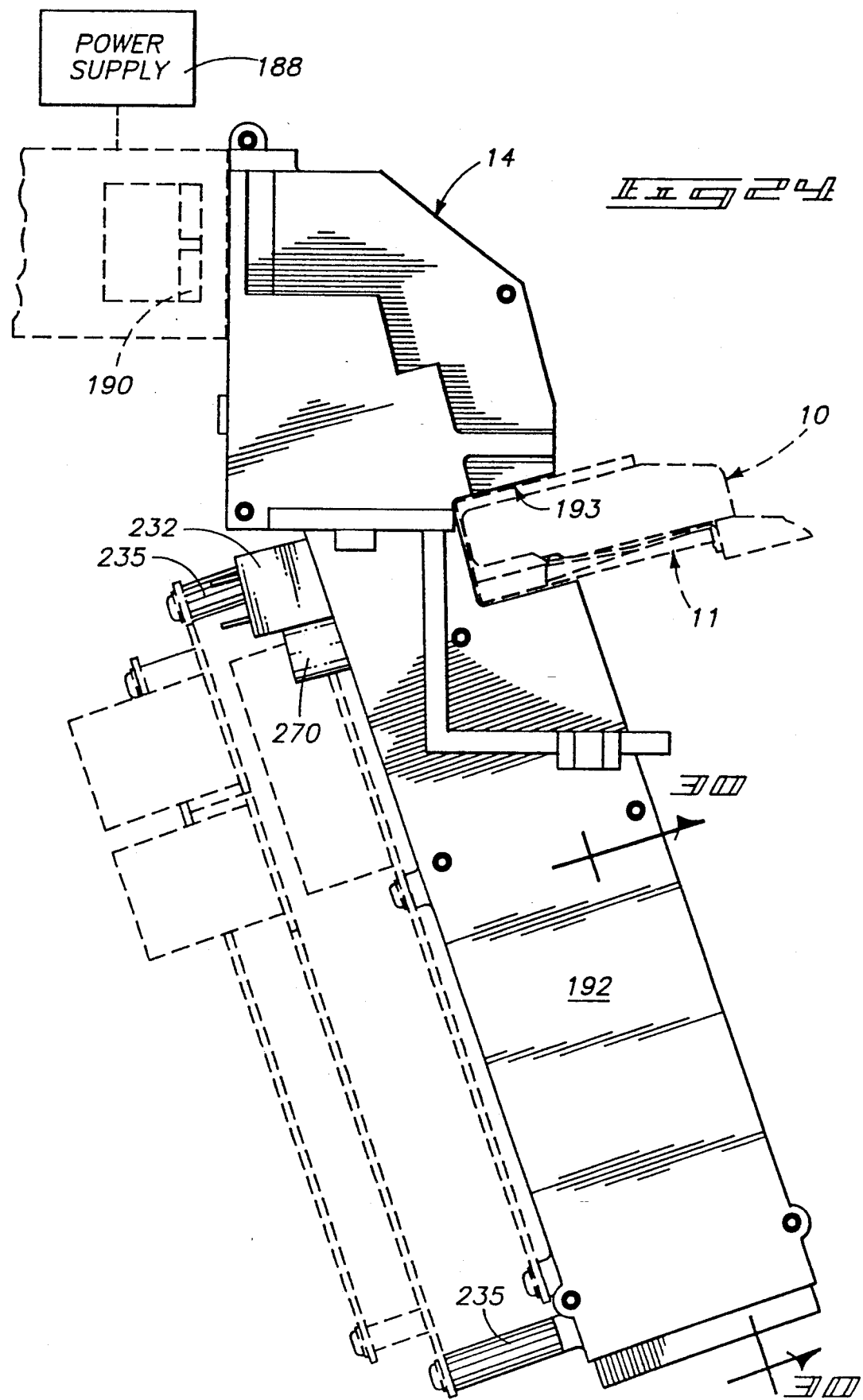
FIG. 24 is a side elevation view of the optical system enclosure.

Incoming cuvettes 10 within slot 92 are vertically supported on opposed transverse ledges 94 within the open slot 92 (FIGS. 22, 23). They can then be pushed into an indexed compartment 53 on the turntable 11 by reciprocation of ram 93.

The ram 93 is illustrated in FIG. 19 at a position where it partially closes the opening presented by slot 92 and is pushing a cuvette 10 into a turntable compartment 53. Ram 93 also is movable inwardly along the empty slot 92 before it allows a cuvette 10 to drop within slot 92, to cause a pin 101 at its underside to wedge between paired tapered guide surfaces 57 on turntable 11. This mechanically indexes turntable about axis X—X for subsequent accurate reception of a cuvette 10 within compartment 53. The retracted position of ram 93 leaves slot 92 fully open to receive cuvette 10 within it.

Figure 15:
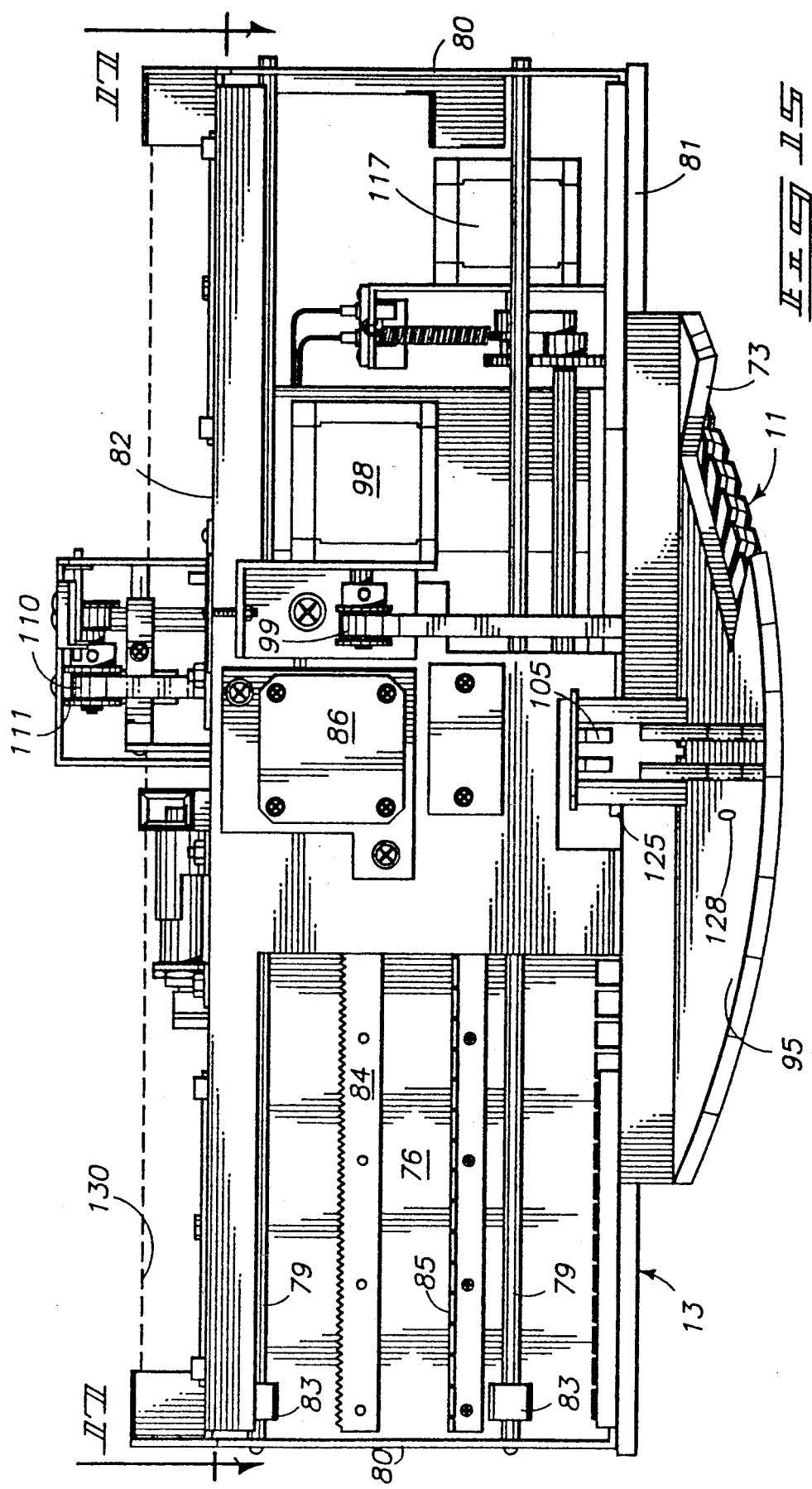
FIG. 15 is a front elevation view taken parallel to the side wall of the delivery module.
Figure 20:
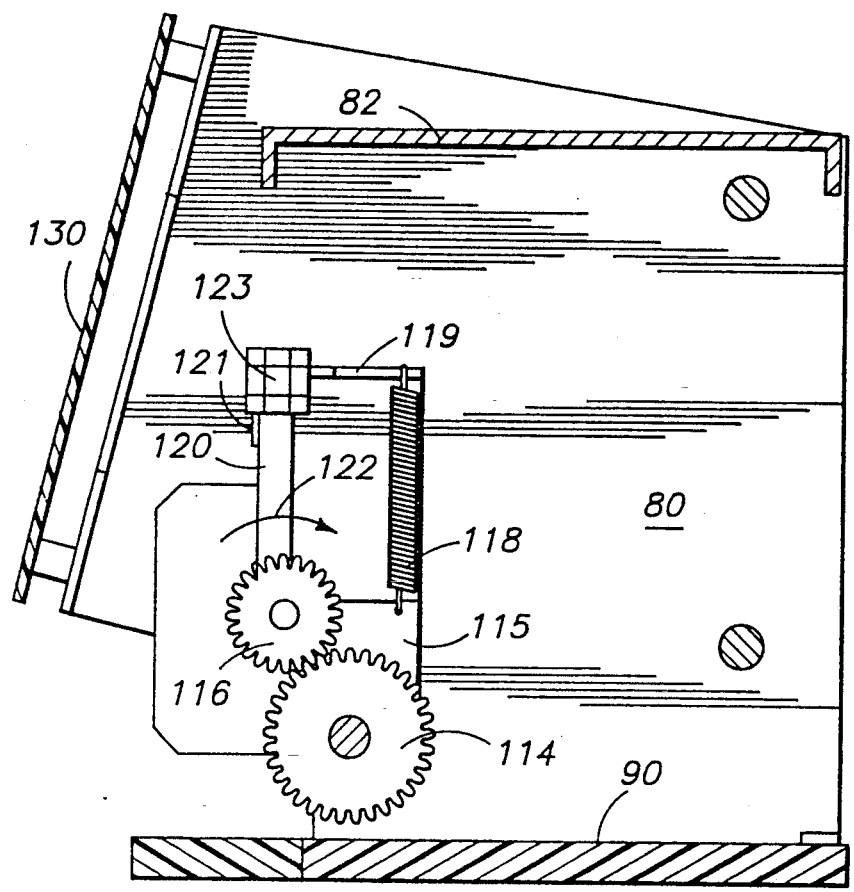
FIG. 20 is a transverse sectional view taken along line 20—20 in FIG. 17.
Figure 21:
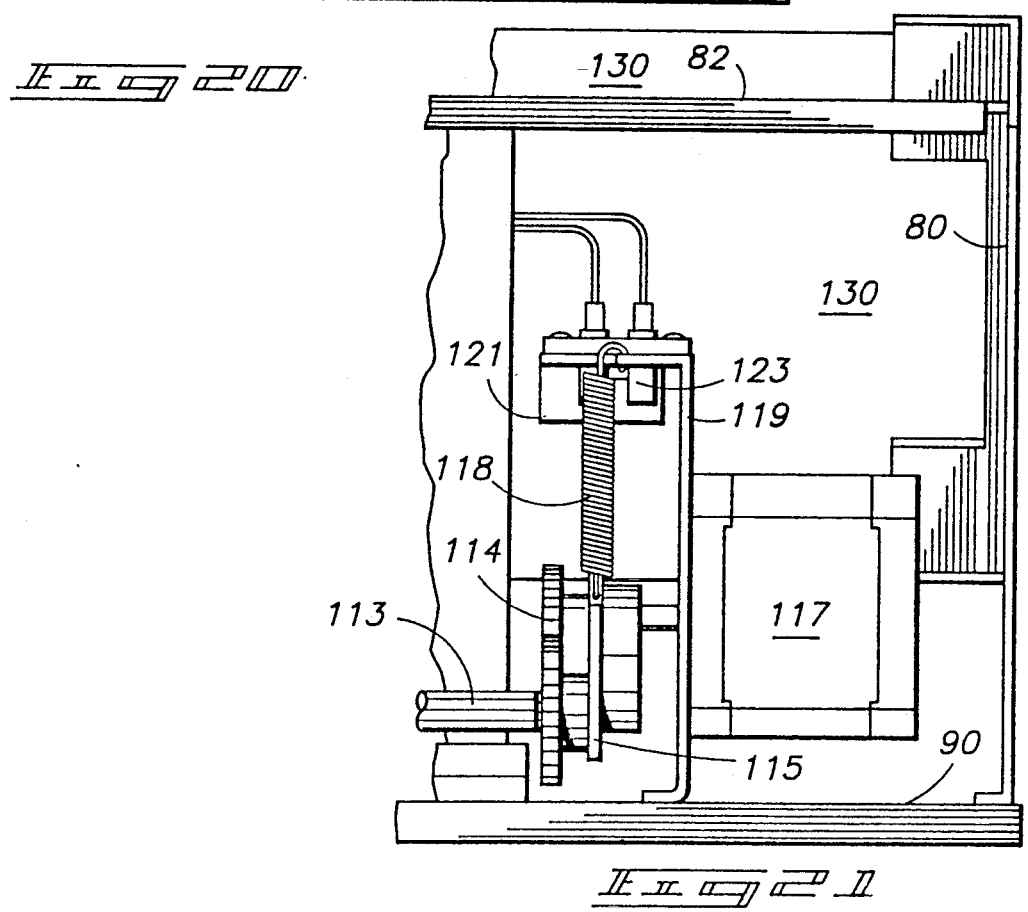
FIG. 21 is a side view of the elements shown in FIG. 20.

The ram 93 is powered by a rotatable gear 96 that meshes with a downwardly facing rack 97 formed along the bottom of ram 93 (FIGS. 19 and 23). Gear 96 is powered by a motor 98 on side plate 88 through interconnecting pulleys and a timing belt 99 as shown in FIG. 15.

Three limits of motion of ram 93 are detected by light sensors 100, 104 and 105, respectively, which detect the position of an upwardly protruding tab 124 at the outer end of ram 93. Associated electronic components for the photocells are mounted on a circuitboard 58.

The normal inoperative position of ram 93 is set with tab 124 at intermediate sensor 104. The sequence of movement by ram 93 involves three distinct phases.

After turntable 11 has been angularly indexed by motor 12 to receive a cuvette 11, ram 93 is moved inwardly from the position shown in FIG. 22 until tab 124 is detected by sensor 100. This causes pin 101 to wedge between a pair of tapered guide surfaces 57 to assure that a turntable compartment 53 is accurately aligned with the ram 93 for reception of a cuvette 10.

Ram 93 next fully retracts until tab 124 is detected by sensor 105. This allows a waiting cuvette to fall through the open slot 92 and rest on ledges 94.

Ram 93 then moves inwardly until tab 124 is again detected by sensor 100, thus inserting a new cuvette into the compartment 53 and causing the incoming cuvette to simultaneously eject the preceding cuvette from the turntable compartment. The downward motion of each stack of cuvettes 10 is monitored by a vertically movable follower 107, described in detail below.

Each end of the complementary cuvette cartridges 40 holds a complete stack of cuvettes. The inventory system for the magazine 75 is based upon a manual loading protocol whereby individual stacks of cuvettes 10 are to be replenished only after they have been totally depleted.

Figure 2:
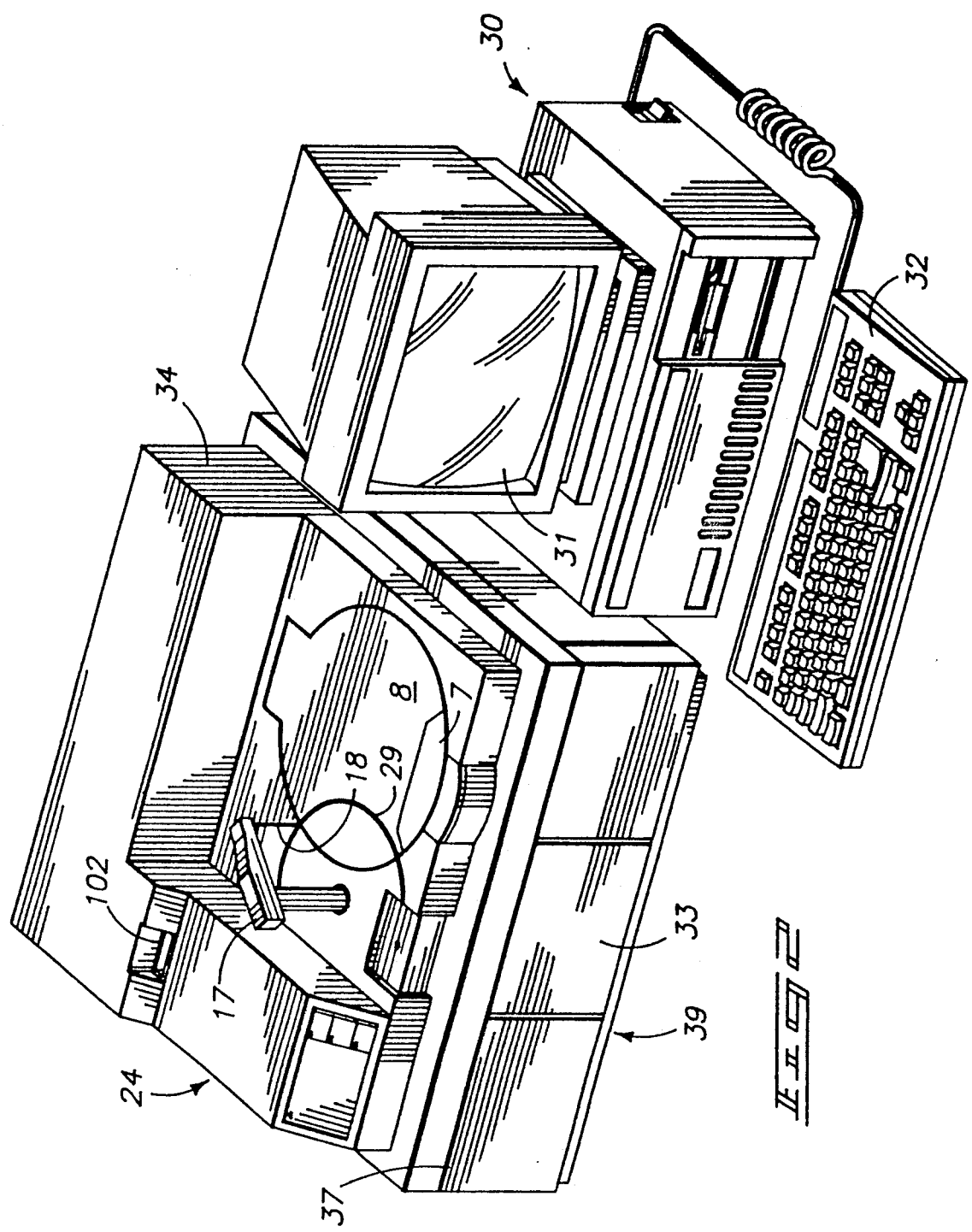
FIG. 2 is a perspective view of the analyzer.

One end of a cuvette cartridge 40 can be manually inserted into the cuvette delivery module 13 through a slotted guide 102 formed through the enclosure cover 34 (see FIGS. 2 and 3). The guide 102 is transversely intersected by a solenoid-controlled stripper 103 shown in FIG. 14 that blocks entrance of cuvettes until they are required. Retraction of the normally-extended stripper 103 is enabled only when a photocell assembly 126 trained through a slot in guide 102 detects the presence of a cuvette cartridge 40.

Actual retraction of stripper 103 is controlled by software instructions from workstation 30, which is programmed to permit refilling of magazine 75 only when a magazine slot under the guide 102 is empty. Retraction of stripper 103 is verified by a photocell assembly 127 mounted on top wall assembly 82, which straddles an extension pin 106 integral with stripper 103.

The elevation of photocell assembly 126 is lower than that of the stripper 103. Thus, the incoming end of cartridge 40 cannot pass the stripper and operate photocell assembly 104 if it is facing improperly within the slotted guide 102. Its lower edge will first abut the upper surface of stripper 103. This provides a mechanical interlock to assure that cartridge 40 and cuvettes 10 within it are not inserted into magazine 75 in a backwardly-facing orientation.

If oriented properly within the slotted guide 102, an incoming cuvette cartridge 40 can be manually pushed through the aligned slot within magazine 75 until its lower end abuts the planar upper surface 90. A photocell sensor 125 directed across surface 90 then detects the fully inserted position of the cartridge 40 and causes the stripper 103 to be extended to its normal position across guide 102. The shaft of stripper 103 then fits between the open legs of the cuvette cartridge 40 in the area between its center stops 42.

Cartridge 40 is removed from within magazine 75 by manually lifting it. The extended end of stripper 103 intersects the location of cuvettes 10 within the legs of the C-shaped channel 41 and prevents their upward movement, thereby causing them to remain in a stacked arrangement within the selected vertical slot of the receiving magazine 75.

Inventorying of cuvettes by workstation 30 is based upon an assumption that a full stack of cuvettes 10 will be supplied to magazine 75 during each loading sequence. The controlling software can maintain information as to the slots within the magazine 75 that contain full stacks of cuvettes 10. It is therefore necessary only to monitor the partial stack of cuvettes being delivered to the turntable 11 during current use of the chemistry instrument 24 and to physically measure the height of each stack of cuvettes within magazine 75 at machine startup to provide complete inventory information at all times. These functions are accomplished by a vertically movable follower 107.

The follower 107 is slidably guided by a supporting bracket 108 fitted about two upright rods 109. This support arrangement for follower 107 is best seen in FIG. 16. Follower 107 can be moved vertically between a normal elevated position clear of magazine 75, as shown in dashed lines at the top of FIG. 19, and a lowered position at which it rests upon the uppermost cuvette 10 in a selected stack within magazine 75.

Follower 107 and bracket 108 are moved vertically by means of a timing belt 110. Bracket 108 is clamped to one flight of the belt 110, which is entrained over upper and lower pulleys 111, 112. follower 107 remains in a horizontal position at all times, thereby resisting any tendency of the stacked cuvettes 10 beneath it to assume an angular orientation within the confining walls of the magazine 75.

Engagement of follower 107 with the uppermost cuvette 10 in a stack is detected by the resulting torsional forces exerted on pulley 112 through interconnecting belt 110. Pulley 112 is mounted to an extended shaft 113 leading to a gear 114 at the opposite end of shaft 113 (see FIGS. 17, 20 and 21). Gear 114 is rotatably supported on a bracket 115, which in turn is pivotally supported about the axis of a meshing gear 116 powered directly by a driving stepper motor 117.

Bracket 115 is biased to a normal position wherein the axis of shaft 113 is parallel to the axis of driving gear 116. The biasing forces on bracket 115 are provided by a tension spring 118 connected between bracket 115 and a fixed plate 119 which mounts the motor 117. In this normal position, an extension arm 120 that is integral with bracket 115 abuts a side ledge 121 on the plate 119. However, when follower 107 engages a cuvette at the top of a stack, the resulting torsional forces on gear 114 will cause the bracket 115 to pivot slightly in the direction shown by arrow 122 in FIG. 20. This torsional movement can be detected by a photocell sensor 123 that straddles arm 120. Sensor 123 is fixed to plate 119.

A printed circuitboard 130 is provided across the remaining side of the cuvette delivery module 13 and mounts the electronic components associated with it. The details of the printed circuitboard 130 are not shown. It is to be understood that the electronic controls for the various motors, sensors, and solenoids will be interconnected in the usual manner so as to perform the functions of the module as described herein.

Optical Test System

FIGS. 24–30 illustrate the physical arrangement of the components that make up optical system 14, which is located directly adjacent to turntable 11. FIG. 31 is a diagrammatic view showing the light paths involved in providing electronic measurement of absorbance as a function of light transmitted through the test samples in the individual rotating cuvettes 10 or fluorescence polarization as a function of emissions produced by test samples within individual cuvettes 10 in response to light excitation.

Figure 25:
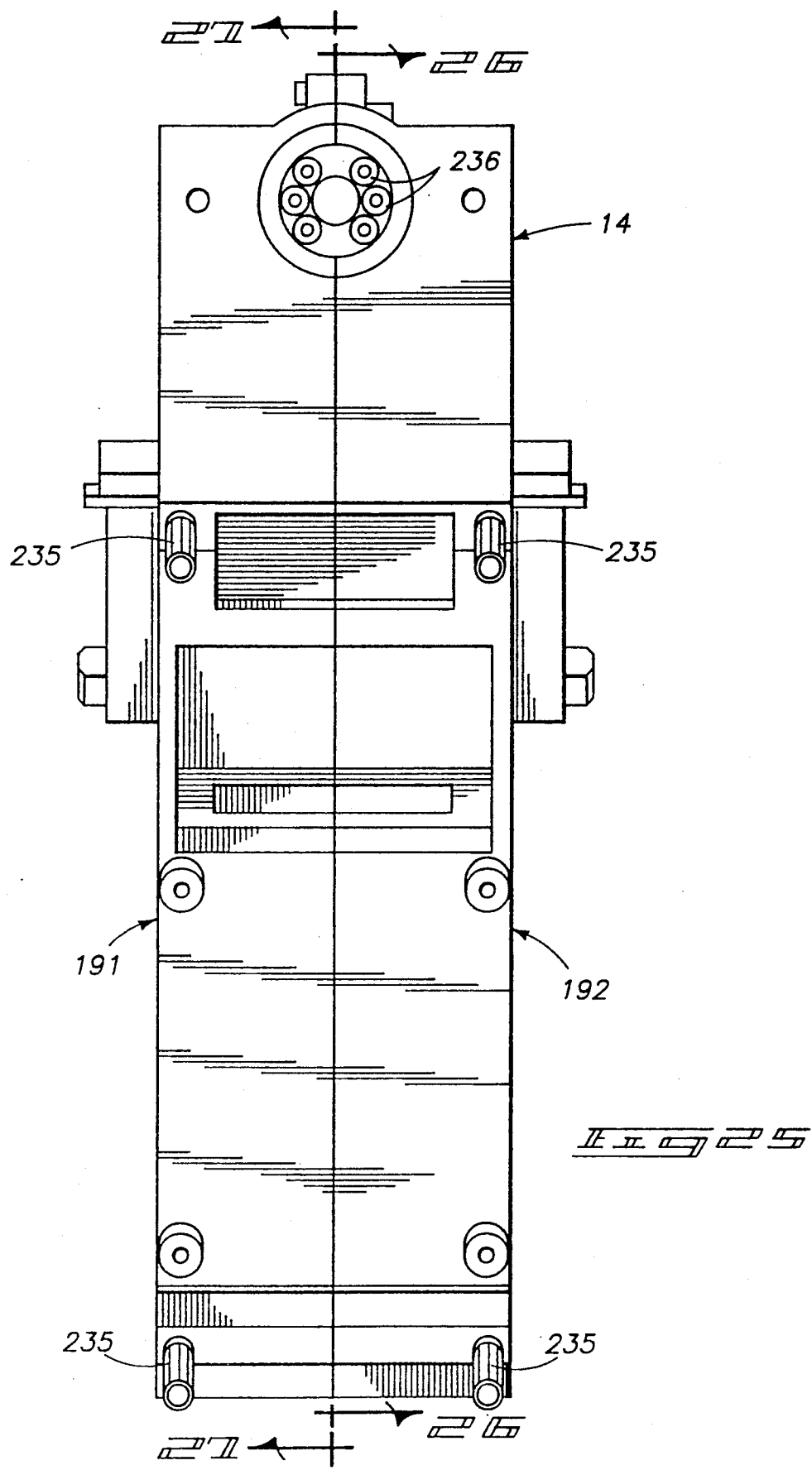
FIG. 25 is a front view of the enclosure as viewed from the left in FIG. 24.
Figure 26:
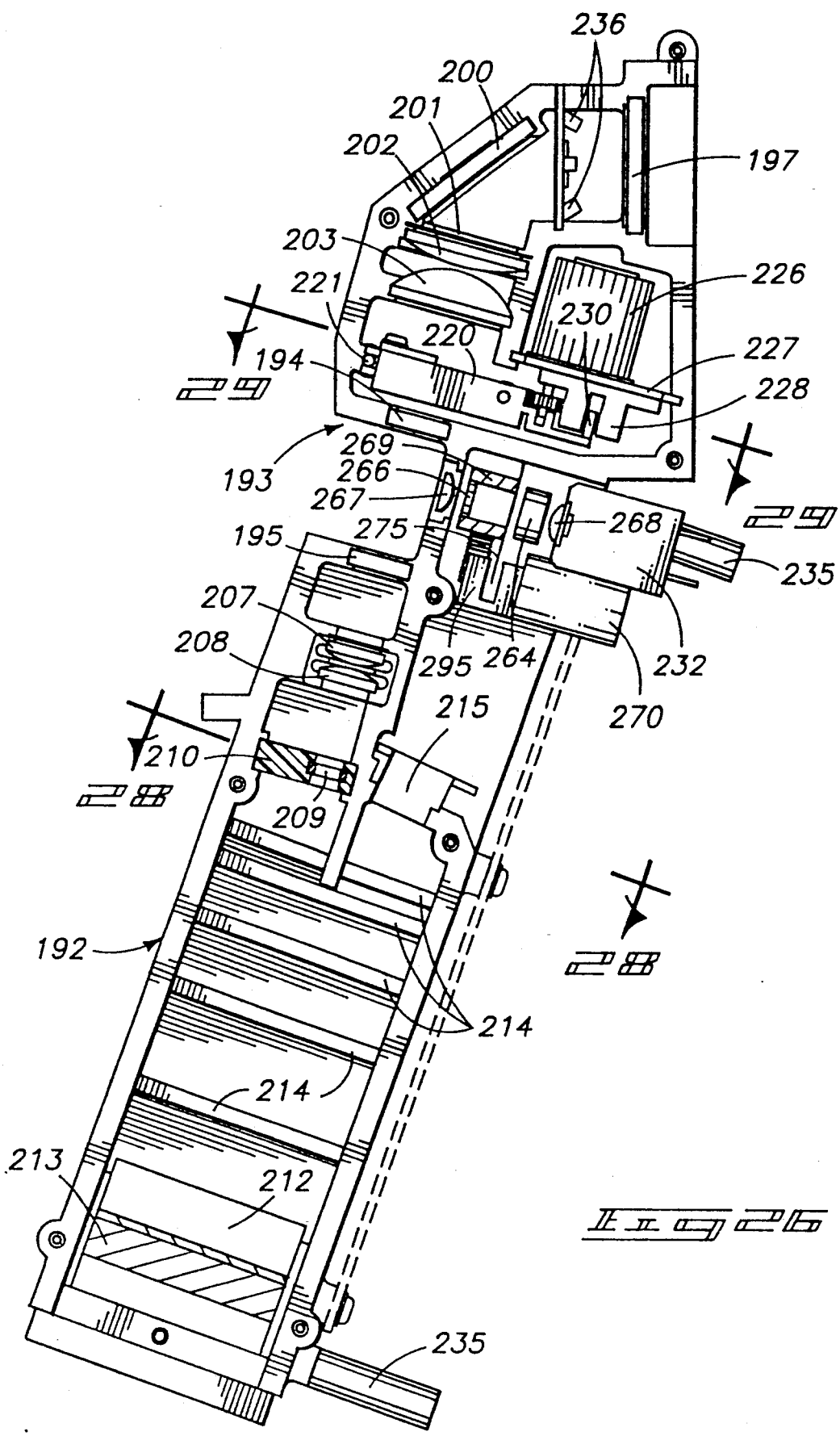
FIG. 26 is a sectional view of the right hand side of the optical system module as seen along line 26—26 in FIG. 25.
Figure 27:
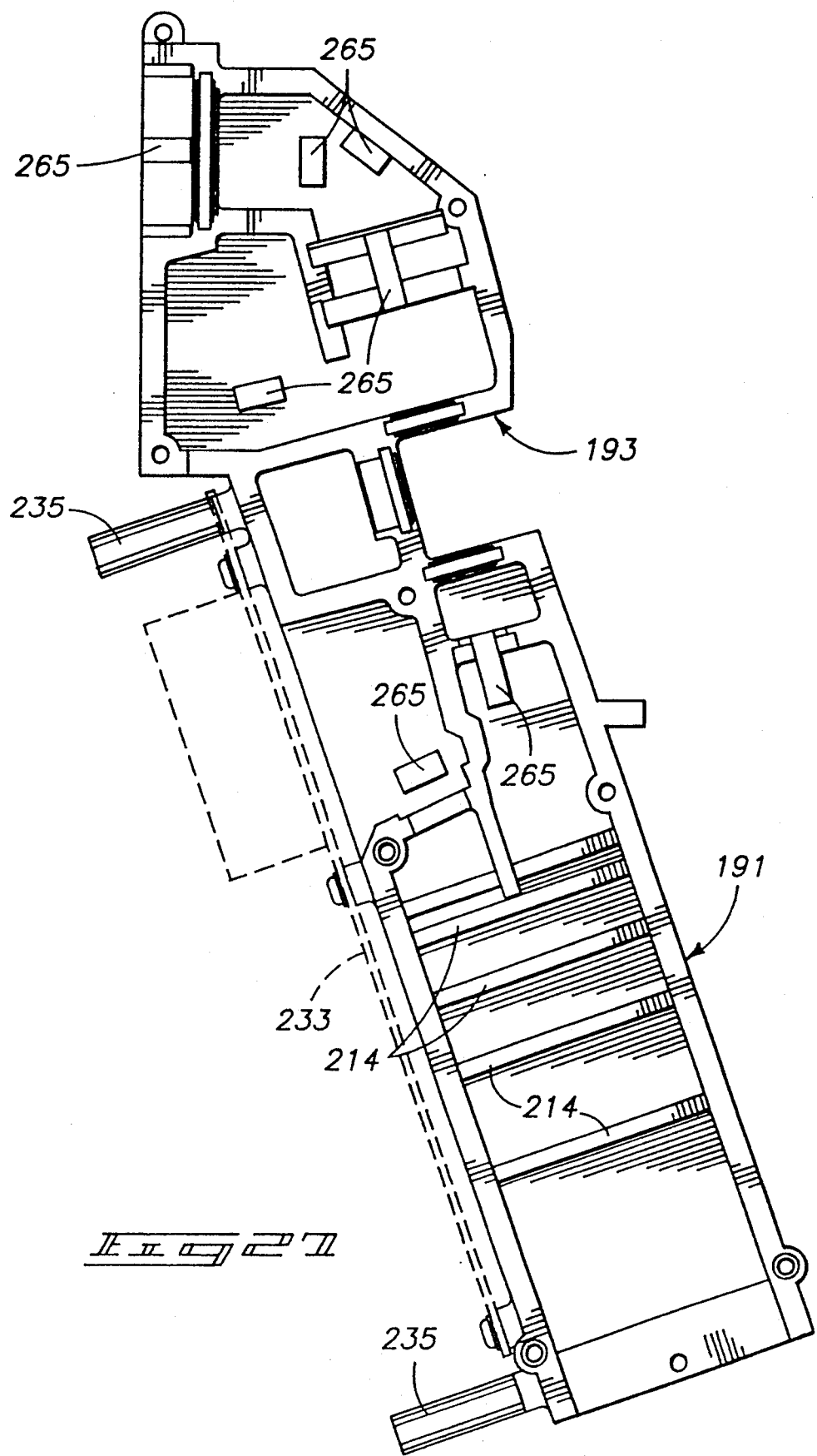
FIG. 27 is a sectional view of the left hand side of the optical system module as seen along line 27—27 in FIG. 25.

The optical system is located within a molded light-proof enclosure assembled from complementary left and right compartments 191 and 192, as shown in FIG. 25. The interiors of compartments 191 and 192 are illustrated in FIGS. 26 and 27, respectively.

Figure 4:
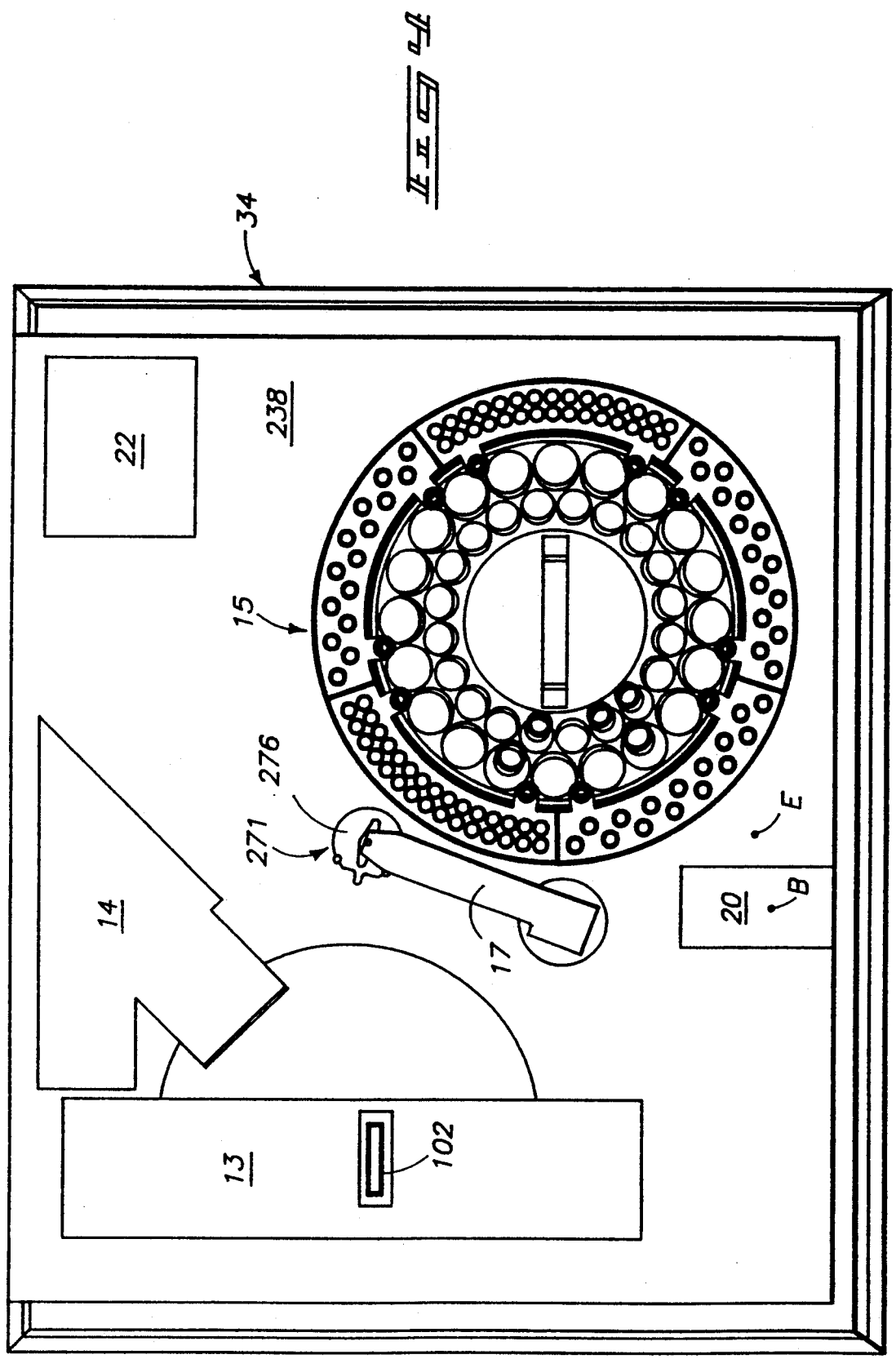
FIG. 4 is a plan view of the chemical instrument enclosure with the cover removed.
Figure 5:
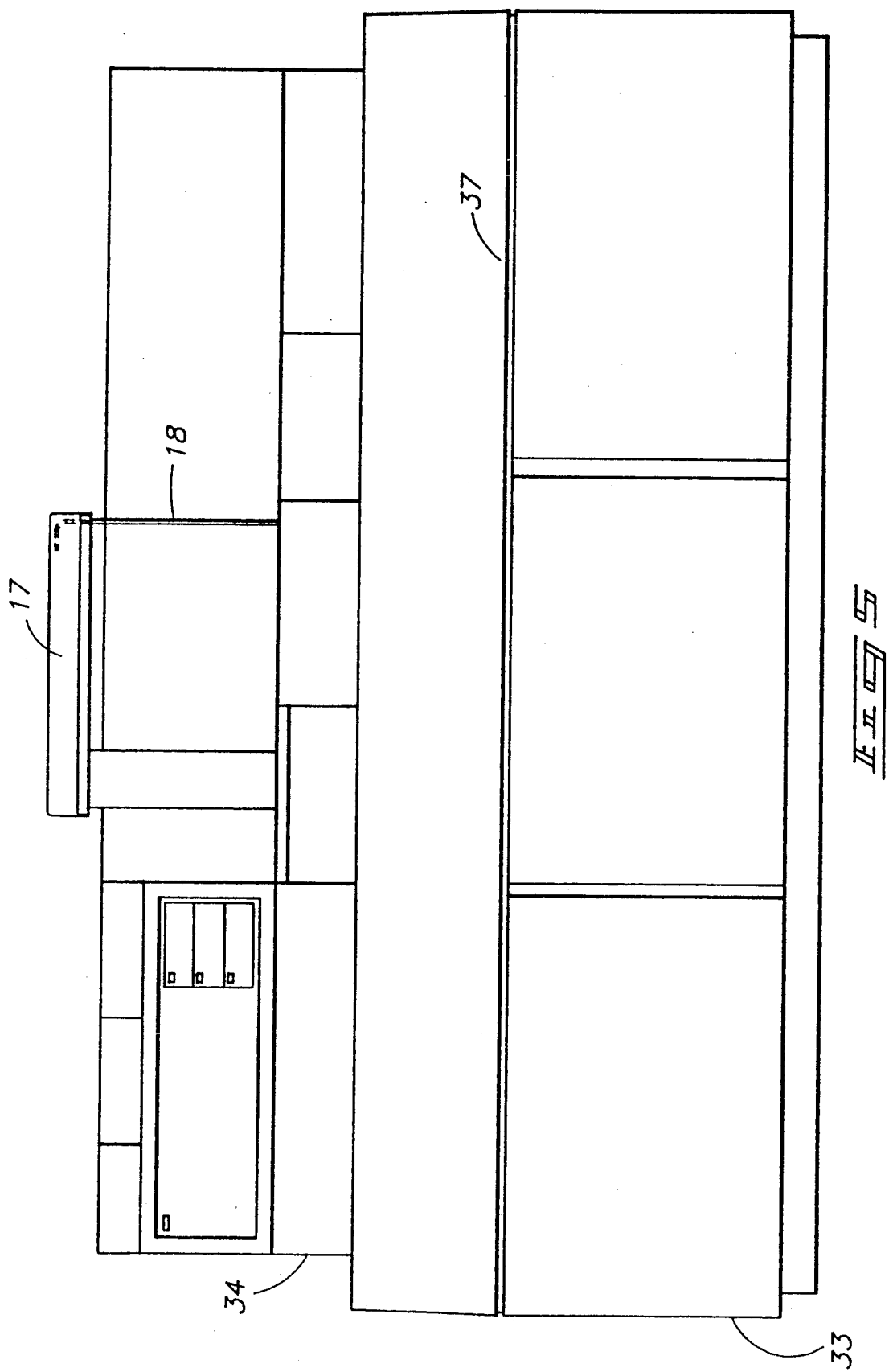
FIG. 5 is a front elevation view of the enclosure.

The exterior of the enclosure includes a transverse recess 193 that extends fully across the widths of the two joined compartments 191, 192. The outer periphery of turntable 11 is positioned to rotate through recess 193. The position of turntable 11 with respect to the optical system 14 is generally shown in FIG. 4 and is more specifically illustrated in dashed lines in FIG. 24.

The inclined orientation of recess 193 complements the inclined arrangement of the cuvettes 10 about the periphery of turntable 11. Recess 193 within the optical system enclosure overlaps the previously-described slots 54 in turntable 11 which provide exterior exposure to optical surfaces 48, 49 and 50 at the lower end of each cuvette 10.

Recess 193 is provided with an upper light window 194, an opposed lower light window 195 and an end light-collecting lens 267. Windows 194 and 195 permit transmission of light through the upper and lower optical surfaces 48, 50 of each cuvette 10 for absorbance tests. Lens 267 collects fluorescent light emissions from within each cuvette 10 through its end optical surface 49.

A conventional pulsed Xenon lamp 190 is used in the optical system 14 as an intermittent high intensity light source for both absorbance and fluorescence polarization testing purposes. Its excitation is timed to coincide with the time of passage of each cuvette 10 through the recess 193. A lamp power supply 188, also of conventional design, is included in the chemistry instrument 24 to provide required electrical power to the lamp 190.

For illustrative purposes, FIGS. 26 and 27 show the optical elements (primarily lenses and filters) within compartment 192 only. They are located along the parting line separating the two compartments and actually project transversely into both compartments.

The right compartment 192 is illustrated in the disassembled view shown at FIG. 26. Each optical element is accurately positioned within the enclosure by engagement against a complementary control surface presented within compartment 192. The molded control surfaces, that complement the peripheral exterior of the respective optical elements, locate them along the length of the light path leading from lamp 190. Each lens is axially biased against the engaged control surfaces by surrounding flexible tubing, which is slightly compressed behind the lens to assure its proper positioning within the enclosure.

Left compartment 191 shown in FIG. 27, includes complementary recesses and mountings for these elements, which are situated along the tongue and groove seal between the two compartments 191, 192. The mountings include resilient foam pads 265 which transversely engage the optical elements. The pads 265 within compartment 191 serve as complementary retaining surfaces that act in structural opposition to the control surfaces within compartment 192 for maintaining the optical elements in a centered position across the parting line when the two compartments are assembled.

The optical system will be described first with respect to the absorbance subsystem used for detecting transmission of different light wavelengths during analysis of reaction mixtures within cuvettes 10.

Light pulses from lamp 190 pass through a circular window 197. The resulting light path is surrounded by a ring of reference diodes 236 that measures incoming light intensity. The path of the light entering the optical system enclosure is then turned by a diagonally placed mirror 200. This first light path leads to a first detector 215 for monitoring the intensity of light absorbed by a test sample within a cuvette 10 in response to light passing along the first light path through the pair of optical surfaces 48, 50 at the top and bottom of the cuvette.

Light from lamp 190 is initially focused across the center plane of each cuvette 10 located within recess 193 by two plano-convex lenses 202 and 203 provided in the upper optics module shown in FIG. 26. A large lens aperture 201 is located directly adjacent to lens 202 and restricts the passage of light to a defined circular aperture area.

Light passing through the cuvettes 10 within recess 193 is again focused at a transverse slit aperture 209. The required focusing is accomplished by use of paired plano-convex lenses 207 and 208 in the lower optics module shown in FIG. 26.

Figure 28:
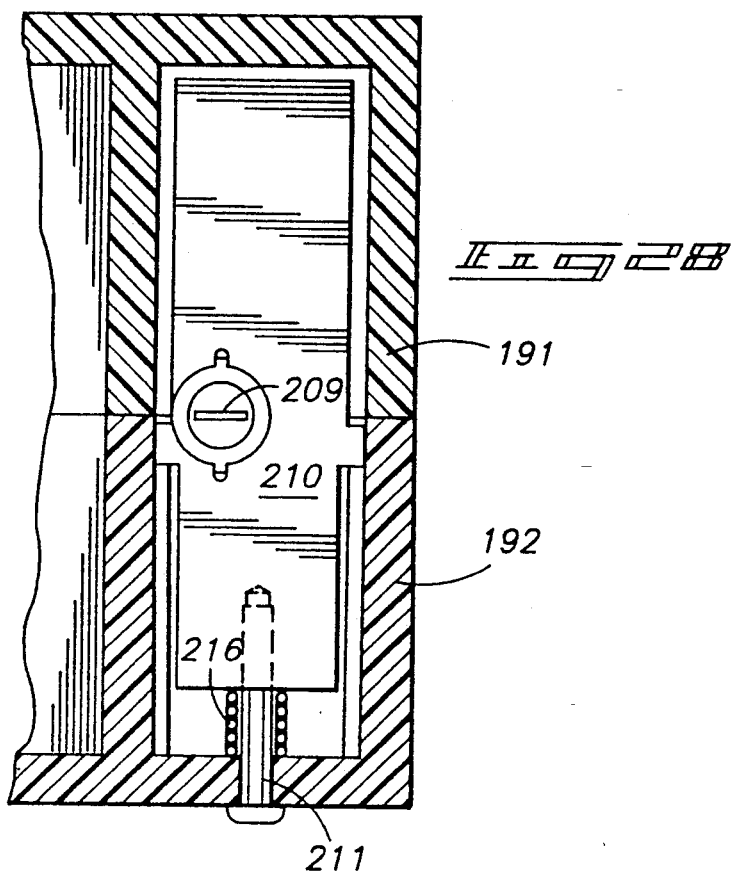
FIG. 28 is an enlarged fragmentary sectional view taken along line 28—28 in FIG. 26.

Details of the mounting arrangement for slit aperture 209 are shown in FIG. 28. The slit aperture 209 is mounted within a supporting block 210 slidably carried within the enclosure for adjustment in a direction perpendicular to the length of the slit aperture 209. Adjustment of block 210 is accomplished through a screw 211 acting in opposition to a surrounding compression spring 216.

The narrow, focused beam of light that passes through slit aperture 209 is directed to a holographic grating 212 supported on a mounting block 213 within the interior of the enclosure. The holographic grating 212 is positioned at an angle to the axis of the light beam (see FIG. 30) to direct resulting component light wavelengths onto a photo diode array 215 capable of spatially detecting the intensities of light at a plurality of discrete wave lengths. The photo diode array 215 comprises a linear pattern of light-receiving diodes arranged across the enclosure at the locations where the monitored wavelengths will be diffracted by holographic grating 212.

Figure 30:
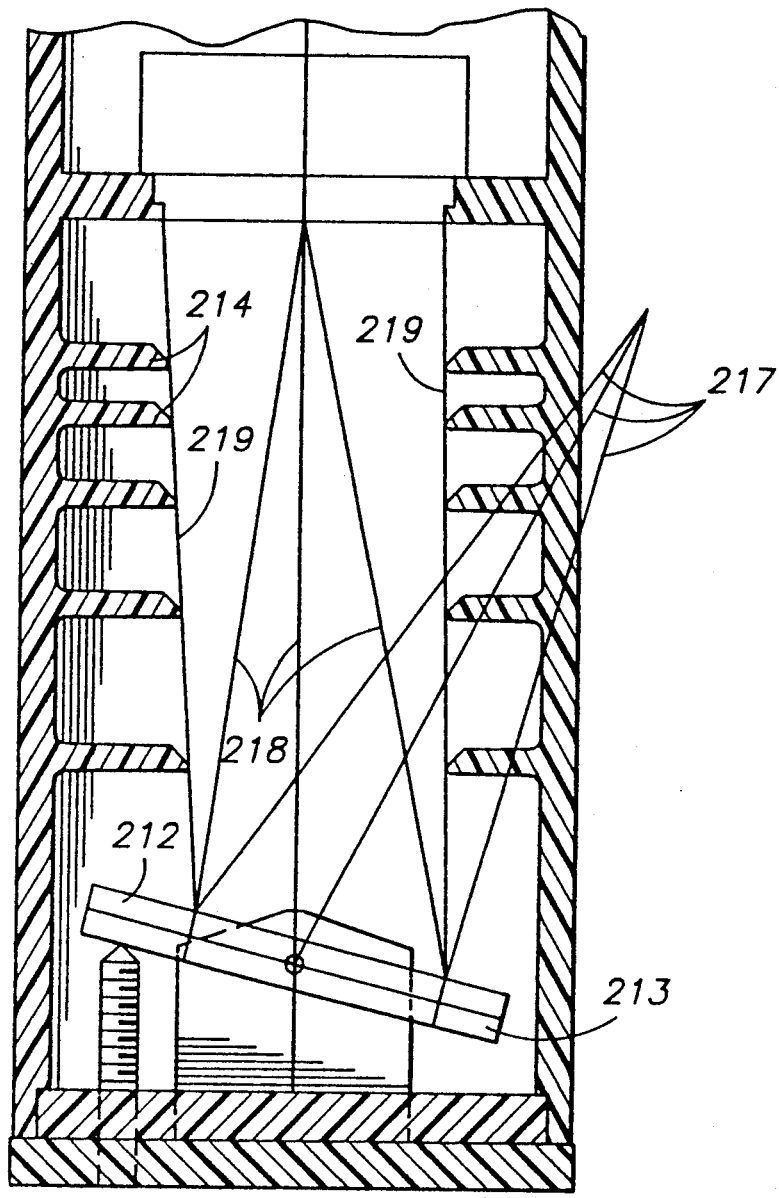
FIG. 30 is an enlarged sectional view taken along line 30—30 in FIG. 24.
Figure 31:
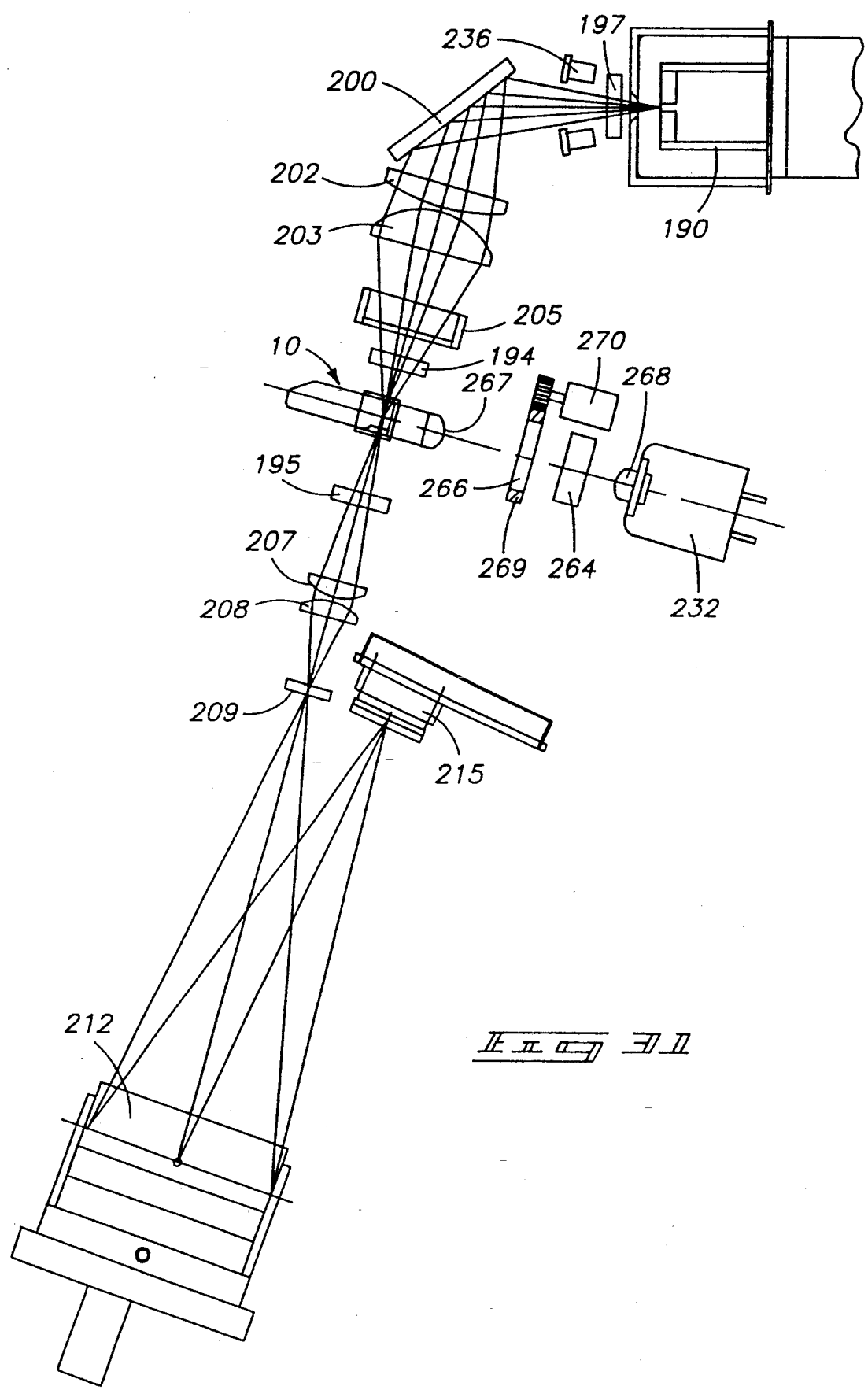
FIG. 31 is a diagrammatic view illustrating operation of the optical system.

Transverse baffles 214 are provided across the inner walls of the enclosure compartments 191, 192 to capture white light reflected by holographic grating 212, as generally indicated by lines 217 in FIG. 30. Lines 218 in FIG. 30 illustrate the beam of incoming light directed to the holographic grating 212. Lines 219, bounded by the baffles 214, indicate the width of the reflected beam directed onto the photo diode array 215.

Fluorescence polarization is monitored by use of a second detector aligned along a second light path perpendicular to the first light path and adapted to perpendicularly intersect the third or end optical surface 49 of a cuvette.

To measure fluorescence polarization that results from light excitation of the cuvette contents, a fluorescence excitation filter 205 with a polarized film mounted before it must be inserted between lamp 190 and the cuvettes 10 in turntable 11. The mounting of filter 205 within the optical system enclosure is detailed in FIG. 29.

Filter 205 is carried within a movable plate 220 guided by fixed rods 221. The rods 221 are respectively received within aligned apertures 222 formed through plate 220 and paired guides 223 that project laterally at one of its side edges. The position of plate 220 within the enclosure is controlled by a rack 224 formed on it, which is engaged by a driving gear 225. Gear 225 is powered by a motor 226 located within the enclosure.

The operation of motor 226 is controlled by electronic devices on a printed circuitboard 227. These devices include upper and lower optical cells 228, 229 that respectively detect the position of upper and lower tabs 230, 231 formed as projections from the plate 220.

Figure 29:
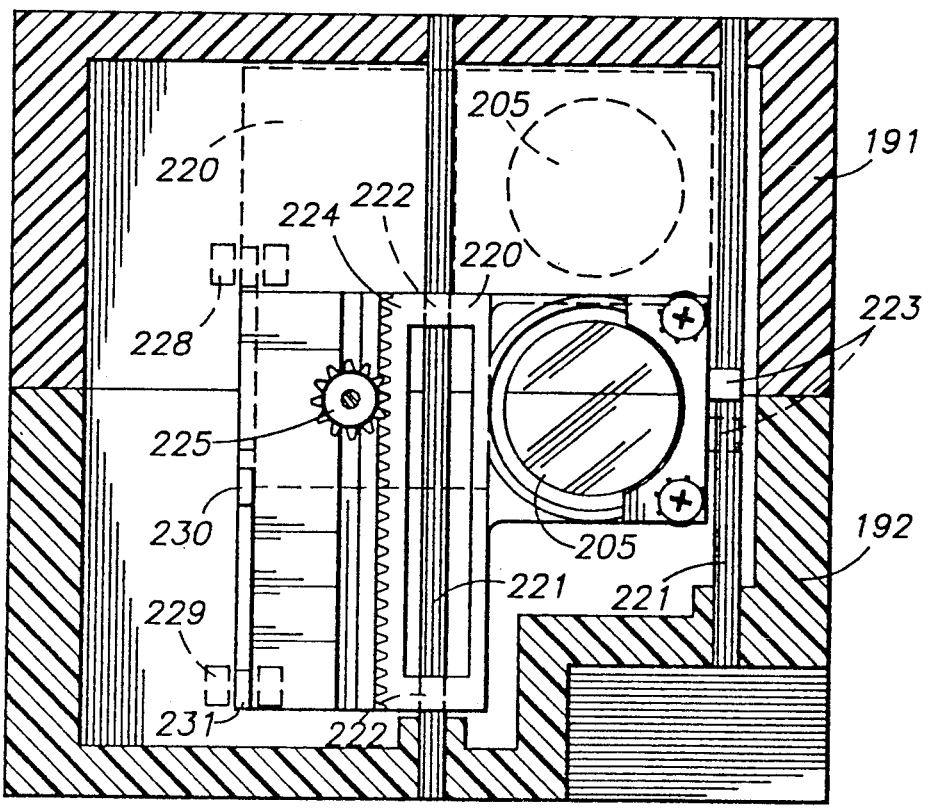
FIG. 29 is an enlarged fragmentary sectional view taken along line 29—29 in FIG. 26.

The two positions of plate 220 are shown in FIG. 29. Its lower position, situated in the light path passing through the enclosure, is used for fluorescence polarization testing purposes. Its raised position (shown in dashed lines) is utilized to remove the excitation filter 205 from within the direct light path through a cuvette 10 during absorbance tests.

The monitoring of fluorescence polarization requires measurement of emitted fluorescence at two different orientations. This can be effectively accomplished by use of the well-known arrangement of passing the fluoresced light through a polarizer to a detector and measuring one component, and then rotating the polarizer 90° and measuring the second component.

As shown in FIGS. 26 and 31, the apparatus used for monitoring intensity of fluorescence polarization includes a rotatable polarizer 266 and a fluorescence emission filter 264 coaxially aligned along a second light path leading to a receiving photo-multiplier tube 232 that produces a signal indicative of the intensity of the received fluorescence at each of the selected angular orientations. Conventional lenses 267 and 268 intensify and focus the emitted light passing through the polarizer 266 and filter 264.

The polarizer 266 is held within a supporting rotatable drum 269 having an external gear driven by a motor 270. Idler gears can be interposed between the motor 270 and the exterior of drum 269 as required.

Drum 269 is turned about its axis between two angular stops that physically limit its rotation to 90°. As one example, the drum 269 might be slotted about 90° of its periphery and a pin projecting into the slot would define the limits of its rotational motion about its central longitudinal axis. The rotational position of drum 269 is monitored by means of a timing disk 275 projecting radially outward from it. The periphery of disk 275 passes between sensors 295 (FIG. 26) to provide electrical signals as a function of the angular position of disk 275 and drum 269.

The components used for monitoring of fluorescence polarization are housed within a separate module removable from the exterior of the assembled enclosure. The exterior of the enclosure also includes support posts 235 for additional printed circuitboards (FIG. 24) that mount electronic devices associated with the optical analyzing system.

FIG. 31 graphically illustrates the path of light through the optical system. The single unit can be readily converted from an absorbance system to a fluorescence polarization system by operation of motor 226 to either place the excitation filter 205 within or outside the light beam pulsed into the enclosure by operation of lamp 190. In operation, it is anticipated that both absorbance and fluorescence polarization readings will be taken of samples within selected cuvettes 10 in the turntable 11 during each of its operational cycles. The actual nature of the tests conducted will depend upon the analytical results required by any particular tests being carried out during each turntable cycle.

ISE Module

The electrolyte system illustrated by the Ion Specific Electrode (ISE) module 38 (FIG. 1) is a conventional component supplied by other manufacturers for potentiometric testing purposes. Sample liquid is delivered to the ISE module 38 by operation of pipette 18, which is insertable into module 38 through an open entry aperture shown at 9. Its operation in detecting the quantity of pre-selected electrolytes within a sample is well known to those skilled in this field and requires no further explanation.

Sample/Reagent Tray

FIG. 4 illustrates the positional relationship between the sample/reagent tray 15 and the primary components of the chemistry instrument 24 located about the intermediate horizontal platform 238 included within the enclosure for the chemistry instrument 24. Details of sample/reagent tray 15 are illustrated in FIGS. 32-36.

FIG. 36 illustrates an area of platform 238 forming a recessed well 240 within which the tray 15 is rotatably mounted. Well 240 is centered about a fixed vertical support shaft 241 for the tray 15 and includes a surrounding rim 242. The cross-sectional relationships between these elements is best illustrated in the sectional view shown at FIG. 33.

The illustrated tray 15 is designed to supply reagents to the chemistry instrument 24 from at least two sizes of conventional reagent bottles 25. They are arranged within concentric rings. Additional sizes of bottles can be accommodated within the tray structure by using surrounding adapter sleeves (not shown) that fit properly within receiving tray apertures. Bottle labels read by scanners provide bottle size information and reagent identification data (regent type, lot number and bottle serial number) to the chemistry instrument as needed for monitoring of reagent inventory and life.

The upper end of each reagent bottle 25 is normally covered by a removable threaded cap (not shown) when manually delivered to the chemistry instrument 24. A "peel and stick" protective cover 239, made from a paper or plastic sheet, is utilized across each bottle 25 to prevent contamination and spillage during its usage in the tray 15. Each cover 239 is slit in an intersecting pattern to facilitate passage of pipette 18 through it while accessing reagent liquids.

The cylindrical reagent bottles 25 are tilted from vertical to permit the tip of pipette 18 to penetrate the interior of each bottle to a location adjacent to the lowermost inclined intersection between the container side and bottom walls. This assures more complete removal of liquid from within each reagent bottle 25.

The sample/reagent tray 15 is rotated about its central vertical axis by its engagement with a powered driving gear 244 (FIG. 36) that projects into well 240. Gear 244 meshes with peripheral gear teeth 243 formed about the exterior of tray 15. It is operatively powered by stepper motor 16 (FIG. 1).

The circular tray 15 is rotatably mounted on the framework for the chemistry instrument 24 for rotation about a central vertical axis parallel to the axis of the turntable 11. Tray 15 can be indexed to any desired angular position about its central axis by operation of stepper motor 16.

Typical configurations for the open reagent bottles 25 are illustrated in dashed lines in FIG. 33. As seen in FIGS. 32 and 33, the base of tray 15 includes two sets of apertures 132 and 133 suitably sized to receive and support at least two sizes of reagent bottles 25. The apertures also expose the bottom of each bottle 25 for optical viewing of bottom labels applied to the bottles. In a preferred form of a reagent identification system, circular labels having machine-readable indicia printed on their surfaces are scanned from below tray 15 while it is stationary, thus capturing encoded data pertaining to the bottle contents.

Tray 15 includes a central carrying handle 133. Handle 133 facilitates removal of the tray 15 and reagent bottles 25 as a unit, as well as any attached ring segments 26. A plurality of trays 15 can be interchanged in a chemistry instrument 24 as required for specific test purposes. The entire tray 15 can also be removed from the chemistry instrument 24 overnight and during periods of nonuse. It can then be stored in a refrigerated environment or under other conditions as required by the nature of reagents supplied in the tray.

A series of peripheral posts 134 releasably support separable circumferential ring segments 26. The ring segments 26 can be attached to tray 15 while it is located within the chemistry instrument 24 enclosure or at a loading station external to the illustrated equipment.

The individual ring segments 26 shown in FIGS. 32, 33 and 35 are either provided with integral molded wells 36 or removable cups 35. The ring segments 26 are otherwise structurally interchangeable. Each includes radial tabs 135 that fit over the supporting posts 134 when the ring segments 26 are assembled about the tray 15.

To distinguish the two types of ring segments 26, the outer depending flanges 253 on the cup ring segments are notched, as shown by notch 254 in FIG. 35. The nature of a particular ring segment 26 is determined by a light sensor 252 located on platform 238 immediately adjacent to rim 242. The outer upright flanges 253 about the ring segments 26 pass between the elements of the sensor 252. The relative positions of these elements is illustrated in dashed lines in the sectional view shown in FIG. 33.

Both cups 35 and wells 36 have identical interior volumes and shapes, the only physical difference between them being that the cups 35 are separable from a supporting ring segment 26, while the integral wells 36 are not. Cups 35 are less densely arranged about the ring segments 26 so as to provide adequate room about them to facilitate manual handling of the individual cups as needed.

The functions of cups 35 and wells 36 are designed to be complementary to one another. Cups 35 can be added to tray 15 individually or as part of a supporting ring segment 26. Wells 36 are always handled as a group. The portable cups 35 are available only to a human operator for introduction of sample, calibrator, and control liquids. Pipette 18 never delivers liquids to cups 35, but can deliver liquids available within cups 35 to cuvettes 10 in turntable 11 as required for assay purposes. Wells 36 are available only to the chemistry instrument 24. Pipette 18 can use available wells 36 for aliquoting of sample liquid, for dilution of samples before introduction to the ISE module 38, and for mixing of sample liquid with system diluent or a buffer supplied from a bottle 25 on the sample/reagent tray 15.

Manual access to the sample/reagent tray 15 is available through the hinged tray access cover 8 shown in FIGS. 2 and 3. Access to the individual ring segments 26 is provided by the segment access port 7. While mechanical interlocks can be provided to restrict opening of cover 8 and port 7, they are not essential. Sensors (not shown) are provided to detect their opening and to alert monitoring software residing in workstation 30 of such events.

Indexing of tray 15 is accomplished by a circular notched indexing ring 245 formed at its underside, which moves between an optical sensor 246 coupled to workstation 30. A reference "home" angular position of tray 15 about the vertical axis of shaft 241 is determined by a projecting index tab 247 at the bottom of tray 15, which is detected by an optical sensor 248 within well 240. The relative positions of these elements is also illustrated in dashed lines in FIG. 33.

A pair of optical scanner ports 250 are located in the base of well 240 directly under the two circular paths of reagent bottles 25 supported by tray 15. Scanning devices under the ports 250 are provided to read encoded end labels attached to each reagent bottle 25. Information on the labels, read through openings under each bottle 25, might relate to reagent identification, lot numbers and serial number.

A line-of-sight optical sensor 256 is arranged across rim 242 for sensing the presence of the removable cups 35 in the ring segments 26. The relative positions of these elements is also illustrated in dashed lines in the sectional view shown in FIG. 33. By combining tray indexing information, segment identification information and cup presence information together with liquid transfer data, workstation 30 can maintain an accurate inventory of the cups 35 and wells 36 available for use with respect to tests being conducted on the chemistry instrument 24.

A conductive metal plate 258 is fixed within well 240 under the circular paths of the reagent bottles 25. The upper surface of plate 258 is spaced from, but in close proximity to, the exposed bottom surfaces of the reagent bottles 25 (FIG. 33). Similarly, a conductive metal plate 260 is fixed across the upper surface of rim 242. It includes ribs 261 in close proximity alongside cups 35 and wells 36 within the ring segments 26. Plate 258 is used for capacitive sensing of liquid level within the reagent bottles 25 as liquid within them is approached by the descending pipette 18. Plate 260 performs the same functions with respect to liquid level sensing within cups 35 and wells 36. The liquid level sensing mechanism including these elements is described below.

Sample Tube Entry Port

Test samples can be individually delivered by the operator to a chemistry instrument 24 within a conventional draw tube 27 having a resealable stopper or closure 162. Manual delivery of a draw tube 27 to the sample tube entry port 20 initiates requisitioned tests relating to the liquid sample (blood, urine) contained within it. Removal of sample liquid from tube 27 is accomplished without destroying the seal provided by closure 162, which is of a type normally provided on draw tubes used for blood sampling purposes.

Sample tube entry port 20 is constructed as an operational module detailed in FIGS. 37–46. It is designed to receive and handle draw tubes 27 of differing lengths and diameters. It temporarily punctures the stopper of each draw tube 27, providing an opening through a puncture tube 161 for entry of pipette 18. The closure 162 on the draw tube 27 later reseals itself and wipes the exterior surfaces of both the puncture tube 161 and the pipette 18 as they are retracted outwardly from it.

The sample tube entry port 20 is designed about an elevationally movable ram 140 having an upwardly open receptacle 141 for holding a single draw tube 27. The ram 140 is detailed in FIGS. 43–46.

Sample tube entry port 20 is shown in FIGS. 37–41 with a receiving draw tube ram 140 at its "home" position. This is the position in which draw tubes are manually inserted into or removed from chemistry instrument 24. Operation of the sample tube entry port 20 is diagrammatically illustrated in FIGS. 47–59.

The module enclosure includes two spaced vertical side walls 152 and 153. These walls are transversely spanned by a front wall 154 and a rear wall 155. A forward horizontal flange 156 serves as a partial cover for the mechanism within the enclosure. A horizontally movable access cover 160 is slidably guided by rods 157 at each side of the enclosure.

One side of ram 140 has an open slot 143 leading to receptacle 141. Encoded information on labels applied to a draw tube 27 can be accessed through the slot 143 and read by a scanner 144. Transversely open apertures 186 also extend though the ram 140 next to the bottom end of receptacle 141. The presence of a draw tube 27 within ram 140 is detected by line of sight sensors 189 aligned with the apertures 186 and mounted on the opposed side walls 152, 153 of this module.

The bottom end of receptacle 141 is concavely dished to help in supporting draw tubes 27 of differing diameters. Receptacle 141 is also provided with two vertical ribs 142 along its back. They engage and transversely center draw tubes 27 of differing diameters, as shown by the circles drawn in dashed lines in FIG. 45.

The front of ram 140 is apertured at 145 to access the interior of receptacle 141. Two protruding brackets 185 are located below the aperture 184. A spring-biased tube clamp 146 is pivoted between brackets 185 about a transverse pivot shaft 147 extending between the side walls 152 and 153. The tube clamp 146 is spring-biased to an inner position projecting inwardly through recess 145, at which it engages the centerline of a draw tube 27 located within receptacle 141. The inward pressure exerted on a draw tube 27 by the spring-biased tube clamp 146 urges it rearwardly toward the two spaced centering ribs 142. This action transversely centers each draw tube 27 within ram 140 regardless of its diameter. Tube clamp 146 then yieldably holds tube 27 in a fixed position within ram 140 during later sampling procedures.

Tube clamp 146 includes an integral forwardly-projecting tab 149. A transverse rod 159 extends from side wall 152 of the module enclosure across the vertical path of movement of the tab 149. Engagement of tab 149 by the stationary rod 159 will result in outward movement of finger 147 from within receptacle 141 of ram 140 at the upper limit of movement of ram 140.

A rigid vertical rack 148 extends downwardly from ram 140. The rear surface of rack 148 has a vertical groove 72 formed along it. Groove 72 receives two guide rollers 150, which act in opposition to a driving gear 151 that meshes with the teeth formed across the front of rack 148 to support the rack 148 and ram 140. Gear 151 is powered by a DC motor 163 located on the outer surface of side wall 152. The combination of gear 151 and rollers 150 maintains ram 140 in a constant vertical orientation throughout the limits of its vertical movement relative to the supporting module enclosure.

Figure 40:
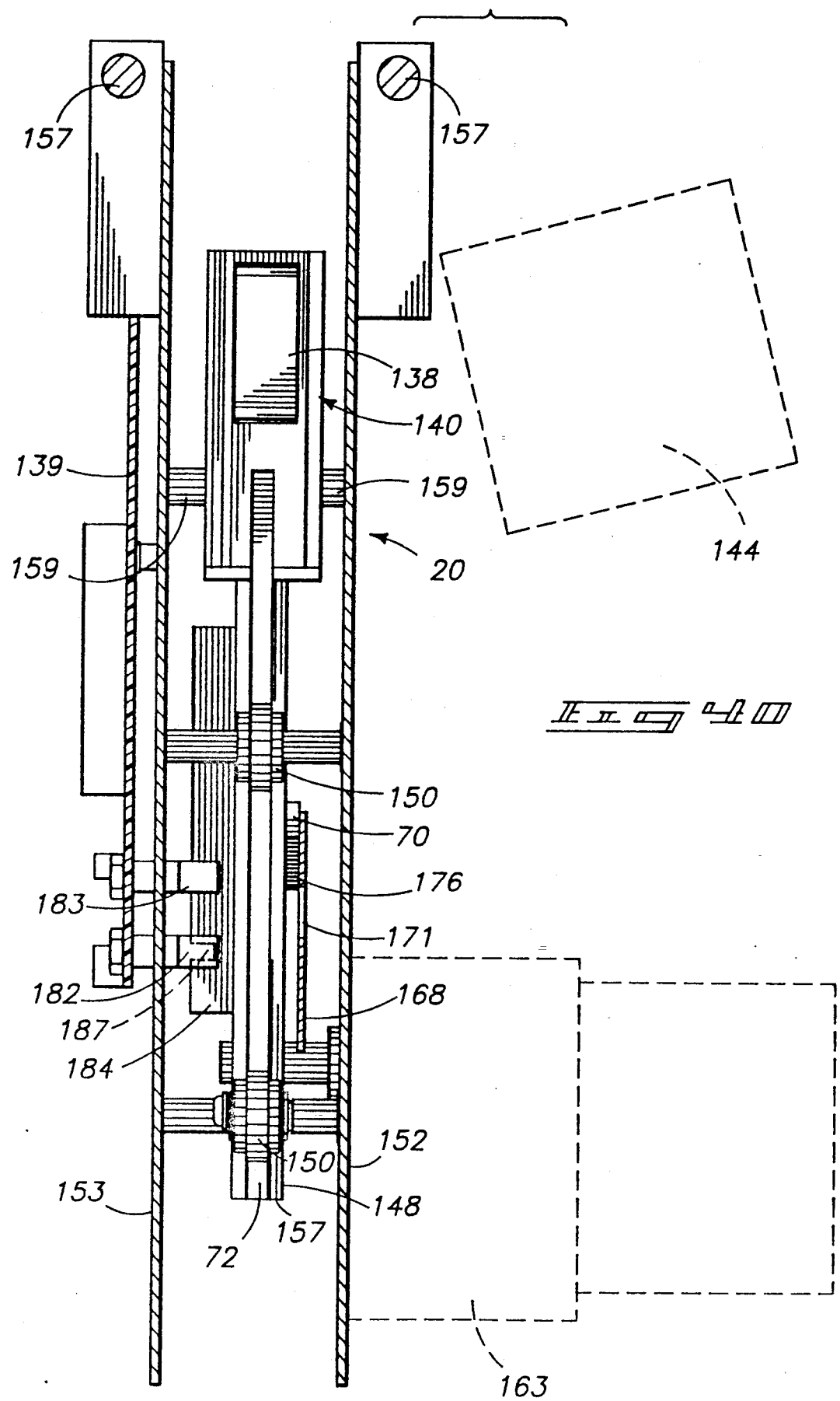
FIG. 40 is a sectional view taken along line 40—40 in FIG. 38.
Figure 41:
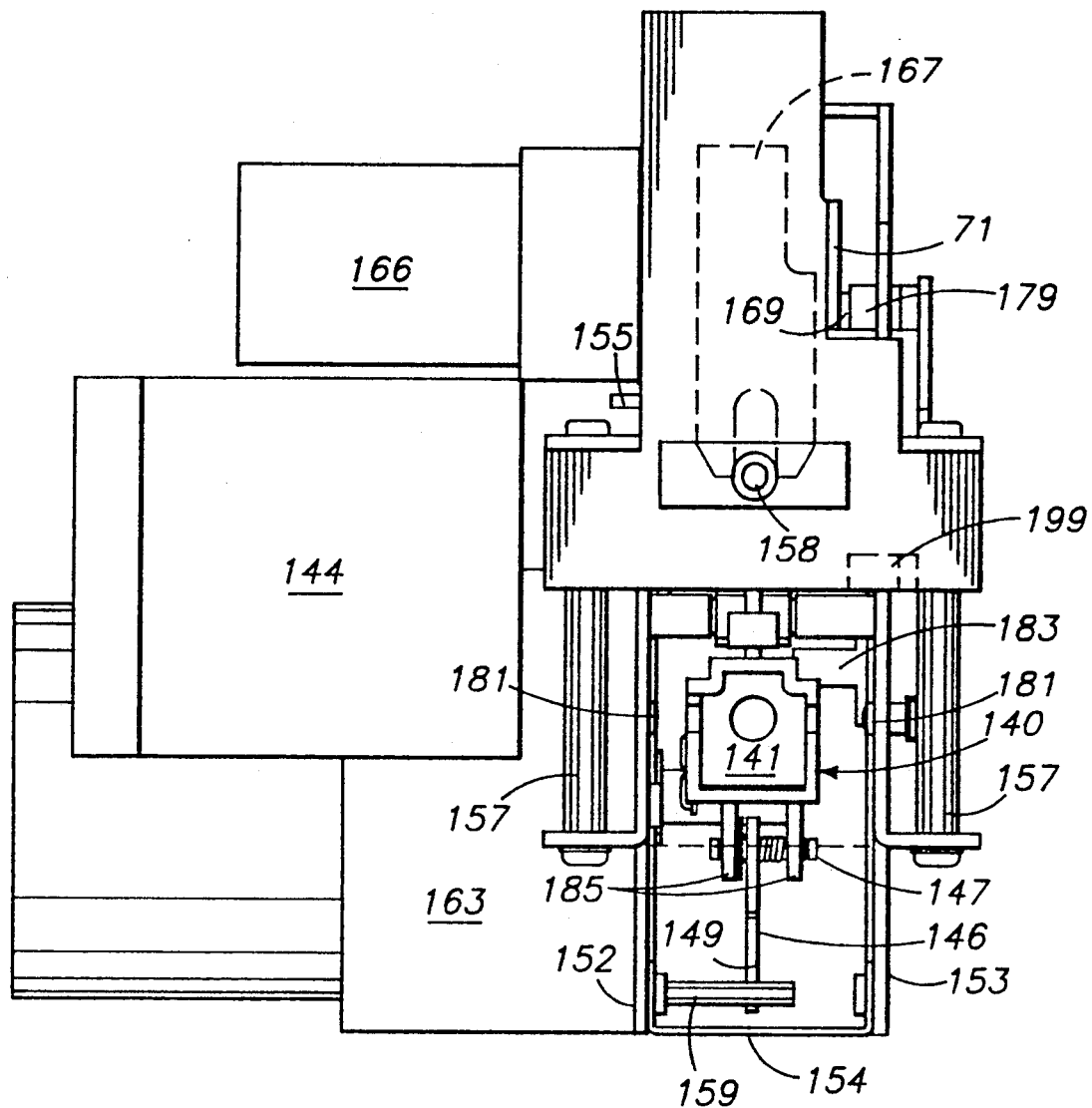
FIG. 41 is a top view of the module shown in FIG. 37.
Figure 42:
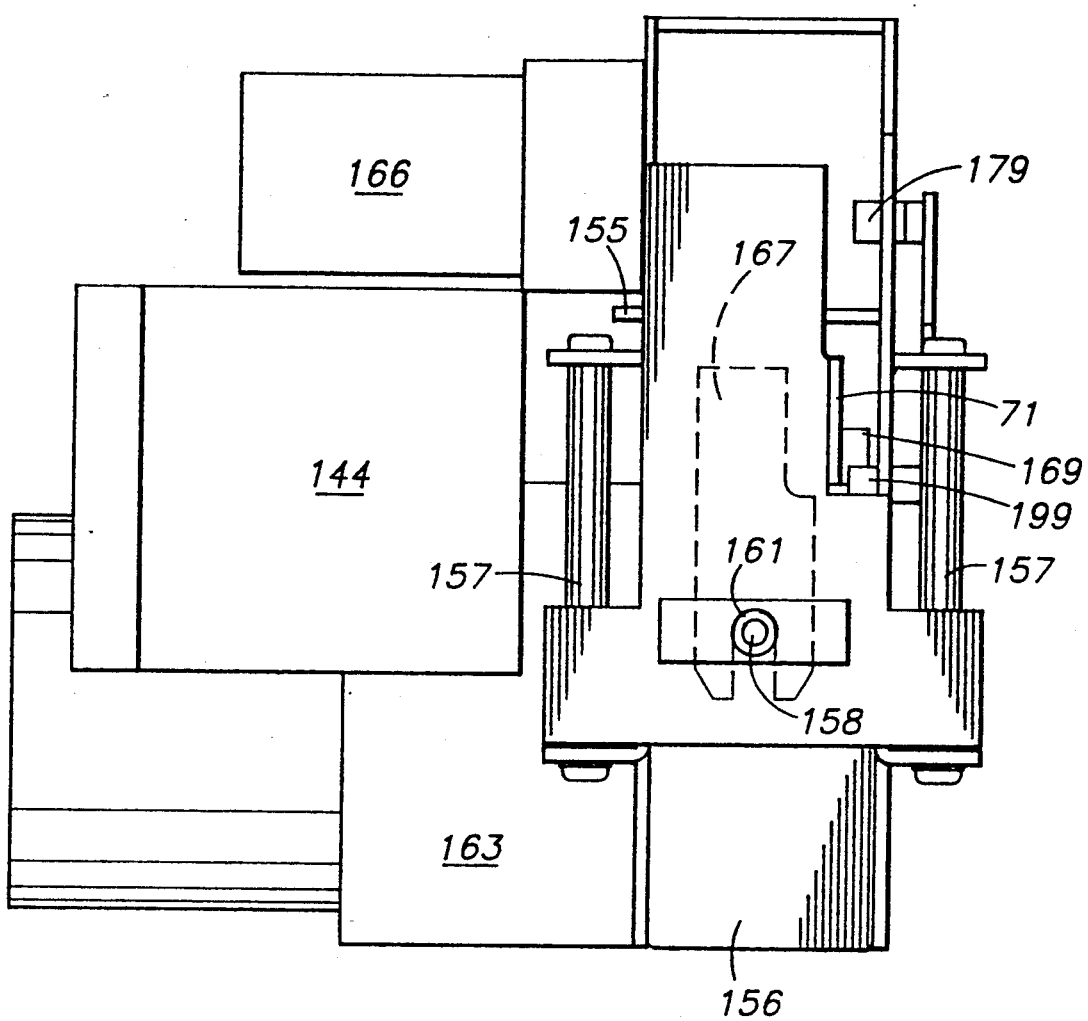
FIG. 42 is a top view with the cover in a closed position.

A longitudinal flag 184 protrudes to one side of rack 148 (see FIGS. 40 and 44). The upper end of flag 184 and an open notch 187 near its lower end are used to define predetermined limits of travel of ram 140 during its operation. They respectively act in conjunction with overlapping optical sensors 182 and 183 on the side wall 153 of the enclosure to detect maximum limits of vertical motion of ram 140 relative to the module framework. Line of sight sensors 181 are also arranged across side walls 152, 153, as shown in FIG. 37. The sensors 181 detect an intermediate position of each draw tube 27 as it is being raised vertically with the ram 140.

Cover 160 is reciprocated across the top of the enclosure by a rack 164 along its inside surface and a meshing drive gear 165. Gear 165 is powered by a DC motor 166.

The limits of movement of cover 160 are controlled by back and front sensors 179 and 199 mounted to a circuit board 159 located outwardly adjacent to side wall 153 of the module enclosure. A projecting horizontal flag 169 directed toward the adjacent side of cover 160 on a depending plate 71 is detected by the respective sensors 179 and 199 to terminate operation of motor 166 at the limits of cover movement. Detection of the positions of flag 169 assures that the cover 160 is either fully opened or fully closed for proper and safe operation of the chemical instrument 24.

Cover 160 mounts an open-ended puncture tube 161 designed to resealably puncture a conventional closure 162 on a draw tube 27. The inside diameter of puncture tube 161 is larger than the outside diameter of pipette 18. It presents an open aperture 158 for reception of the pipette 18 when the cover 160 is in its forward, or closed, position.

A bifurcated stripper 167 selectively overlies and engages the upper surface of a closure 162 on a draw tube 27 positioned within ram 140. Stripper 167 is centrally slotted at its front end to straddle the axial location of puncture tube 161 (see FIGS. 41 and 42). Its purpose is to prevent upward movement of closure 162 and draw tube 27 relative to ram 140 during removal of the puncture tube 161 and pipette 18 from a draw tube 27.

The stripper 167 is movably supported alongside the ram 140 by an integral extension 168. The lower end of extension 168 is pivotally guided on the supporting enclosure by a stationary shaft 170 received within a longitudinal slot 171. Shaft 17 is mounted to side wall 152 and mounts washers 172 that overlap the slot 171.

The upper end of extension 168 is similarly supported by a shaft 173 and overlapping washers 174. Shaft 173 is freely received within a second longitudinal slot 175 formed through extension 168. It is fixed to the plate 71 that extends downwardly from cover 160 next to side wall 153. Slot 175 within extension 168 is longer than slot 171. The extended length of slot 175 accommodates both the arcuate movement of extension 168 about the transverse axis of the stationary stub shaft 170 and the conjoint straight line movement of cover 160.

The lower end of extension 168 includes a straight section of gear teeth 176 formed across a transverse block 70 that faces toward rack 148. Gear teeth 176 are complementary to the teeth along rack 148. They are adapted to interfit with them to selectively lock extension 168 to rack 148 during operation of the sample tube entry port 20.

The lower end of extension 168 also includes a projecting flag 177. The position of flag 177 is detectable by upper and lower light sensors 178 and 180 on the rear wall 155 of the enclosure.

A stationary conductive metal plate 138 is spaced just slightly behind ram 140. It is supported on side wall 152. The elevation of plate 138 overlaps each draw tube 27 positioned within ram 140 at its uppermost position where the pipette 18 is inserted into it for sample access purposes.

The combination of the conductive plate 138 and conductive pipette 18 is used to capacitively sense the level of sample material within draw tube 27. By assuming that a draw tube 27 has the minimum diameter accommodated within the design limits of receptacle 141, measurement of the sample level can be converted by workstation 30 into usable sample volume information for inventory purposes. The calculation of remaining sample volume within a draw tube 27 also enables workstation 30 to guide the descending pipette 18 to a level adequate to remove the volume of sample needed for requisitioned tests.

Overview of Operation

The method for operating the chemistry analyzer 24 basically entails several randomly selectable steps. Its operation is timed about a repetitious sequence of cyclically transferring liquid from any selected container on the sample/reagent tray 15 to any selected cuvette 10 on the turntable 11, mixing liquids within the cuvettes on the turntable by turning it about the first axis, and rotating the turntable about the first axis. The timing of these steps is graphically depicted in FIG. 72.

The operational cycles of all components are timed to the repitious cycle of operation of turntable 11. The turntable 11 is held stationary by motor 12 for a period during which a disposable cuvettes 10 can be delivered to the turntable 11 by operation of the cuvette delivery module. This in turn displaces a spent cuvette into a disposal container in the instrument. The turntable 11 is sequentially indexed to a stationary angular position about the first axis shown at X—X with a selected cuvette 10 positioned at a cuvette access station A. It is then turned about the axis while mixing or centrifuging the contents of cuvettes 10 mounted to it.

As the contents of cuvettes 10 are being centrifuged within turntable 11, the step of analyzing their contents at a location next to the turntable takes place within the optical system.

Liquid samples and reagents are supplied to turntable 11 by indexing the sample/reagent tray 15 about a second axis parallel to and spaced from the first axis to a stationary angular position with a selected container positioned at a container access station C. By moving probe arm 17 and pipette 18 along an arcuate path centered about a third axis that is parallel to the first axis and intersecting both the cuvette access station A and the container access station C, the chemistry instrument 24 can selectively transfer liquids from containers positioned on the tray 15 at the container access station C to cuvettes 10 positioned on the turntable 11 at the cuvette access station A. The workstation 30 is programmed so the step of moving the pipette 18 provides randomly accessible transfer of liquid from any container on the tray to any cuvette on the turntable in the time in which the turntable 11 is stationary during each cycle of operation.

Operation of the sample tube entry port to deliver samples from a draw tube occurs, on a demand basis, during the spin cycle of turntable 11 shown in FIG. 72.

The method of sample delivery to chemistry instrument 24 involves the steps of receiving a manually placed draw tube 27 beneath the puncture tube 161, moving the draw tube between a lowered position wherein the draw tube is clear of the puncture tube and a raised position wherein the puncture tube forms a temporary opening through a closure on the draw tube, and subsequently inserting the pipette 18 coaxially through the opening in the closure to access the interior of the draw tube. It further comprises the step of detecting the level of liquid in the draw tube 27 as it is approached by the pipette 18, using the capacitive sensing system.

The sequence of operations for the sample tube entry port can best be understood by reference to the simplified illustrations of FIGS. 47-59.

FIG. 47 shows ram 140 in its "home" position, where it receives and discharges successive draw tubes 27. This position of ram 140 is defined by the notch 187 within flag 184, which is detected by optical sensor 183.

Cover 160 is in its retracted or open position when ram 140 is "home". The tube clamp 146 is retracted from within the receptacle 141 at the "home" position, since the tab 149 is held downwardly by its engagement against rod 159. Stripper 167 is pivoted rearwardly and displaced from the top of ram 140, leaving the receptacle 141 open to receive an incoming draw tube 27. A draw tube 27 can then be loosely placed within ram 140 by an operator to initiate taking of a liquid sample from within it.

Reception of a draw tube 27, when inserted manually in the direction shown by arrow A in FIG. 48, is sensed by line of sight sensors 189 on the opposed side walls 152, 153. Sensors 189 will be trained through the transversely aligned apertures 186 in ram 140 while the ram 140 is stationary at its "home" position.

Detection of a draw tube 27 located within receptacle 141 by action of the sensors 189 initiates operation of motor 163 to move ram 140 downwardly within its surrounding enclosure in the direction shown by arrow B in FIG. 49. As ram 140 moves downwardly, the finger 149 on tube clamp 146 will separate from stationary rod 159. This allows tube clamp 146 to pivot inwardly by spring pressure to engage against the draw tube 27 through the aperture 145 formed in ram 140. The pressure of tube clamp 146 urges the draw tube 27 back between the vertical ribs 142 within the receptacle 141 to center and hold it securely within ram 140 regardless of its diameter or length.

Downward movement of ram 140 then continues in the direction of arrow B to its bottom limit of movement (FIG. 49). This extreme lower position is defined by detection of the upper end of flag 184 by sensor 182.

When the bottom limit of movement of ram 140 is reached, the controls for motor 163 will be reversed to impart upward movement to it in the direction shown by arrow C in FIG. 50. This upward movement will continue until the top surface of the closure 162 on the draw tube 27 is sensed by line of sight sensors 181 trained between the side walls 152, 153 of the enclosure.

The intermediate limit of upward motion for a specific draw tube 27 is illustrated in FIG. 50. It is to be noted that this limit of movement is defined by the top surface of the closure 162 and is independent of the axial length of draw tube 27.

After the draw tube 27 has been raised to its intermediate elevated position, as shown in FIG. 50, a bar coded label or other readable indicia along the side of the draw tube 27 is scanned by digital scanner 144. The scanned identification data can then be transmitted to the programmed workstation 30 to access requisition information supplied with respect to the sample. The scanned data also permits the identification of the sample to be verified. By matching the identification data and requisition data for a specific sample, the analyzer can then program the tests to be conducted upon it and compute the amount of sample that must be removed from the draw tube 27 for such tests.

If the sample identification and requisition information is not matched in workstation 30, control signals supplied from it to motor 163 will override photocell detector 181 and cause the ram 140 to return to its "home" position, as shown in FIG. 48, where the draw tube 27 can be manually removed from the sample tube entry port. At this point the operator can remove and rotate the reinserted draw tube 27 to align encoded indicia along its side with the slot 143 for access by scanner 144 or can manually input identifying data through keyboard 32. Replacement of draw tube 27 within receptacle 141 will cause the steps described with respect to FIGS. 48-50 to be repeated until the sample identification sequence is successfully completed.

Assuming that a draw tube 27 and inputted requisition data have been properly identified, either through scanner 144 or keyboard 32, the removal of sample liquid from within the draw tube 27 is then carried out automatically with no further manual intervention.

Figure 51:
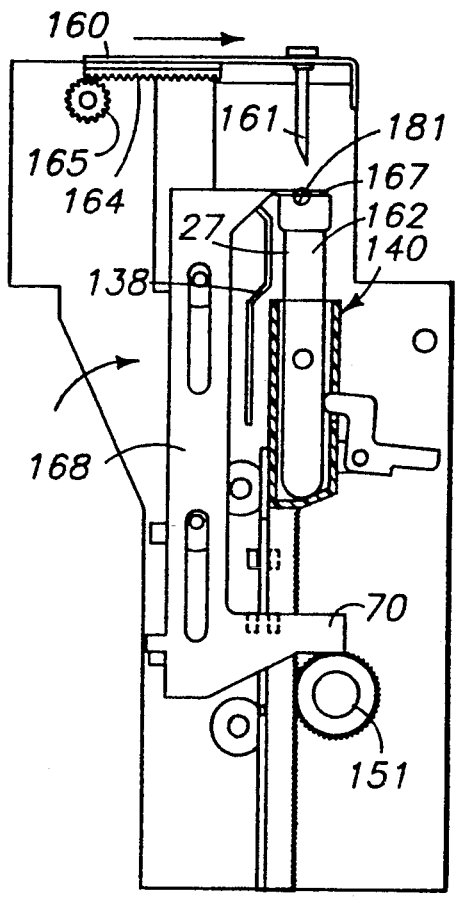

The next step in the procedure involves forward movement of cover 160 in the direction shown by arrow D in FIG. 51. This cover motion, which is initiated under control of workstation 30, prevents further manual access to the draw tube 27. Closing of cover 160 also axially aligns puncture tube 161 above closure 162.

As closing movement of cover 160 occurs, the stripper 167 and extension 168 will be pivoted about stub shaft 170 by the connection between shaft 173 and extension 168 to bring extension 168 into a vertical position parallel with rack 148. This causes gear teeth 176 to engage and be interfitted with the teeth along the front of rack 148. Because extension 168 will then be resting at the upper end of slot 171, extension 168 will be clamped to rack 148 in a predetermined elevational relationship position with stripper 167 immediately adjacent to the previously-referenced elevation of the upper surface of stopper 162. In this position, both the upper surface of the closure 162 on draw tube 27 and the stripper 167 are elevationally referenced with respect to the enclosure-closure 162 by operation of sensors 181, and stripper 167 by the engagement between slot 171 and stub shaft 170. They can thus be accurately positioned relative to one another regardless of draw tube height.

Figure 52:
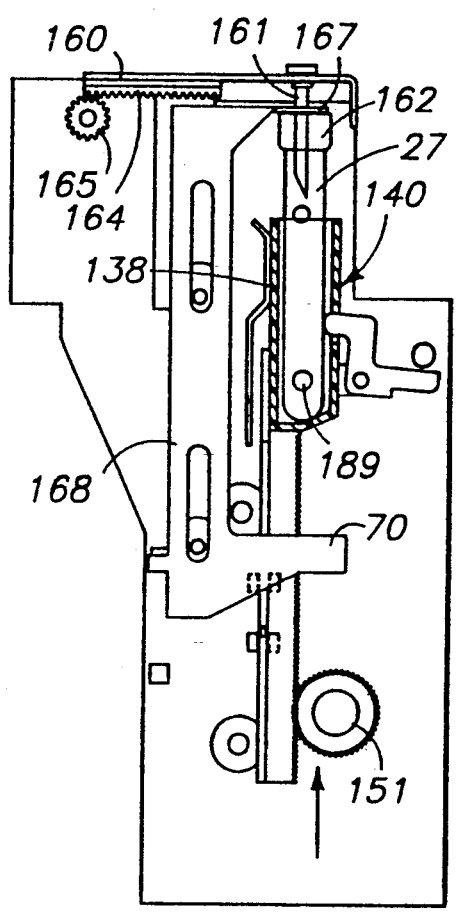

Puncturing of closure 162 is accomplished by raising the engaged ram 140 and extension 168 in unison through operation of motor 163. This elevational motion, in the direction shown by arrow E in FIG. 52, is limited by sensor 178. Sensor 178 detects the upper limit of movement of extension 168 when it is blocked by flag 177, as shown in FIG. 52.

After closure 162 has been punctured, the probe arm 17 is pivoted about its axis on the chemistry instrument 24 in the manner illustrated by arrow F in FIG. 53. The movements of probe arm 17 occur under control of the programmed workstation 30 to align pipette 18 above aperture 158 (FIG. 53). Probe arm 17 can then be lowered in the direction shown by arrow G in FIG. 54 to insert pipette 18 downwardly into draw tube 27. The amount of liquid to be drawn from the draw tube 27 is governed by microprocessor control and instructions programmed into the workstation 30 for a specific test requisition.

Figure 55:
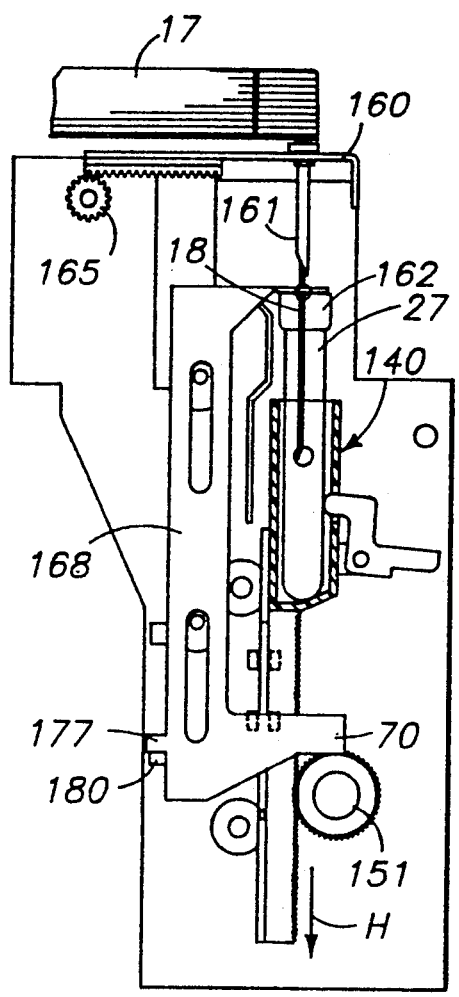

Following receipt of the liquid sample, ram 140 is initially moved downwardly in the direction shown by arrow H in FIG. 55 until flag 177 is detected by sensor 180. The straddling nature of the bifurcated stripper 167 resting against the upper surface of closure 162 assures against displacement of the closure 162 with respect to draw tube 27 as they are lowered relative to the stationary puncture tube 161. It is to be noted that pipette 18 is stationary and partially remains within the draw tube 27 during withdrawal of puncture tube 161.

Figure 56:
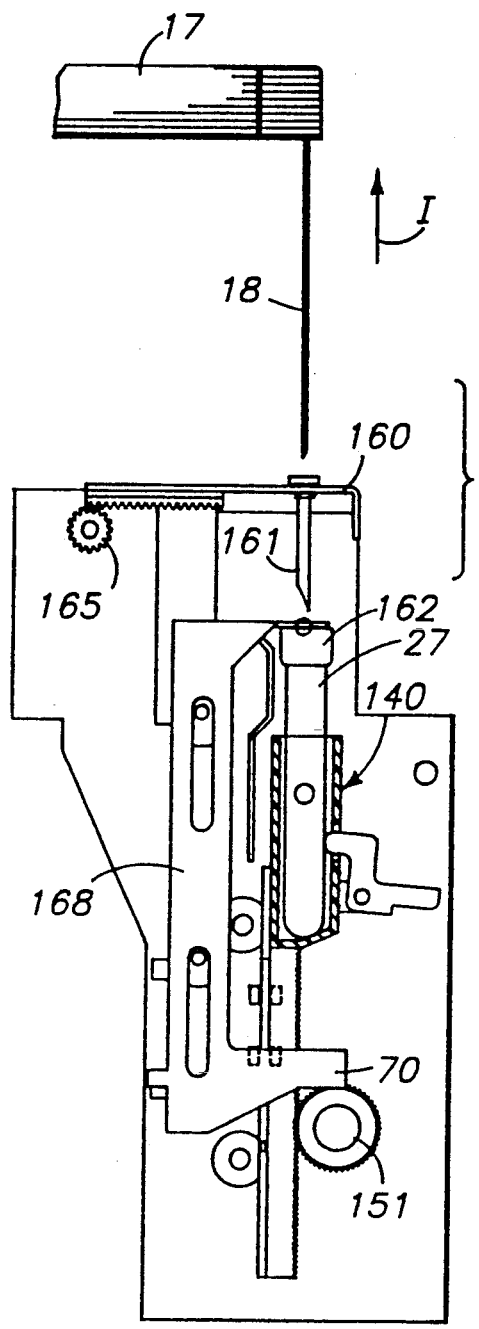

After closure 162 has been lowered to the position shown in FIG. 55, where it is clear of puncture tube 161, probe arm 17 can be raised in the direction shown by arrow I in FIG. 56 to retract pipette 18 upwardly through aperture 158 in cover 160. The resealing closure 162 will then wipe the outer surfaces of pipette 18 to prevent liquid from dripping from the exterior of the pipette as it is lifted upwardly. Pipette 18 is then freed for later movement about the chemistry instrument 24.

Figure 57:
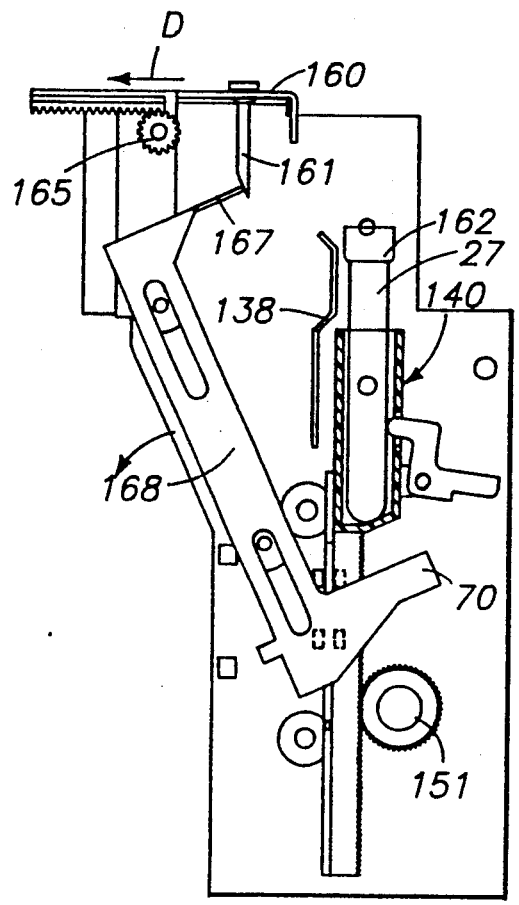

Following lifting of pipette 18, the workstation 30 operates motor 166 to move cover 160 rearwardly in the direction shown by arrow J in FIG. 57. Retraction of cover 160 also separates gear teeth 176 from rack 148, returning the stripper to its original position.

Figure 58:
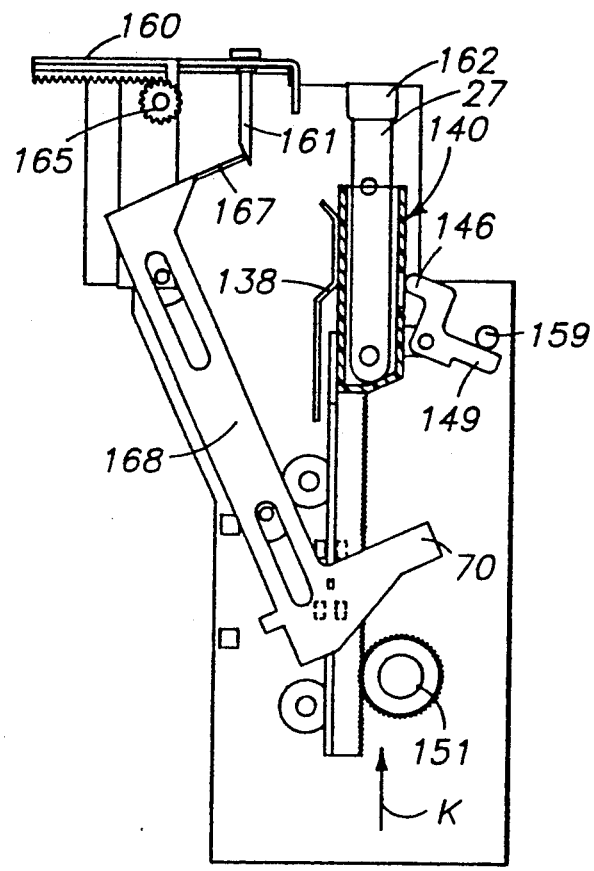
Figure 59:
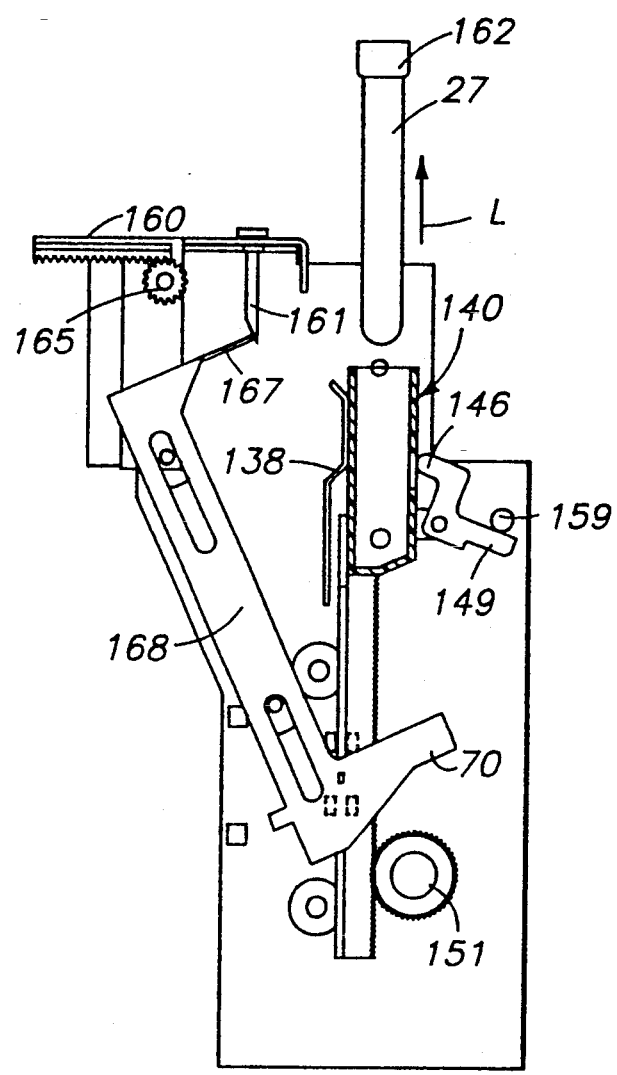
Figure 78:
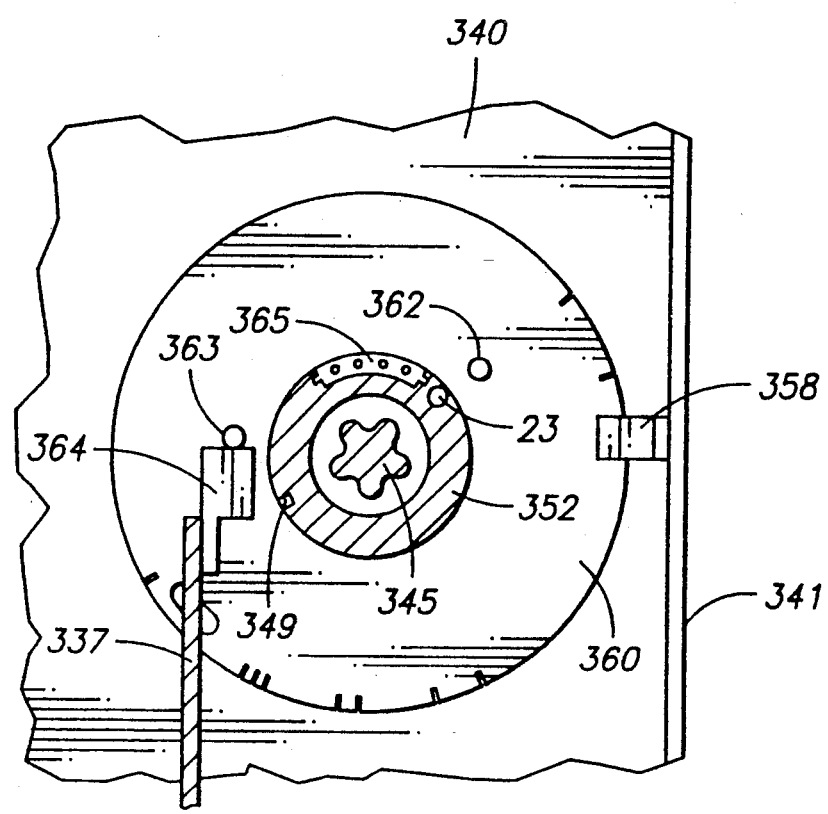
FIG. 78 is an enlarged cross-sectional view taken along line 78—78 in FIG. 76.

After retraction of cover 160 has been completed, motor 163 is again activated to raise ram 140 in the direction shown by arrow K in FIG. 58 to its "home" position, where tube clamp 146 is released. The resealed draw tube 27 can then be manually lifted from ram 140 in the direction shown by arrow L in FIG. 59, leaving ram 140 again in its "home" position, where it is ready for reception of a subsequent draw tube. Successive draw tubes can be manually supplied to the chemistry instrument 24 at any time during its operation.

Wash/Alignment Station

The wash/alignment station 21 is detailed in FIGS. 60-64. It comprises a molded basin 271 adapted to be inset into the enclosure platform 238. Basin 271 is covered by a metal plate 276 having an elongated aperture 278 located above an interior deep wash well 272 and tip wash well 273 within the basin 271. Each well 272, 273 is closed at its lower end. The interior of basin 271 has inclined surfaces leading from wells 272, 273 to a common liquid drain 274.

Pipette 18 is washed periodically during operation of the chemistry instrument 24 by inserting its lower end into one of the wells 272 or 273. Water is then flushed through pipette 18 by operation of the syringe module 22. The flushing action of the water cleanses both the interior and exterior surfaces of pipette 18 as it flows downwardly through the pipette and upwardly through the selected well. The waste water is carried away at drain 274 for disposal.

The choice of which well will be used during a specific washing operation will depend upon the depth of liquid contact along the lower end of pipette 18 during the preceding liquid transfer operations. When practical, the analyzer is programmed to utilize the tip wash well 273 as the preferential washing apparatus, since it uses less water and the washing sequence can be carried out more quickly than in the deep wash well 272.

The elongated aperture 278 formed in metal plate 276 leads to radiused ends 280 and 281 centered over the respective wells 272 and 273. The inside radius at each end 280 and 281 is slightly greater than the outside radius of pipette 18. Therefore, the aperture 278 does not interfere with normal entrance of pipette 18 into the wash wells 272 and 273.

The metal plate 276 is utilized to periodically check both axial and radial alignment of pipette 18 relative to the supporting probe arm 17. The probe arm 17 is programmed to periodically initiate an alignment test sequence for this purpose. The circuitry for accomplishing this task is described below.

Each alignment test sequence involves insertion of the pipette tip through the center of aperture 278 and subsequent shifting of pipette 218 to the nominal center position adjacent the radiused end 280 of plate 276 (arrow A in FIG. 64) and then to the nominal center position adjacent to the radiused end 281 (arrow B in FIG. 64).

Any physical engagement between pipette 18 and the plate 276 during the test sequence will be detected electronically and will abort the alignment procedure. This will result in the probe arm 17 positioning the pipette 18 at a realignment location upwardly adjacent to plate 276. A visual mark can be provided above the ISE port E to assist the operator in bending pipette 18 to align it properly.

Assuming that no contact takes place during the back and forth swinging movement of the pipette tip within the aperture 278, and radial alignment of the pipette 18 is therefore confirmed, the probe arm 17 will next proceed to test its axial or elevational alignment with the probe arm 17 and supporting components of the chemistry instrument 24 by detection of the elevation of the lower end of pipette 18. This is accomplished by first moving pipette 18 into physical touching contact against the radiused end 281. When contact has been electrically detected, probe arm 17 can then be raised until the pipette tip just clears the top surface of plate 276. The detection of this elevation is then used as a reference to calibrate the elevation of pipette 18 relative to the platform 238 and all operational equipment supported on it, including the sample tube entry port 20, the sample/reagent tray 15, the ISE module 38, and the cuvette turntable 11.

Utilization of the wash/alignment station 21 can be programmed into any test sequence to either wash the operative end surfaces of pipette 18 or to check its radial and/or axial alignment on probe arm 17.

It is to be understood that the functions of washing the pipette surfaces and checking its alignment are independent. They have been combined in the illustrated station only for reasons of economy in space utilization about the supporting platform 238. The basin 271 and plate 276 can be separately mounted and used independently from one another when desired.

Liquid Transfer Module

The liquid transfer module which moves preselected volumes of sample liquids, diluents and reagents between the components of the chemistry instrument 24 is designed about the rigid radial probe arm 17 that supports the vertical pipette 18. As schematically shown in FIG. 1, probe arm 17 is supported and powered by operator 19 for moving it angularly and axially relative to a vertical support axis on the framework of the chemistry instrument 24. Suitable sensors are included within the liquid transfer module for detecting the angular and axial position of probe arm 17 relative to the supporting instrument framework.

In general terms, the liquid transfer module is developed about a tubular shaft 352 fixed to and extending beneath the inner end of the probe arm. The tubular shaft 352 is centered about a fixed vertical axis on which the plurality of liquid stations on the framework are arcuately centered. Main bearing means (Shown as bearing assembly 340) operably supports the shaft on the framework for both elevational and pivotal motion of the shaft relative to the framework. A first coaxial drive means (shown as lead screw 345) is operably connected to the shaft for moving it elevationally relative to the instrument framework. A second coaxial drive means (shown as pulley assembly 353) is operably connected to the shaft for moving it angularly relative to the framework.

Details illustrating the structure of the liquid transfer module are shown in FIGS. 76-79. The probe arm 17 is further illustrated in FIGS. 80-84.

The liquid transfer module is structurally supported on cover 34 of the supporting instrument framework by an upright bearing assembly 340. The bearing assembly 340 includes a stationary module frame 337 suspended beneath cover 34. The frame 337 mounts the operator 19 generally described in functional terms in the overview of the system components. It also mounts a printed circuitboard 341 for the electronic and electrical components associated with the liquid transfer module.

The module frame 337 mounts two independently controlled stepper motors 342 and 343. The lower stepper motor 342 (FIG. 77) selectively positions the probe arm 17 in a vertical direction along its support axis (shown at line A—A in FIGS. 76 and 77). The upper stepper motor 343 selectively positions probe arm 17 in an arc about axis A—A.

The module frame 337 also supports a stationary lower bearing assembly 344 that rotatably carries the bottom end of a threaded vertical lead screw 345. Lead screw 345 is coaxially centered about the axis A—A. It can be selectively rotated by stepper motor 342 through an attached lower pulley assembly 346 and an interconnecting flexible timing belt 347.

The vertical tubular shaft 352 coaxially surrounds the lead screw 345. The inner end of probe arm 17 is fixedly attached to the upper end of tubular shaft 352 for movement relative to the instrument enclosure as previously described. An elongated sleeve bearing 355 and upper and lower rotational bearings 338 within bearing assembly 340 suspend the tubular shaft 352 on the instrument framework for both axial and rotational movement relative to the axis A—A.

A cable 365 leads through an axial recess formed along the length of shaft 352 from a connector 366 on printed circuit board 341 to a connector 367 at the underside of probe arm 17. A flexible tube 23 also extends within an axial recess along the exterior of tubular shaft 352 between the lower end of the shaft and a releasable fluid coupling to a fluid conduit within probe arm 17. Tube 23 leads outwardly from the lower end of tubular shaft 352 to the syringe module 22 of the chemistry instrument 24 to control supply of fluids to and from the tip of pipette 18. The periphery of lead screw 345 is threadably engaged by an encircling nut 348 having interior threads (not shown) that complement and engage the exterior threads along the length of lead screw 345.

The lower end of nut 348 is fixed to a radial guide 350. The radial guide 350 includes axial bearings 333 that rotatably carry the lower end of the tubular shaft 352. Guide 350 encircles and is slidably engaged along a vertical post 351 fixed to the module frame 337. The sliding vertical interconnection between guide 350 and post 351 prevents rotation of nut 348 about the vertical axis of lead screw 345. Rotation of lead screw 345 selectively imparts vertical movement to the non-rotating nut 348 and to the tubular shaft 352 elevationally supported on bearings 333. Because the lower end of tubular shaft 352 an freely rotate relative to the radial guide 350, vertical movement imparted to shaft 352 by operation of stepper motor 342 is independent of the angular position of the shaft about axis A—A.

The outer surface of shaft 352 is slidably guided within a surrounding upper pulley assembly 353 rotatably supported at the lower end of sleeve bearing 355. Shaft 352 is free to move vertically within the surrounding pulley assembly 353, but cannot pivot or rotate relative to it. An interconnection between the pulley assembly 353 and shaft 352 is provided by a radial key 349 projecting radially inward within a full length axial slot or keyway at the exterior of shaft 352.

Pulley assembly 353 is drivingly connected to the output of stepper motor 343 by a second timing belt 354. Operation of stepper motor 343 results in angular motion being imparted to the shaft 352 about vertical axis A—A. The angular movement imparted to shaft 352 by operation of stepper motor 343 is independent of the shaft elevation.

Figure 79:
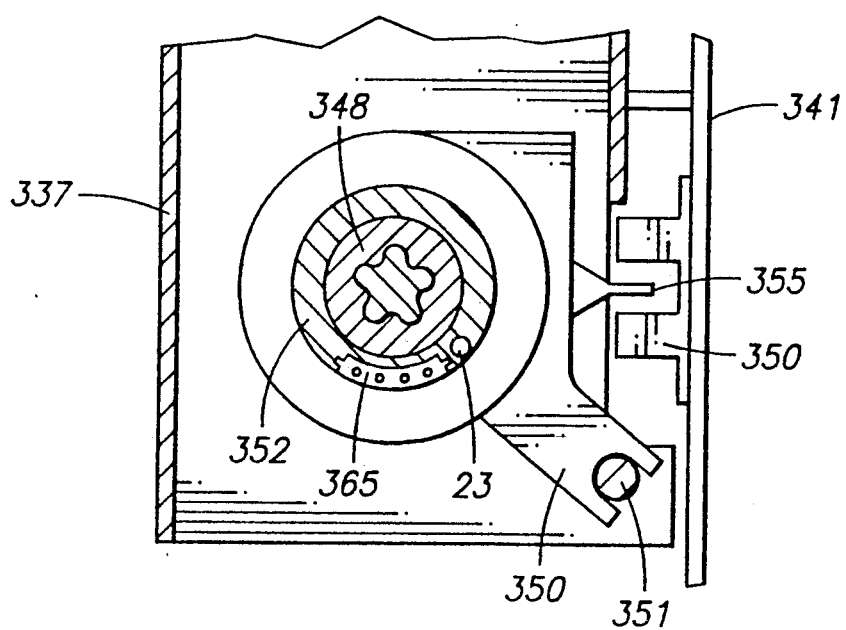
FIG. 79 is an enlarged cross-sectional view taken along line 79—79 in FIG. 77.
Figure 80:
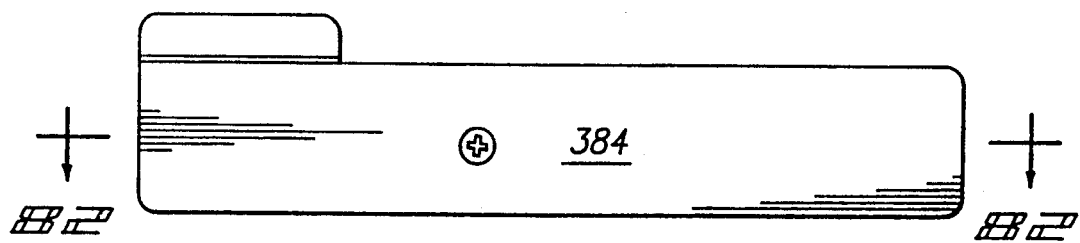
FIG. 80 is a top view of the probe arm.
Figure 81:
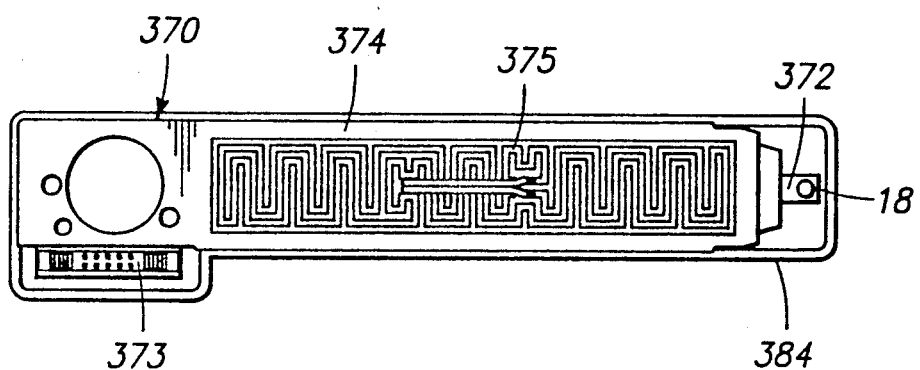
FIG. 81 is a bottom view.
Figure 82:
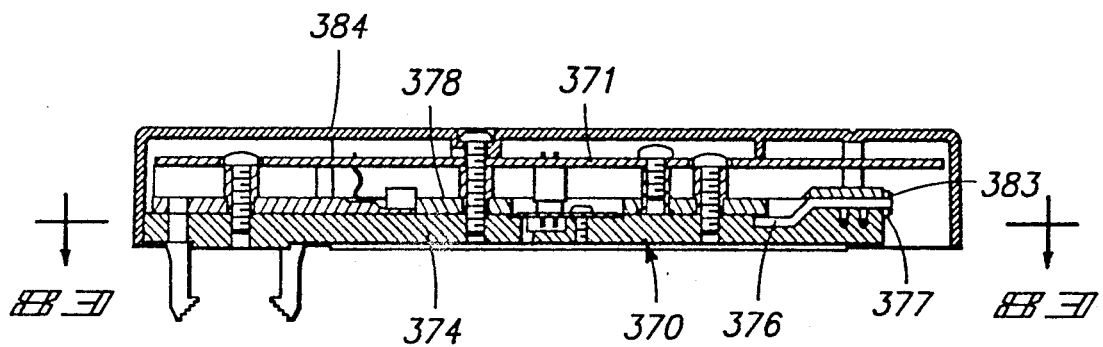
FIG. 82 is a sectional view as seen along line 82—82 in FIG. 80.
Figure 83:
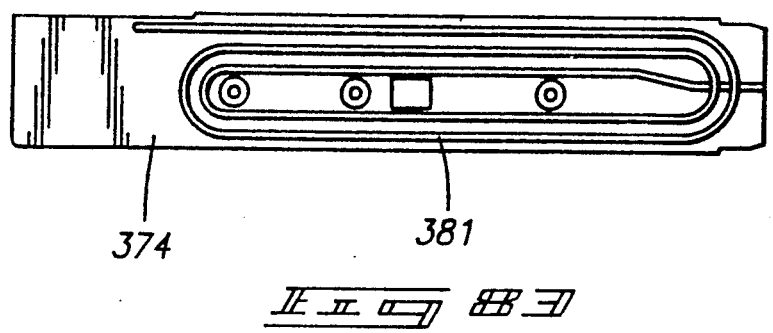
FIG. 83 is a plan view of the bottom casting for the laminated plate in the probe arm, as seen along line 83—83 in FIG. 82.
Figure 84:
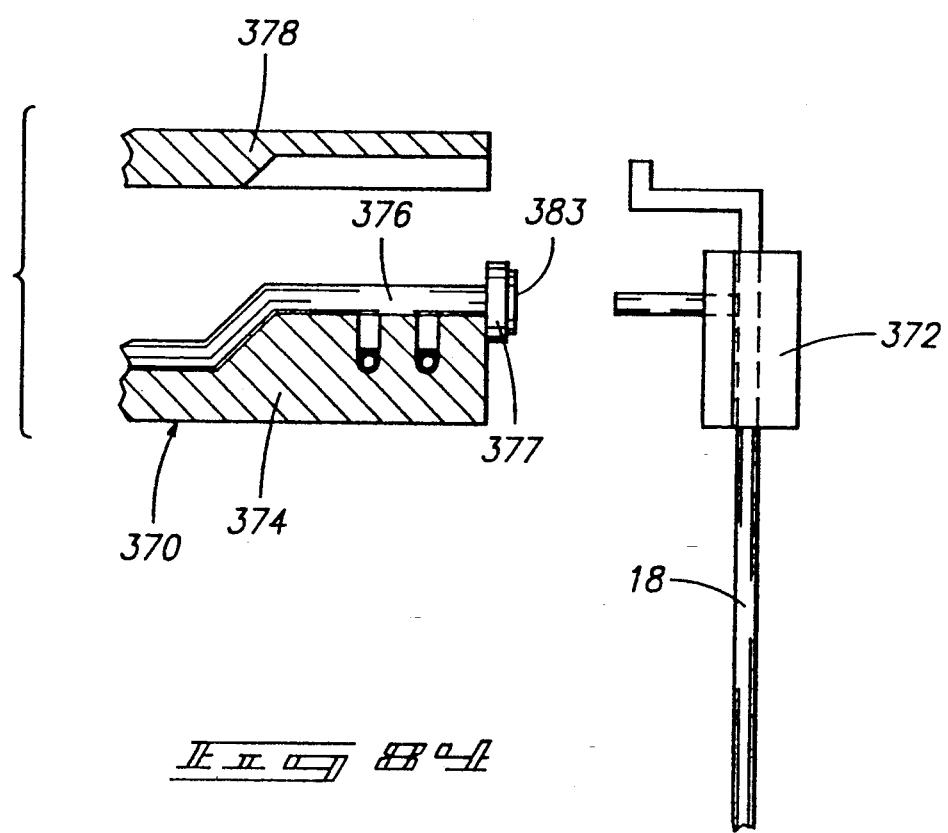
FIG. 84 is an exploded vertical sectional view of the pipette mount.

The vertical limits of movement of shaft 352 relative to the module frame 337 are defined by a protruding flag 355 fixed on guide 350 which passes through lower and upper photo detectors 356, 357, respectively (see FIGS. 77 and 79). Operation of stepper motor 342 is terminated by operation of a microprocessor upon detection of flag 355 being straddled by either of the photo detectros 356 or 357. Stepper motor 342 can accurately position tubular shaft 352 at any elevation between these two extreme elevational limits.

The rotational position of tubular shaft 352 is monitored by a photo detector 358 mounted to circuitboard 341. Photo detector 358 straddles a circular disk 360 clamped to and the upper pulley assembly 353 (see FIGS. 76, 7 and 8). The periphery of disk 360 is radially slotted at 361. Slots 361 are located at angular intervals that properly locate pipette 18 at its required operational positions about the chemistry instrument 24.

To prevent physical damage to probe arm 17 and pipette 18 that might occur due to rotation about the axis A—A beyond its intended range of motion, two motion-limiting pins 362, 363 protrude downwardly from the underside of disk 360 on the pulley assembly 353. The physical stops provided by pins 362 and 363 also prevent the controlling software that governs pivotal motion of probe arm 17 from becoming "lost". They limit the zone of its pivotal motion to the arc including the slots 361 on disk 360.

The rotational paths of pins 362 and 363 abut opposite sides of a fixed bent tab 364 that serves as a stop. Contact of tab 364 by either pin 362 or 363 physically prevents tubular shaft 352 from moving in a complete circle. Such motion would result in damage to probe 18. The limit on rotational movement of tubular shaft 352 further protects the respective lengths of cable 365 and tubing 23 that extend outwardly at the bottom of shaft 352.

Probe arm 17 comprises a rigid laminated plate 370 that supports a parallel printed circuit board 371 located above it. The printed circuit board 371 mounts the circuitry and electrical devices that control and operate the heating functions of plate 370. A conventional electrical connector 373 at one side of printed circuit board 371 is releasably connected to the coupler 367 at the upper end of cable 365 (see FIG. 76). The laminated plate 370 structurally supports a convoluted liquid path leading to pipette 18. A resistance heater film 381 is laminated to the bottom surface of plate 370 (FIG. 81) for warming liquids traversing the path. Operation of the heater film 381 can be activated to warm liquids along the probe arm 17 to a desired reaction temperature during liquid transport.

Laminated plate 370 is formed from two substantially planar metal castings comprised of aluminum or other metal having good heat distribution qualities. The lower casting 374 carries a flat electrical resistance heating element 375 fixed to it along its bottom surface. Its top surface has a spiralling groove 381 recessed within it to seat an elongated length of flexible tubing 376. Casting 374 and tubing 376 are covered by a complementary metal casting 378 to form a sealed, heat conductive environment for liquid within tubing 376.

Tubing 376 winds along a continuous oval pattern leading from one side edge of plate 374 adjacent the inner end of casting 374 to the center line of casting 374 adjacent its outer end. The outer end of the length of tubing 376 is flared at 383 (FIG. 84) and backed by a rigid washer 377 adhesively secured to the outer end of plate 370. The inner end of tubing 376 is interconnected to the upper end of tubing 23 by a tubular releasible connector.

A pipette mounting bracket 372 is releasably carried at the outer end of heater 370. Bracket 372 supports the bent upper end of a metal pipette 18. An electrically conductive spring clip 382 on bracket 372 provides an electrical path between the pipette 18 and the wiring of circuitboard 371.

The bent upper end of pipette 18 frictionally seats within the open flared end of tubing 376 to form an effective sealed connection between them. Pipette 18 is secured on the laminated plate 370 by mechanically fastening the bracket 372 to its outer end surface in a manner permitting pipette replacement as necessary.

The components of probe arm 17 are protected within the confines of a removable upper cover 384. Temperature sensors can be located about the laminated plate 370 as required to monitor temperature conditions along the fluid path defined within it.

Syringe Module

Syringe module 22 is diagrammatically shown in FIG. 65. It essentially comprises a linear syringe 294 that includes a reciprocating piston for pushing or pulling water as required during a specific operation. This action is used to direct fluid from the tip of pipette 18 or to aspirate fluid into the pipette, as well as for washing of the tip by rinsing it within the wash/alignment module 21. When sample liquids are diluted within a well 36, stirring of the liquid materials is accomplished by oscillating the pipette about its axis on the instrument framework.

Syringe 294 is powered by a stepper motor 296 through an interconnecting lead screw assembly 298. A disk 299 on the lead screw 298 is read by an optical sensor 300 to provide electronic indications of the linear position of the piston within syringe 294.

Electrically operable valves 303, 304 and 305 are interposed along the lengths of tubing that interconnect syringe 294 to the pipette 18, a source of water within container rack 28, and a waste water container 302, respectively. By selectively opening and closing these individual valves, water can be pumped to or from syringe 294 without contamination of the available water supply source. Operation of the syringe module, which is basically of conventional design, should be readily understood by those skilled in this field.

Capacitive Sensing System

A capacitive sensing system is provided within chemistry instrument 24 for sensing of liquid levels by use of pipette 18, for sensing radial misalignment of pipette 18 and for sensing the elevational position of pipette 18. FIG. 67 is a simplified plan view of the supporting platform 238 and the components mounted to it which are used effectively as plates of a sensing capacitor in the detection circuitry. FIGS. 68-70 diagrammatically illustrate the circuitry involved in this system.

The capacitive sensing system provides a mechanism for dynamically sensing the surface of liquid in a container, such as the reagent bottles 25 mounted within sample/reagent tray 15. The ability to determine the elevation of the surface of the liquid allows the equipment controlling insertion of pipette 18 into liquids to limit surface contact with reagents and samples, thereby minimizing the amount of excess liquid carried at the outside surfaces of pipette 18 and resulting contamination from sample to sample. It also permits the system to maintain an updated inventory of liquid in all containers included in the chemistry instrument 24 and to notify the operator of system requirements in a timely manner.

When liquid is to be drawn from a container, pipette 18 can be lowered relative to the sensed liquid surface elevation, an amount adequate to draw the liquid upwardly into the pipette without risking physical engagement between the pipette tip and the bottom of the container and without unduly submerging the pipette to a depth that is more than necessary for such purposes.

The physical characteristic measured by the system is the capacitance between a liquid within a container and a metal plate in close proximity to the container. The liquid in the container, when contacted by pipette 18, acts as one plate of the measured capacitor, assuming that the liquid has the ability to become ionized or is polar in nature.

With respect to fluid level sensing, the system components illustrated in FIG. 66 that measure fluid level are the pipette 18 at the outer end of probe arm 17, the conductive plate 260 located immediately beneath the cups 35 and wells 36 on ring segments 26 mounted to the sample/reagent tray 15, the conductive plate 258 fixed within well 240 immediately beneath the reagent bottles 25 mounted in sample/reagent tray 15, and a conductive plate 138 mounted adjacent to a vertically movable ram 140 that supports a sample tube 27 in the sample tube entry port 20. In addition, the sensing circuitry is used to detect radial misalignment of pipette 18 when it has been partially inserted through aperture 278 formed in metal plate 276. Interaction between plate 276 and pipette 18 is also used in conjunction with this system to verify the elevational position of the pipette 18 relative to the fixed elements of the chemistry instrument 24 supported on platform 238.

As shown in FIG. 67, the plates 138, 258, 260 and 276 are connected to a driving oscillator 284 in a series circuit. The connections to plates 138, 258 and 260 can be made directly to the drive signal output of oscillator 284. Since pipette 18 will be brought into direct contact with conductive plate 276 during probe alignment procedures, a fixed resistor 283 is provided in series with it to assure that the center frequency of the bandpass filter 288 can be found.

There are three major items included within the capacitive sensor system shown in FIG. 68. They are (a) a gated voltage-controlled oscillator 284, (b) a capacitance measurement jig, situated at one or more locations accessible to the pipette 18, each including a conductive drive plate, and (c) a low input impedance amplifier 287 with a bandpass filter 288 tuned to the output frequency of oscillator 284.

Oscillator 284 provides the drive signal that will ultimately be measured by the detector circuitry connected to pipette 18. It is preferably a sine wave oscillator whose output can be gated.

One significant feature of this circuit is that oscillator 284 is tunable by a microprocessor within the liquid transfer module, which also monitors the frequency of the signals transmitted through pipette 18. This allows for constant fine tuning of the frequency of oscillator 284 so that its output signal is precisely tuned to the center of the band pass filter frequency. The algorithm for tuning oscillator 284 can be run during periods of reduced system activity so as to always maintain optimum system performance and to eliminate adjustments during normal operation of the analyzer.

The ability to control the frequency of the signal produced by oscillator 284 allows fine tuning of the system to optimize the detector circuits. As an example of selectable operational parameters, the oscillator 284 might produce a 262 Khz drive signal and filter 288 might pass only signals at a frequency of 262 kHz.

Each capacitance measurement jig provides the means by which the drive signal from oscillator 284 can be coupled into the liquid-containing portion of the capacitor being measured. When the pipette tip comes into contact with the liquid at the liquid level, denoted by dashed line 286 in FIG. 68, the capacitive coupling between pipette 18 and drive plate 258 will become significantly greater and the transmission of the drive signal from oscillator 284 through the capacitor will increase.

Significant signals received through pipette 18 are coupled into a very low input impedance amplifier 287 connected to a tuned band pass filter that only allows the correct drive signal to be detected. The filter signal is then directed to a detector and output driver circuit 290 connected to the analog/digital input of the controller 310.

The use of a very low input impedance amplifier to receive the signal coupled through the liquid within a reagent bottle 25 tends to eliminate the effects of stray capacitances that might be received in parallel with the capacitance of the container. As an example, a typical capacitance that might be expected by pipette 18 to couple it to a 262 kHz signal source is on the order of 5 to 25 picofarads. However, given the location of the pipette within the chemistry instrument 24, it might encounter stray capacitances 292 from unidentified signal sources 291 that are an order of magnitude greater than that of liquid in a reagent bottle 25. If the amplifier 287 had high input impedance these stray capacitive values would be in parallel with bottle 25 and cause an attenuation of the signal measured at the tip of pipette 18. Further, since the stray capacitances 292 are unpredictable in value, the resulting signal strength would also vary unpredictably because the strays would result in a voltage divider network and the transfer function would be impossible to dependably predict.

To counteract this problem, a very low input impedance amplifier 287 is used to receive the signal from pipette 18 so that the shunt impedances of stray capacitances 292 are very large with respect to amplifier impedance. In effect this creates a current summing node for the signals so that all input signals are capacitively coupled into a virtual ground. This method allows stray capacitances of many times the capacitances produced within bottle 25 to exist, but they will not affect the load impedance of amplifier 287 since it is already very low. This feature allows extra bottles or an operator to be in close proximity to the container being sensed without confusing operation of the detection circuit. FIGS. 69 and 70 illustrate equivalent circuits when the network described above is measuring a typical reagent bottle capacitance shown at 279 and is connected to a very low input impedance amplifier 287 (FIG. 69) or to a high input impedance amplifier 277 (FIG. 70).

The significant increase in signal strength received from pipette 18 when it comes into contact with liquid within the reagent bottle 25, together with the known elevation of pipette 18 and reagent bottle 25 relative to the common supporting platform 238 of the chemistry instrument 24, permits workstation 30 to compute the remaining volume of liquid within the container, since the interior cross-section of each reagent bottle 25 is known and constant.

In addition to sensing fluid level, the detection circuit shown in FIG. 68 is also used with slotted conductive plate 276 to verify radial alignment of pipette 18 and/or to calibrate the elevation of the pipette tip relative to the supporting platform 238 for the equipment. The physical steps involved in such calibrations are described above with respect to the details of plate 276. The electronic results are quite similar to those used for sensing the level of fluid within reagent bottles 25 (or cups 35 and wells 36). However, because the pipette 18 will physically contact the conductive plate 276 if misaligned, and because contact between pipette 18 and plate 276 is used to detect the reference elevation of pipette 18 for calibration purposes, a minimum impedance is assured by resistor 283 in series with plate 276. Therefore, when such contact occurs, there will be a significant decrease in the detected signal level coupled between plate 276 and pipette 18, to allow calibration of the bandpass filter 288 without saturation of the A/D converter within microcomputer 310.

When checking for alignment of pipette 18, it is first lowered through the center of aperture 278 within plate 276. Pipette 18 then swings to one side and is stopped short of contact (if in alignment) with plate 276. The resulting signal received through pipette 18 is then checked to determine whether it remains above the signal that would be passed by the series resistor 283. If there has been no contact, pipette 18 then swings to the opposite side of aperture 278 and the measurement sequence is repeated.

Assuming that no contact with plate 276 is detected, pipette 18 is then moved further to the side and into contact with the end of aperture 278. This results in a strong signal being directed through the pipette 18. Probe arm 17 is next raised upwardly until this signal significantly decreases, indicating a gap between pipette 18 and plate 276. The detection of the end of pipette 18 is used to calibrate the elevation of the pipette tip relative to platform 238 and the system components fixed to it.

Accurate measurement of liquid volume within reagent bottle 25 and accurate radial and axial alignment of pipette 18 allows the pipette 18 to be lowered to a position directly above the inner surfaces within each container used in conjunction with the chemistry instrument 24 as necessary. This enables it to more completely remove liquid from within it.

Reagent Bottle Identification

Machine-readable identifying information is encoded at the bottom of each reagent bottle 25 upon a printed label 325 detailed in FIGS. 73 and 74. The label can be secured to the circular surface of the reagent bottle 25 by any suitable adhesive system.

Each label 325 preferably has a light surface background on which a contrasting pattern of dots are imprinted. While circular dots are illustrated in FIG. 73, other suitable dot shapes can be used as well.

The label pattern shown in FIG. 73 includes every possible dot location in the present encoding pattern. It is to be understood that the encoded pattern identifying a specific reagent bottle will display a unique arrangement of both dots and blank areas where the dots are now illustrated, the pattern being dependent upon the digital code representative of the encoded data. The code utilized on the labels 325 is a multi-bit binary code representing an identification code for a specific reagent bottle.

Identification label 325 includes a spaced pair of position reference dots 326 and 327 which define and orient a label area. Position reference dot 326 is a central position dot, designating the approximate center of the reagent bottle bottom surface. Position reference dot 327 is an orientation dot which is located radially outward from central position dot 326 to define a label orientation.

The label area is divided into a plurality of bit fields whose positions are defined by position reference dots 326 and 327. Each bit field maps to a single bit of the multi-bit binary bottle identification code. The binary value of each bit of the multi-bit binary identification code is determined by whether a bit dot 328 is present within the mapped bit field.

In general, position reference dots 326 and 327 have a minimum area and the bit dots 328 have a maximum area. The minimum area of position reference dots 326 and 327 is greater than the maximum area of bit dots 328 so that position reference dots 326 and 327 can be easily distinguished from bit dots 328. In the preferred embodiment, position reference dots 326 and 327 have a diameter of about 0.054". Bit dots 328 have a diameter of about 0.034".

The configuration described above produces a patten of 45 dots that can be effectively imprinted within a label area having a diameter of one half inch. Position reference dot 326 identifies the center of the pattern. Position reference dot 327 is located at the rim of the pattern as an angular index. The label data is encoded by smaller bit dots 328. The bit dots 328 are spaced on approximately 0.1" centers.

The mapping of information bits to label dots is indicated in FIG. 74. The dots designated by the digits 0-6 encode seven check bits. The label information is encoded by the dots designated by the digits 7-43, with dot 7 being the least significant bit. The forty-three illustrated bit dots 328 provide forty-three bits of digital data, which is sufficient to encode eleven decimal digits.

A conventional Hamming error detection/correction code can be used to encode the label information. Seven check bits are computed from the data bits and form a part of the label pattern. When the label is read, the encoding of the check bits allows the detection and correction of an error in any one of the bit locations about the label 325. Any single bit may be in error, but the encoded information on the label 325 can still be recognized correctly. If errors exist at any two bit locations, the existence of an error will be detected, but the information on the label cannot be decoded. If errors exist in more than two bits, the resulting information will be unpredictable.

The equipment for reading information encoded on labels 325 is diagrammatically illustrated in FIG. 75. Each reagent bottle 25 is held within the sample/reagent tray 15 at a location above the horizontal surface of well 240. Each label 325 can be indexed over one of the optical scanner ports 250 for label reading purposes. The optical scanner ports 250 each include a circular filter 330 that blocks entrance of room light while permitting passage of illuminating light directed to the label 325 from a location under the port 250.

The information encoded on labels 325 is read by a camera 332 in response to reflected light provided by a circumferential ring of light emitting diodes 334 directed toward the bottom surface of a reagent bottle 25. Camera 332, which is essentially a video camera, includes a lens system 335 positioned behind the ring of diodes 334. Lens system 135 focuses light from the bottom of reagent bottle 25 onto a receiving scanning matrix 336 of image sensors. In the illustrated example, the matrix 336 has a 192×165 pixel area capable of discriminating between the above-identified dot array.

The camera 132 conveys digital information to controller 312 from which a digitized image of the bottom of each reagent bottle 25 can be stored in memory. This image can then be electronically "rotated" about the center dot 326 and indexed relative to the rim dot 327 to orient bit dots 328 for electronic analysis. The electronic functions required in such an analysis are believed to be well-known in image-analyzing technology today. No further details are necessary in order to enable those skilled in this area of technology to construct and successfully use the described scanning apparatus and associated labels.

The unique labeling scheme described above allows for simple and quick decoding of reagent bottle identification data. Once the label has been oriented properly and broken into bit fields, only the presence or absence of a dot in that bit field need be determined. This is in contrast to many other types of labeling schemes in which indicia size or spacing is variable to represent coded information. In the scheme of this invention, all bit dot sizes and all spacing between bit dots remain constant, making for much simpler detection and decoding. Simple thresholding can be used within each bit field to detect whether a dot is present of sufficient area to constitute a bit dot.

Controller System

The computerized controller system for the various modules included within the chemistry instrument 24 is diagrammatically illustrated in FIG. 71. The control circuitry shown in FIG. 71 is that associated with a single chemistry instrument 24. Where two chemistry instruments 24 are utilized in a single installation, the illustrated components (other than workstation 30) will be duplicated for each instrument.

Scheduling of physical operations to be carried out in the chemistry instrument 24 is controlled by an instrument central processing unit (CPU) circuitboard 306. The instrument CPU board 306, located physically within workstation 30, is programmed to schedule the randomly available operations of the chemistry instrument modules as permitted by the status of its affected modular components and as required by a requisitioned assay. Board 306 includes a suitable microprocessor and memory devices for storing logic and scheduling programs required to operate the chemistry instrument.

The control system for each chemistry instrument 24 includes a distributed family of controller microprocessors located within its various modules. In the preferred embodiment shown in FIG. 71, there are seven microprocessor controllers associated with operation of the instrument components. Their respective operational functions and associated modular components are as follows:

Syringe Controller 308—directly controls operation of syringe motor 296. Controller 308 monitors the linear position of the syringe piston by means of signals supplied by optical sensor 300 (FIG. 65). It also operates the valves 303-305 associated with syringe 294.

Liquid Transfer Module Controller 310—moves probe arm 17 both vertically and angularly through use of operator 19. Photocell sensors 356, 357 and 358 associated with probe arm 17 and operator 19 (FIG. 76) provide signals indicative of the preset vertical and angular positions of probe arm 17. Controller 310 also maintains desired liquid temperatures for liquids in the tubing arranged along the probe arm 17 that leads to pipette 18 through monitored operation of heating element 375. It additionally controls operation of the capacitive sensing system shown in FIGS. 66-68.

Sample/Reagent Tray Controller 312—operates motor 16 to selectively position sample/reagent tray 15 about its axis. It monitors sensors 246 and 248 to accurately index tray 15 at a selected angular position for pipette access to a selected container. It also controls operation of the reagent bottle label readers located under the optical scanner ports 250 shown in FIG. 36. The sample/reagent tray controller 312 is further responsible for maintaining suitable reagent temperatures through selective operation of cooling elements (not shown) associated with tray 15 and is connected to sensor 256 (FIG. 36), which selectively detects the presence of cups 35 within a ring segment 26.

Data Acquisition Controller 314—Controls rotation and indexing of turntable 11 through operation of motor 12. Indexing information is supplied to it from sensors 74 and 139 adjacent to the turntable 11 (FIG. 13). Controller 314 also operates the elements included within optical system 14 and relays resulting absorbance and fluorescence data for tested samples.

Cuvette Delivery Controller 316—Operates the components of cuvette delivery module 13 through control of motors 86, 98, and 117, and stripper 103. It further provides temperature controls for heating and cooling devices (not shown) associated with turntable 11 for maintaining desired reaction temperatures during its operation.

Sample Tube Entry Port Controller 318—Governs operation of sample tube entry port 20. It receives signals from line of sight sensors 189 (FIG. 37), which are directed through apertures 186 in ram 140 to detect the presence of each draw tube as it is manually inserted into the chemistry instrument 124. Controller 318 also monitors all of the various sensors that limit and control movement of ram 140 and cover 160, and coordinates movement of the components within sample tube entry port 20 with movement of probe arm 17. In addition, it controls operation of scanner 144 that reads information from bar coded labels or other optical data on each incoming draw tube. Controller 318 further monitors miscellaneous activities required for effective use of the chemistry instrument 24, including conditions of the diluent supply within container rack 28 and the status of waste liquid container 302, segment access port 7, tray access cover 8, cover 160, various access doors, and the cuvette disposal container.

Ion Specific Electrode (ISE) Controller 320—Controls operation of the ISE module 38 to selectively test samples for the presence of electrolytes such as sodium, potassium, chloride, lithium and calcium. The operational functions of this controller are dictated by conventional operation of the ISE module 38 and are well known to those skilled in such technology.

In addition to the listed controllers, the chemistry instrument 24 is provided with a power and communications interface 322 for all the modules included within it and with a flash lamp supply 324 that powers and operates the lamp 190 within optical system 14. The power and communications interface 322 is operatively connected to the instrument CPU board 306 and to a suitable power supply 323 capable of providing the electrical power needed by the various motors and electronic components of the chemistry instrument 24.

METHOD OF OPERATION

Overview of Method

The method for operating the chemistry analyzer 24 basically entails a number of randomly selectable steps. Operation of the chemistry instrument 24 is timed about a repetitious sequence of steps for cyclically transferring liquid from any selected container on the sample/reagent tray 15 to any selected cuvette 10 on the turntable 11, mixing liquids within the cuvettes on the turntable by turning it about the first axis, and rotating the turntable about the first axis. The timing of these steps is graphically depicted in FIG. 72.

The operational cycles of all components are timed to the repetitious cycle of operation of turntable 11. The turntable 11 is randomly indexed to a stationary angular position about the first axis indicated at X—X (FIG. 13) with a selected cuvette 10 positioned at cuvette access station A. The turntable 11 is held stationary by motor 12 for a period during which a disposable cuvette 10 can be delivered to the turntable 11 by operation of the cuvette delivery module as liquid is being discharged into another cuvette by operation of pipette 18. Delivery of a new cuvette 10 also displaces a spent cuvette, which is directed into a disposal container in the instrument. Turntable 11 is then turned about the axis while mixing or centrifuging the contents of cuvettes 10 mounted to it.

As the contents of cuvettes 10 are being centrifuged within turntable 11, the steps involved in analyzing their contents at a location adjacent to the turntable take place within the optical system shown in FIGS. 24-31. The mechanically movable filter 205 is repositioned and data is transmitted from the optical testing module while turntable 11 is stationary.

Liquid samples and reagents are supplied to turntable 11 by indexing the sample/reagent tray 15 about a second axis parallel to and spaced from the first axis to a stationary angular position with a selected container positioned at a container access station C. By moving probe arm 17 and pipette 18 along an arcuate path centered about a third axis that is parallel to the first axis and intersecting both the cuvette access station A and the container access station C, the chemistry instrument 24 can selectively transfer liquids from containers positioned on the tray 15 at the container access station C to cuvettes 10 positioned on the turntable 11 at the cuvette access station A. The workstation 30 is programmed so that the step of moving the pipette 18 provides randomly accessible transfers of liquid from any container on the tray to any cuvette on the turntable in the time during which the turntable 11 is stationary.

The method of sample delivery to chemistry instrument 24 involves the steps of receiving a manually placed draw tube 27 beneath a puncture tube 161, moving the draw tube between a lowered position wherein the draw tube is clear of the puncture tube and a raised position wherein the puncture tube forms a temporary opening through a closure on the draw tube, and subsequently inserting the pipette 18 coaxially through the opening in the closure to access the interior of the draw tube. If further comprises the step of detecting the level of liquid in the draw tube 27 as it is approached by the pipette 18, using the capacitive sensing system shown in FIGS. 66-70.

Where potentiometric tests are desired, the method further involves the steps of transferring a liquid sample from a container on the sample/reagent tray 15 positioned at the container access station C to ISE station E along the arcuate path of the pipette 18 and subsequent performance of potentiometric (ISE) tests on the sample.

Workstation 30 is also programmed to monitor operation of the chemistry instrument by detecting the level of liquid in each container on the sample/reagent tray 15 by capacitive sensing as it is approached by pipette 18, capturing information from indicia on containers on the tray 15 identifying the container and its contents, maintaining a current record of the amount of liquid within the containers on tray 15, and recording the elapsed time that has occurred since introduction of each sample and containers.

Additions and refinements to the method of operating the analyzer will be spelled out in the following description, which details operational steps programmed into workstation 30.

Requisition Entry

Tests involving both patient samples and quality control samples are initiated by entering requisitions. The method of entry and handling of results are different for the two types of samples. A listing of incomplete requisitions for outstanding samples waiting to be tested can be viewed by the operator at any time on the workstation monitor 31 to facilitate processing of the current work backlog.

The system maintains a database listing individual patients and their requisitions. A patient can have more than one requisition. Each patient requisition is given an accession number, which can be automatically assigned by the system. Each new accession number must be unique among the set of requisitions in the system data base.

A patient requisition may be designated as "stat", or highest priority, by use of a special stat key on keyboard 32. The stat key acts as a toggle. Pressing the key once gives the requisition a stat priority, which is indicated on the requisition display screen. Pressing the key again changes the priority back to routine, or non-stat.

Patient sample tests can be entered in requisitions by using test and panel mnemonics. At least one non-derived test must be placed in a requisition. Only one sample type is allowed for each test listed in a requisition.

Tests can be added to a requisition at any time, even after the requisition becomes complete. Editing of a completed requisition, either by adding tests, deleting tests, or changing result values, will cause the requisition to be reprinted or retransmitted to an external computer, if enabled.

Derived tests may be specified in a requisition. All tests required by the derived test are entered automatically when the derived test is requested.

Quality control requisitions are specific for one chemistry instrument 24 connected to the workstation 30. Only tests that are defined for the control sample (in pre-programmed quality control parameters) are allowed in a quality control requisition. All that is necessary to enter a quality control requisition is to specify a control sample and identify the pre-programmed quality control tests to be carried out with respect to it. The requisition date and time will be automatically stored by the workstation 30.

Supply of Materials

Individual patient samples can be introduced by use of either the sample tube entry port 20 or the segment access port 7. Samples introduced at the sample tube entry port 20 are identified by bar code scanner 144. Identification of samples introduced in cups 35 at the segment access port 7 must be manually entered on keyboard 32.

There are three methods by which patient samples may be introduced. They can be introduced individually within draw tubes 27 placed in sample tube entry port 20, from which the instrument will transfer aliquots to load the various tests desired with respect to the sample. Alternatively, sample ring segments 26 can be filled with removable cups 35 containing various patient samples and introduced directly at the segment access port 7. The third method involves placement of individual sample cups 35 containing patient samples into a ring segment 26 already in the instrument, again using the segment access port 7.

These three methods are not mutually exclusive. The operator may use a given method at any time, depending upon the immediate workload.

A patient draw tube 27 can be manually placed within the sample tube entry port 20 whenever it is idle. If a bar code label 69 is on the draw tube, the workstation 30 will try to match accession data scanned from the label with a patient requisition accession number. Assuming that matching accession data is found, the system will close cover 160 and proceed to transfer an aliquot of the sample to a clean well 36 in a ring segment 26. Enough volume of sample will then be taken to load all of the tests in the outstanding requisition for the identified patient.

If no matching accession data is found, or if there is no label on the draw tube 27, workstation 30 will wait for the operator to manually identify a requisition by operation of keyboard 32 before transferring liquid from the draw tube 27.

After a sample transfer from draw tube 27 has been completed, the operator can manually remove the draw tube 27 from within sample tube entry port 20 and insert another draw tube to repeat the process.

In normal operation, a test on an aliquot will begin loading into cuvettes 10 in the turntable 11 as soon as the sample transfer at the sample tube entry port 20 has been completed, unless the operator has immediately placed another draw tube 27 within it. The resulting test loading activity very briefly ties up operation of probe arm 17 and pipette 18 before they are free to perform another sample transfer.

When a substantial number of draw tubes 27 require processing, a transfer priority mode of instrument operation is activated in response to timely introduction of successive draw tubes into the chemistry instrument 24. In this sample transfer priority mode, the chemistry instrument 24 does not start loading any non-stat tests, thus leaving probe arm 17 free to respond as soon as possible to samples introduced at the sample tube entry port 20. The probe arm will still load stats and service any incubation timeouts for load sequences then in progress.

If a preselected minimum time has passed without a new sample having been placed at the sample tube entry port 20 while in the sample transfer priority mode, chemistry instrument 24 will automatically return to its normal mode of operation. This prevents it from being accidentally left in the sample transfer priority mode.

It is possible that a given patient requisition cannot be run on a single chemistry instrument when two chemistry instruments 24 are connected to workstation 30. The sample would then have to be introduced at both instruments. Each chemistry instrument 24 will then take an aliquot based on the tests it can run, identified by the reagents present in each instrument and relevant calibration data.

The aliquot taken by the first instrument 24 will include enough volume to run all of the tests for which requirements are present within it, plus the tests for which neither instrument has requirements. The second instrument will take a similar volume calculated in the same manner. This allows the user to satisfy the missing requirements at either instrument after both introductions. Either instrument will then have sufficient sample volume to run the remaining tests.

Before opening any door or cover on the chemistry instrument 24, the operator must initiate an instrument access request through keyboard 32 of workstation 30. This will manually interrupt operation of the instrument for purposes of replenishing its resources. A visible indicator on the workstation monitor then indicates that operation of the instrument is paused until such operations have been carried out. No further tests will be initiated until after the instrument access has been completed and operation is restarted by instructions keyed into keyboard 32.

Introduction of patient samples into the chemistry instrument 24 can be effected through use of draw tubes 27 or cups 35. Quality control samples are introduced by use of cups 35 only. The chemistry instrument 24 is configured to accept labeled or unlabeled draw tubes 27 in the sample tube entry port 20. If labeled, information on the draw tube 27 will provide an accession number to match a patient test requisition residing in memory within the workstation 30. If the draw tube 27 is unlabeled, the instrument operator must manually identify the patient test requisition before the desired tests will proceed.

Similarly, patient samples introduced in individual cups must be accompanied by operator-provided information identifying the patent test requisition. Preloaded patient samples can also be introduced within cups 35 in a ring segment 26. In this instance, the identification of patient test requisitions can be accomplished manually by the instrument operator or automatically through a labeling system (not shown) readable by the workstation 30.

If there is no available cup location on sample/reagent tray 15 when a Cup sample entry request is made, the operator is so notified by an appropriate message displayed on monitor 31. In this case, the operator must then review a sample ring status display and specify which active cup 35 (if any) is to be replaced. If there is no cup ring segment 26 on the tray 15 at the time in question, one must then be introduced.

When the operator is ready to place a preloaded cup segment 26 in the chemistry instrument 24, it is referenced by data input from the keyboard 32, using its segment identification. Workstation 30 will then search for a ring segment position on the sample/reagent tray 15 where the ring segment 26 can be placed without removing another ring segment having active wells or cups.

If a location is available, the chemistry instrument will position tray 15 to locate it under the segment access port 7. The segment access port 7 is then operated in the same manner as for sample cup introduction. The operator must manually remove an existing ring segment from tray 15 and place the new ring segment on it.

If there is no available ring segment location when such a request is made, the operator will be notified by an appropriate message displayed on monitor 31. In this case, the operator must review a sample ring status display and specify which active ring segment 26 (if any) is to be replaced.

Quality control samples can be introduced either in individual cups 35 or in cup ring segments 26. In both cases the introduction process is the same as for patient samples. A quality control requisition is identified for each cup containing such a sample. Quality control samples can be placed in a cup ring segment 26 along with patient samples. Since quality control requisitions are specific for a particular chemistry instrument 24, the software loaded into the workstation 30 must check to assure that the requisitions are not run on the wrong instrument.

Calibrators and correctors for photometric tests can also be introduced in cup ring segments 26 by Sample Entry procedures. Except for their identification, the introduction process is the same as for patient samples or quality control samples. Calibrators and correctors are identified by predefined names in a programmed data base loaded within workstation 30.

ISE tests are calibrated using on-board standard solutions in dedicated containers. They are not introduced in cups 35 or cup ring segments 26.

Access requests are used for servicing samples previously placed in the chemistry instrument 24. The access requests include Cup (for removal of a cup 35 or replenishing its contents), Segment (for adding or removing ring segments 26), Reagents (for access to the reagent bottles 25), Hopper (for replenishing cuvettes 10), supply and waste cuvettes 10), and Containers (for replenishing supply and waste containers).

To utilize the segment access port 7 for a Cup access, which involves the removal or replenishing of a sample within a cup on the chemistry instrument 24, the operator utilizes keyboard 32 to make a Cup access request and to identify a requisition.

Workstation 30 will then position a selected cup on sample/reagent tray 15 to a visual mark at the segment access port 7. Information will be displayed on monitor 31 to signal permission to manually open port 7. The operator then opens port 7 and accesses the selected cup.

After completing a Cup access, the operator must manually close port 7 and enter an indication on keyboard 32 that the Cup access has been completed. The instrument will then verify the absence or presence of a cup. It will also verify that closure of segment access port 7 has occurred.

The workstation 30 is programmed to generate a calibration ring segment map upon request. This is a display of a segment with calibrator and/or corrector cup locations identified that are available to receive liquids needed for the chemistry instrument 24 to carry out its requested calibration or correction workload. Patient samples and/or quality control samples can be added to the ring segment 26 at this time if desired.

During a Segment access, the operator has the ability to remove cup or well ring segments 26 and to add empty replacement segments. The operator can identify one or more segments 26 for substitution purposes by utilization of keyboard 32.

Cup ring segments are identified by visual labels (not shown). Each cup position has a requisition associated with it. A segment identification is required for each segment defined. The identification data should correspond with numerical information on the label affixed to the particular ring segment 26.

A request for a Segment access to add a well ring segment 26 is similarly initiated by manual entry at keyboard 32. Only clean, unused well ring segments 26 should be placed within the chemistry instrument 24 by an operator during its usage.

Following entry of a request for a Segment access to insert a well ring segment, the controlling software will angularly position sample/reagent tray 15 about its axis to locate a spent ring segment 26 or a vacant ring segment position under the segment access port 7. It will then illuminate an indicator on a panel visible at the front of the chemistry instrument 24. The operator can then open the port 7 and mount the clean well ring segment 26 on the awaiting tray 15.

If there are no inactive ring segments 26 that can be replaced, the operator will be notified by a message displayed on monitor 31. In this case, the operator must review a sample ring status display and specify which existing ring segment 26 (if any) is to be replaced.

The system allows the user to remove or replace ring segments 26 or cups upon request during each Segment access. It will not allow removal of an active segment or cup (one containing a sample with an incomplete test) without a warning.

Reagents are introduced into the instrument by accessing the sample/reagent tray 15, using a Reagent access procedure. Tray access cover 8 provides operator entry to the sample/reagent tray 15. The operator initiates access by pressing appropriate keys on keyboard 32. When this occurs, the chemistry instrument 24 will first complete any liquid transfers in progress and then index tray 15 about its vertical axis before indicating permission to open the cover 8. After cover 8 has been opened and closed, the software within workstation 30 will check the labels on the reagent bottles 25 before using any liquids from them.

An operator can add new cuvettes 10 to the chemistry instrument 24 at any time by initiating a Hopper access, which is manually entered at the keyboard 32 of workstation 30. When a cuvette insertion is requested, the instrument will position the cuvette magazine 75 of the cuvette delivery module 13 to locate an empty slot within it under the cartridge guide 102 and illuminate an indicator at the front of the chemistry instrument 24. The operator can then insert a cartridge 40 filled with cuvettes 10.

The chemistry instrument 24 will sense when insertion of new cuvettes has been completed as the cartridge 40 is withdrawn, and will proceed to the next empty slot in the cuvette magazine 75. This will be repeated until there are no more empty slots within the magazine 75 or until the operator terminates the process at keyboard 37. A pause indicator will be visible on monitor screen 31 until the cuvette insertion procedure has been completed.

Each chemistry instrument 24 is supplied with a diluent (water) container in its container rack 28. Rack 28 also holds containers filled with ISE Standard solutions as required. Each chemistry instrument 24 also includes one or more waste liquid containers 302 (FIG. 1) connected to the wash/alignment station 21 and to the ISE module 38. A Containers access routine to replace or service these containers is initiated by the operator through use of keyboard 32.

Each container in the container rack 28 interacts with a sensor within the chemistry instrument 24 that indicates when it is empty or absent. A similar sensor indicates when the waste liquid container 302 is full or absent. If any of these sensors is in violation, the chemistry instrument 24 will stop all subsequent loading activity for both photometric and ISE tests. If the violation occurs during operation, the operator will be notified by a message displayed upon the monitor 31 and all tests, calibrations or corrections in process are completed, but no new procedures will be initiated until the situation has been rectified.

Since the waste container 302 receives fluid from ISE module 38, no ISE fluidic activity (including standby mode cycling) can take place when it is in violation.

The container that supplies ISE Standard A solution to the ISE module 38 also has a sensor that indicates when it is empty or absent. If this sensor is in violation, the operator will be notified and the instrument will stop all ISE module activity (including standby mode cycling), but photometric operations being actively carried out in the chemistry instrument 24 can continue until completed.

The container that supplies ISE Standard B solution to the ISE module 38 does not have a sensor. Standard B solution in this container is only used during ISE calibrations. If it becomes empty, the condition can be detected by the ISE system fluid sensor. The operator will then be notified. The chemistry instrument 24 will not then perform any ISE calibrations until this situation is rectified.

In order to service any of the supply containers included in the chemistry instrument 24, the operator makes a request for a Container access at the keyboard 32 of workstation 30. The chemistry instrument 24 must then reach an idle state where none of the container contents are needed for partially completed procedures. The monitor 31 will then provide a message indicating that the containers are accessible. The operator must indicate to the workstation 30 when the access is completed, again by use of keyboard 32.

Activity Scheduling and Execution

The modular operational features of the liquid-handling components included within the chemistry instrument 24 permit software control of the instrument in a random fashion dictated solely by current requisition of assays and the current status of the instrument components. Scheduling software, residing in the memory of the instrument CPU board 306, is programmed to prioritize operations of the various modules for maximum operational efficiency at any given time.

Each chemistry instrument 24 has a workload comprised of one or more tasks. A task can be a calibration, a correction, or a test on a patient or quality control sample. A task can be scheduled only when all requirements for loading are present. Requirements include reagents, dilution buffers, and clean ring segment wells 36. If any requirement is missing for a specific task, it is placed "on hold," and is not scheduled.

A patient/quality control test is put on hold if a calibration or correction for that test is required or has been placed on hold. A calibration/correction task is put on hold if any required calibrator or corrector is not present in a ring segment 26. Each calibrator or corrector in the instrument is available to be used for any task that requires it.

Samples introduced into the system each have a set of tests that are to be run on them. Each patient sample and quality control sample is associated with a requisition detailing the required set of tests for that sample.

Scheduling software within workstation 30 supports a priority of tasks in determining which task to schedule next. Tasks are grouped into two priority classes, stat (immediate priority) and non-stat. The system will never start loading a non-stat task when a stat test is waiting.

Calibration and correction tasks are given stat priority if any stat sample test is dependent upon them. Within each class of tasks, calibration and/or correction tasks are always scheduled to begin before patient or quality control tests dependent upon them. However, a given test can be scheduled before the corresponding calibration and/or correction tasks have been completed for that test. If the calibration and/or correction task subsequently fails, any test in progress will then be aborted.

The priority schedule is designed to run tests on samples in a first-in-first-out (FIFO) manner. Calibration and/or correction tasks within a stat/non-stat class are scheduled in the order requested by the operator. Patient/quality control tests are scheduled according to the time of introduction of the patient or quality control sample. Patient or quality control samples introduced together in a cup ring segment 26 are given preassigned priorities based on their positions in the ring segment.

It is often possible for the chemistry instrument 24 to minimize overall testing time by sequentially loading a specified reagent into cuvettes containing several samples requiring a given test. This reduces the number of times the pipette 18 must be given a long wash to prevent reagent carryover from one test to another. When practical, the software will batch tests together in this way, even though this may cause tests with respect to a more recently introduced sample to be completed sooner. In no case should such optimization procedures be allowed to result in delaying completion of the stat workload.

Potentiometric (ISE) tests require a relatively long cycle time (about a minute). During this time, the probe arm 17 is free to load photometric cuvettes 10 in the turntable 11. For this reason, test batching is not applied to ISE tests.

The software within workstation 30 will estimate the total time required to load and analyze the current photometric and ISE workloads. If the ISE workload is dominant, an ISE load is scheduled as soon as the ISE module is ready. This can interrupt a photometric test batch and cause an extra between-reagent wash for pipette 18. If the ISE workload is not dominant, ISE loads should only be scheduled between photometric test batches, where they will not result in the need for an extra wash.

Priority of Instrument Actions

All of the various physical actions performed by the instrument are prioritized.

Top priority is given to performing loading operations that follow an incubation period. This promotes uniformity of analysis by preventing a test from incubating over an excessively long time period.

Second priority is given to responding to an operator's request to introduce a sample aliquot at the sample tube entry port 20. This assures a timely stat response and minimizes operator involvement during such a sample introduction.

Third priority is given to fluid transfers to the ISE module 38. This is used to support operation when the ISE workload is dominant.

Fourth priority is given to completing required cuvette loading sequences at turntable 11 for tests whose loading sequence is partially completed. It is important not to let too much time pass between fluid transfers to a given cuvette 10. This priority is suspended during loading of tasks scheduled as a batch. In this case the loading sequence steps are batched to avoid unnecessary between-reagent washes.

Fifth priority is given to beginning the load sequence for a test, calibration, or correction task. The task loaded next from among these requirements is selected according to the scheduling priority rules.

The lowest priority is given to background tasks that the system performs when it is otherwise idle. For example, if the turntable 11 should stop when no fluid transfer is scheduled to a cuvette 10, the turntable 11 might be indexed about its axis to permit a new cuvette 10 to be inserted. Another background task might be blanking of the screen on monitor 31 if a key has not been pressed on keyboard 32 over a preset period of time.

The scheduling software also assures that each new cuvette 10 is in place in the turntable 11 for at least a minimum length of time prior to being loaded. This assures that it will reach thermal equilibrium before being used.

Resource Checking

The software within the workstation 30 is programmed to constantly monitor the resources of the chemistry instrument(s) 24 associated with it. "Resources" refer to the items which the operator must supply for operation of the instrument. They include reagents, calibrators, correctors, patient and quality control samples, cuvettes 10, sample well ring segments 26, cups 35, ISE standard solution containers and the diluent and waste containers. Resources are periodically checked by the workstation 30 both before and during testing.

Each reagent bottle 25 in the sample/reagent tray 15 is identified by a machine-readable label. The label contains the bottle identification, lot code and serial number. The identification is specified along with each reagent's name in the bottle data stored within workstation 30.

When an operator adds workload to a chemistry instrument 24 (by requesting a patient or quality control test, a calibration or correction, or instrument utility functions) the controlling software in workstation 30 will determine whether resources in the instrument are adequate to fulfill the request. At this time the software checks for required reagents, buffers and calibrators or correctors. The system also checks to see if a calibration or correction is required or has been placed on hold. If any requirement for a requested test is not met, the operator receives a warning and the test is placed on hold.

If one or more requirements for a test is missing, sufficient aliquot volume will be taken to load it at a later time after the requirements are met. For instance, if a missing reagent is manually placed within the system at a later time, the test will then be automatically taken off hold and carried out as requisitioned.

The software associated with each chemistry instrument 24 will keep track of the working lot number for each reagent bottle 25 defined in the stored system bottle data. If a bottle is found with a new lot number, a calibration will be required for any test that uses it.

The system monitors all resources during testing. If any resource become unavailable during a task, the affected tasks are aborted and/or put on hold, and the operator is notified.

The fluid sensing system associated with pipette 18 and the probe arm 17 will provide constantly updated measurements of the volume of liquid in each reagent bottle 25 or sample cup 35 whenever it is probed. This is done by detecting the level of the surface of the liquid, and knowing the dimensions of the containers.

A working lifetime is specified for each reagent within the controlling software within workstation 30. The time of appearance of a bottle 25 is tracked for this purpose. It is assumed that each reagent bottle is opened or the reagent within it is reconstituted just prior to its initial placement within the sample/reagent tray 15. The working lifetime of each reagent provided in the sample/reagent tray 15 is continuously monitored during operation of the chemistry instrument 24.

A reagent bottle 25 can be removed from a particular chemistry instrument 24 and later reintroduced within it. It is then recognized by its identification lot number and serial number and matched to its working life timer. The operator will receive a warning on monitor 31 if any bottle has exceeded its working lifetime.

If two bottles of a reagent are present in a chemistry instrument 24 and the primary (working) bottle becomes depleted, subsequent loading is resumed with automatic selection of the secondary bottle.

If a chemistry instrument 24 has no clean ring segment wells 36, and any workload tests require one, such tests will be placed on hold. The operator will be notified of this fact by a message displayed on the workstation monitor 31. Other tasks that do not require a clean well 36 will remain scheduled.

When the number of cuvettes 10 available in the cuvette dispenser module 13 falls below a predetermined minimum value, the operator will be notified of this condition by a message displayed on monitor 31. When the supply of cuvettes in module 13 has been depleted, photometric tasks can still be scheduled if a sufficient number of clean cuvettes 10 are in the turntable 11. ISE tasks will remain scheduled.

The contents of supply containers within container rack 28 are continuously monitored by light-responsive sensors. If the liquid within any one of them becomes depleted the operator will be notified of this condition by a visual signal on workstation monitor 31. All operations requiring the depleted liquid will then be suspended.

The software within workstation 30 also keeps track of the volume of liquid remaining in each well 36 or cup 35 of the ring segments 26. If any of these materials is short, the operator will be notified. It further maintains a record of how long each patient or quality control sample, calibrator or corrector has been in the chemistry instrument 24. If any material has been in the system beyond an acceptable length of time, it will be treated as if it were short.

Loading Sequences

Photometric Tests

The controlling software within workstation 30 activates the components of each chemistry instrument 24 to provide a variety of separate steps which are grouped into a loading sequence for each photometric test. This requires specified sequences for the loading and incubation of liquids within the cuvettes 10 in turntable 11.

The single pipette 18 loads samples, diluent, buffers and reagents. Samples are loaded into specified reaction cuvettes 10 and/or the ISE module 38. Up to four reagents or buffers can be loaded singly or in combination. A volume of diluent supplied to pipette 18 by the syringe module 293 is specified as wash liquid to assure complete dispensing of reaction fluids. The total of all volumes loaded must be within an acceptable range.

The choice of a loading sequence is determined by the requisitioned test. The loading sequences are performed prior to the start of the timed data acquisition interval for photometric tests, as illustrated in FIG. 72.

The loading sequences are as follows:

Load One Fluid—This command identifies a particular fluid to be loaded into a cuvette 10. The fluid can be sample or reagent. The reactant fluid volume and the volume of diluent, if any, are retrieved as specified by stored test parameters.

Load Two Fluids—Two fluids and diluent are drawn sequentially into the pipette 18 and dispensed together into a waiting cuvette 10.

Incubation—An incubation period may be interjected between other steps in the loading sequence for a given cuvette 10. The incubation time is specified within this step. Only one incubation is permitted in the loading sequence for each cuvette 10.

Take Internal Blank Reading—One internal blank reading may be specified as a step in the sequence. This reading is not a part of the normal data acquisition timing but the data is used in result calculations. The reading is taken at the reaction wavelength. The volume of fluid loaded before the blank reading must be above a preselected minimum value.

Potentiometric Test Loading

Potentiometric (ISE) tests are loaded using a sequence that is not user specified. The dilution ratio can be specified by the operator in the test parameters entered through keyboard 32. A volume of sample will then diluted with diluent into a well 36. The diluted mixture is subsequently transferred to the ISE module 38.

FIG. 72 illustrates the relative timing of operations of turntable 11, probe arm 17, cuvette dispenser module 13 and optical system 14 required to accommodate the repetitious predetermined cycle of operations carried out on turntable 11.

The turntable 11 is initially held stationary at the beginning of each of its operational cycles. Its motion is initiated by a mix cycle, when it is either oscillated in reverse angular directions or intermittently turned in one angular direction. It then accelerates to a spin condition. This is followed by deceleration to a stationary condition.

In an actual physical embodiment of the chemistry instrument 124, the entire cycle of movement of turntable 11 is repeated every 10 seconds. The spin cycle is approximately four seconds in length. The remaining components of the turntable cycle as illustrated in FIG. 72 are not illustrated at any defined time scale.

All movements of probe arm 17 must be synchronized so as to make it available for dispensing of fluids to cuvettes 10 on turntable 11 during the period while turntable 11 is stationary. At all other times probe arm 17 need not be tied to any specific schedule and need not perform functions pertaining to the turntable 11.

As an example, unless a step involving dispensing of fluid to a cuvette 10 is required by current requisitions of assays, probe arm 17 is free for aliquoting from a draw tube 27 at the sample tube entry port 20, or for either long or short wash cycles at the wash/alignment station 21 or for alignment checks at the same station.

Similarly, the cuvette dispenser module 13 must insert individual cuvettes 10 into turntable 11 during the time period in which turntable 11 is stationary during each operational cycle. At all other times the motors within module 13 can be operated in preparation for the next insertion of a cuvette 10 as required by outstanding requisitions for assays.

Operation of the optical system 14 also requires synchronism with the spin cycle of turntable 11. If fluorescence polarization readings are required in addition to absorbance readings, filter 205 must be moved into the optical path during the spin cycle. Data can be transmitted from the optical system 14 during the remainder of the turntable cycle, and filter 205 must again be moved if absorbance readings are to be included within assays of a subsequent turntable cycle.

Turntable 11 constantly repeats its cycle as illustrated in FIG. 72 as long as there is an active cuvette 10 within it. In this respect, an "active cuvette" means one containing liquids on which an assay has not yet been completed.

The programmed logic within instrument CPU board 306 converts workload requisition instructions into a sequence of electromechanical actions by control of the described modular components. Workload is scheduled and executed in a random fashion according to a set of defined priorities. As used herein, "workload" consists of calibration or correction runs, and patient or quality control test runs or assays.

A "run" consists of a sequence of fluid transfers. A run will only be scheduled when all materials needed to complete it are present within the chemistry instrument 24. Data acquisition takes place automatically after the specified fluid transfers have been completed.

There are three independent tasks involved in any activity scheduling and execution: status maintenance, fluid transfer scheduling and fluid transfer execution.

Status Maintenance

Each type of pending run requires a defined set of reagents. A software background loop routine (background status maintenance task) continually checks requirements for the pending workload at all times that the instrument 24 is powered. As one example, calibration/correction runs require calibrators and/or correctors in the wells 36 of ring segments 26. Similarly, if a test requires predilution, clean wells 36 will be required for this purpose.

To run a patient or quality control test, it must be calibrated (if the test uses calibrators). If a calibration run is in progress, the system will assume that the calibration will succeed. If it fails, any tests scheduled on this assumption are aborted. If a calibration or correction has been requested for a particular assay, no patient or quality control runs are started for that assay until the calibration/correction run has started.

The workload for the instrument at any given time is represented by the set of pending tests associated with samples in the cups 35 and wells 36 of ring segments 26, plus a set of calibrations which have been requested for the instrument 24.

A pending run has a status of "on hold" if the fluid requirements for it to be performed are not present in the instrument. When all requirements are presnt, the run is "waiting" and is then eligible for scheduling.

The background status maintenance routines of the instrument software continuously check requirements for all on-hold runs. It changes them to waiting status as this becomes appropriate. Such constant status monitoring allows chemistry instrument 24 to start performing any workload for which the requirements are satisfied, and allows all outstanding requirements to be satisfied asynchronously.

Fluid Transfer Scheduling

System activity scheduling involves setting up pending fluid transfers required by scheduled operation of the chemistry instrument 24. There are two basic types of fluid transfers:

Sample aliquot transfers—These are scheduled when the operator has presented a draw tube 27 at the sample tube entry port 20.

Cuvette load sequence transfers—These are set up when a run is scheduled. A run involves operations carried out with respect to one or more cuvettes 10.

Each cuvette 10 within turntable 11 requires a load sequence, which is a series of fluid transfers to it. These are further divided into three classes: transfers to clean cuvettes (the first step in a load sequence), transfers to active cuvettes (subsequent steps in multi-step load sequences) and transfers to incubating cuvettes.

Incubation service transfers must be carried out at a particular time to properly carry out the load sequence and have highest priority in fluid transfer sequences.

ISE load transfers are set up if a sample must be diluted before a run is scheduled on it. ISE loads cannot be batched, since the ISE analysis time typically requires 60 seconds between loads. Executing an ISE load while a batch of cuvette loads is in progress would diminish the benefits of batching, since an intervening long wash is required.

The system considers scheduling a run if there are no fluid transfers awaiting execution except for incubation service transfers that do not require immediate execution. The highest priority run is selected from the "waiting" workload as follows:

(1) Top priority is given to calibration or correction runs that must be run before a stat test can be run.
(2) Second priority is given to stat patient samples.
(3) Third priority is given to any other calibration or correction runs.
(4) Last priority is given to non-stat patient or quality control test runs.

Once a run is selected, if any dilutions of liquids present within the cups 35 or wells 36 of ring segments 26 are required, they are scheduled. Otherwise, the load sequence is scheduled for each cuvette 10 required for the run. If the highest priority test is an ISE test, only one transfer is scheduled for it.

Identical fluid transfers are scheduled to be executed consecutively. This occurs if more than one run for the same assay is waiting in the workload, or when a calibration or correction uses multiple reaction cuvettes. The pipette 18 does not require a long wash between like transfers since reagent carryover of fluid presents no problem, so it is advantageous to load several cuvettes 10 in parallel by executing each first step, then each second step and so on. After a run is scheduled, the rest of the workload is scanned to fill out fluid transfer batch groups. However, non-stat loads are not batched with stat loads.

The system will constantly estimate the total time required to run both the photometric and ISE workloads. If the ISE workload will take longer, the system will interrupt a batch of cuvette loads as soon as the ISE module is ready for a sample. Otherwise, the system only schedules ISE loads between batches of cuvette loads. This optimizes the overall time to completion of the combined workload. Such optimization is limited so that a non-stat run does not delay execution of a stat run.

Fluid Transfer Execution

The fluid transfers, once scheduled, are executed according to a priority scheme as follows:

Top priority is given to execution of cuvette loads for incubation service, since an assay must be aborted if its incubation is allowed to go too long. The load sequences are scheduled so as to avoid conflicts where more than one incubation would be serviced at a time.

Second priority is given to execution of sample aliquot transfers. This avoids delaying the operator during introduction of samples.

Third priority is given to loading cuvettes, transfers to the ISE module 38, or dilutions required within wells 36 in the ring segments 26. These transfers are carried out in the order they have been scheduled.

When a higher priority transfer interrupts the execution of a batch of cuvette loads, and the batch in progress is a set of transfers to clean cuvettes, the batch is broken up. A long wash is then performed before commencing the next cuvette load. Any load sequence transfers belonging to tests that have not started loading are then canceled. They will be rescheduled at a later time. This is done since it is more important to finish loading partially loaded cuvettes 10 within turntable 11 than to start loading new assays.

Cuvette Handling on the Turntable

Once the load sequence is completed for a cuvette 10, its analysis sequence begins. The timing of data acquisition is a task independent of loading, since the pipette 18 is only granted access to the cuvettes 10 in turntable 11 between analysis intervals (see FIG. 72).

There are five types of cuvettes 10 in the turntable 11: newly inserted cuvettes reaching thermal equilibrium, warmed cuvettes ready to load, cuvettes in their load sequence, cuvettes in their analysis sequence and spent cuvettes ready to be replaced with new ones.

To achieve optimum throughput, it is important that the system should be able to load cuvettes 10 within turntable 11 as fast as possible. This requires that there should always be at least one clean warmed cuvette in the turntable 11. To achieve this objective, spent cuvettes must be replaced with clean ones as soon as possible.

Insertion of new cuvettes is a background task, operating at a low priority. When the turntable 11 and the probe arm 17 are both idle, cuvettes 10 can be inserted into turntable 11 by the controlling software at will. While the system is running, however, insertion can only take place while turntable 11 is stopped between data point intervals.

The indexed stopping position of the turntable 11 is determined by the upcoming needs of the probe arm 17, since loading liquids into the cuvettes within turntable 11 has a higher priority than does the insertion of cuvettes.

A cuvette 10 can only be inserted into turntable 11 in two cases:
1) When probe arm 17 is busy doing a non-cuvette-load transfer and the turntable 11 can be stopped to discard any used cuvette.
2) When probe arm 17 is loading a cuvette within the turntable 11 and a cuvette can be inserted during the same time interval, assuming that the cuvette positioned at the insert point for cuvette delivery module 13 is spent.

The cuvette insertion logic that controls the cuvette delivery module 13, operating at a low priority, must therefore be opportunistic. Optimization of the process involves increasing the probability of occurrence of insertion opportunities. The system is programmed in an attempt to maximize the frequency of simultaneous loading and insertion of cuvettes.

If turntable 11 is free to be stopped anywhere, since the probe arm 17 is busy elsewhere, and more than one spent cuvette exists, the cuvette within turntable 11 selected for discard is the one for which the longest time exists to when it could be discarded with a concurrent load. This saves the cuvettes 10 that can be discarded with an upcoming concurrent load to take advantage of such opportunities.

When starting to load fluids into a clean cuvette 10 while there is more than one clean cuvette available within the turntable 11, the system selects an awaiting cuvette 10 that permits simultaneous insertion of a new cuvette within the turntable. If more than one such cuvette exists, one is selected subject to the following priorities. First priority is to pick a cuvette in a pseudo random manner to stop the wheel in successive positions that facilitate even heating of the wheel. Second priority is to load the oldest cuvette first to minimize the potential of contaminants (dust) accumulating in the cuvette over a period of time.

Sample Lifetime Monitoring

The components of the instrument CPU board track the useful lifetime of samples contained in the cups 35 and wells 36 of the ring segments 26. This prevents usage of a sample after it has suffered excessive evaporation. Samples include patient and quality control samples, calibrators, and curve correctors.

The expiration time for the material in a sample cup 35 or well 36 is determined at the time that each sample is first introduced to the chemistry instrument 24. Introduction can take the form of cup introduction, segment introduction, or receipt of a sample aliquot.

When a sample is diluted within a sample ring well, the recorded expiration time of the diluted liquid in the well 36 being maintained by the chemistry instrument 24 will be identical to that of the undiluted sample. This is based on the assumption that the rate of evaporation of diluted and undiluted samples is the same. At the time a dilution is performed, the diluted liquid in a well 36 is assumed to inherit the accumulated error in concentration due to evaporation in the undiluted sample. After dilution, the liquid in the diluted well 36 will be concentrated by the same percentage per unit time as is the undiluted sample from which it was produced.

After expiration of a sample, the chemistry instrument 24 will no longer use it. If it is subsequently needed for any of the instrument's workload, the operator will be nodified of the sample expiration by an appropriate message displayed on monitor 31.

Reagent Monitoring

Overview

The purpose of reagent monitoring is to warn the operator that a reagent within a particular bottle 25 has been in use over too long a period. Where two chemistry instruments 24 are used in tandem with a common workstation 30, each instrument tracks the age and volume of one working bottle for each reagent defined in its data base. The age of the working bottle is maintained in the memory of the instrument 24 even when it is removed from it for overnight storage of other purposes.

This description pertains to the manner by which the chemistry instrument 24 manages the sample/reagent tray 15. It describes the way in which the working bottles 25 of reagent and the working lifetimes of their reagent contents are tracked, how the instrument decides when a new bottle is to be used, and how reagent lot number changes are handled. It describes how the system reacts when the tray access cover 8 is opened. It further describes the activities of the system when a reagent bottle 25 is found to contain less reagent than is required for a requisitioned assay.

The chemistry instrument 24 shown in the drawings includes a sample/reagent tray 15 having room for forty reagent bottles 25. As one example, these might be twenty large (30 ml) bottles and twenty small (12 ml) ones. The tray 15 can be accessed by manually opening the hinged tray access cover 8. Cover 8 is provided with a sensor so that the controller system will be provided with a signal indicating whenever the reagent bottles 25 might have been disturbed.

Sample/reagent tray controller 312 will operate the motor 16 and the electronics associated with optical scanner ports 250 to read the labels at the bottom of every reagent bottle 25 at the conclusion of any operation requiring tray access cover 8 to have been opened. This information is used by the software to update stored data pertaining to their reagent identifications, lot codes, and serial numbers.

The volume in each reagent bottle 25 accessed by pipette 18 is measured each time that the instrument uses a reagent. This is done by using the pipette's fluid sensing capability to detect the elevation of liquid, which is then related to the interior volume of the bottle by using stored information relating to the bottle size.

The logic system associated with sample/reagent tray 15 supports a mode of operation wherein two bottles 25 of each reagent can be on the tray 15 at any given time. When the working bottle 25 is emptied, the instrument 24 will then start loading from the reserve bottle.

Any secondary or non-working bottles of reagents are also timed while in the tray 15. However, since they are not in use, their respective liquid volumes are not tracked. They are tracked by their positions within tray 15 only. Their age is not maintained in the instrument's memory if they are removed. It is possible to remove the tray 15 after the instrument 24 has been turned off and subsequently replace it before powering up the instrument 24 again. In this case, all of the bottles' ages will be maintained in memory.

Once introduced into the chemistry instrument 24, the contents of a primary reagent bottle 25 will continue to be used by it until the bottle is empty or is removed by an operator. When a bottle 25 containing reagent is first introduced into the chemistry instrument 24 in the tray 15, the controlling logic will assume it to be freshly reconstituted. A working expiration time will be established for it at such introduction. The number of hours remaining before expiration is available for display as needed on the monitor 31. If a reagent bottle 25 remains in the system beyond this time, the operator will be warned by an appropriate display message and the contents of the bottle will be "marked" as being expired on a status screen.

Reagent Definition Data Base

A reagent definition data base resides in disk memory provided with workstation 30 in the form of a shared data file (information common to two chemistry instruments 24) and one or more instrument-specific data files.

The shared data file defines the characteristics of each reagent. This includes the name, bottle identification, fluid type and working lifetime. The data pertaining to working lifetime is set up by the operator. The working lifetime is defined as the length of time during which the reagent within a bottle 25 is considered functionally usable from the time a new bottle is opened or reconstituted. The bottle identification is a number encoded into a machine-readable bottle label. The identification data captured by the bottle label scanning equipment also encodes the size and shape of the bottles. Ranges of identification values are reserved for particular bottle types. Captured information pertaining to fluid type is used by the operator interface in workstation 30 to generate appropriate choice lists.

The instrument-specific data base stores the status of each working reagent bottle 25, including working lot number, serial number, expiration time and volume. This data is stored in a non-volatile fashion so as to maintain data concerning each working reagent bottle even when it has been removed from the system or during periods when power has been lost. The volume remaining in each working reagent bottle is updated each time the bottle is used.

Sample/Reagent Tray Status Data

Each instrument CPU board 306 maintains the data pertaining to the status of the bottles 25 in each tray position in non-volatile random access memory. For each position in the tray, the system stores the type of reagent as well as its lot code and serial number, plus the volume, working expiration time and status of the container in question. A special software flag is set when the tray access cover 8 is opened or after power interruption, and cleared when the label on each bottle 25 within tray 15 is subsequently read by the scanning devices under optical scanner ports 250. When it is set, the prior data concerning the bottles is not totally invalid, since it represents the state of the bottle before the event.

Data is maintained in the instrument 24 as to whether or not each reagent is required by waiting, on-hold and active instrument workload. This is maintained by a background status update task in the instrument CPU board 306, so that it is continually updated. This data is used by the reagent status screen to show which reagents are required by the workload. This can also be used by an operator to do requirements checking through workstation 30 to warn for insufficient reagent.

Fluid Transfers From Reagent Bottles

Fluid transfers involving reagent bottles 25 are always done from working or primary bottles of a reagent. The working bottle is recognized by its label information. The system supports having multiple bottles of each reagent, one designated by the instrument as a working bottle and the others as reserve bottles. When the working bottle becomes empty a reserve bottle becomes the new working bottle.

Proper operation of the chemistry instrument 24 does not permit liquid to be added to a working bottle. A bottle will be rejected if its liquid volume has increased above a specified minimum amount since it was last accessed by probe 18. It is assumed that an operator might open the cover, pour some of the working reagent from a particular reagent bottle 25, and then return the reagent bottle to sample/reagent tray 15. Such activity can be accommodated by the controlling software, since it is presumed that removal of liquid from a reagent bottle 25 will not contaminate its content, whereas addition of liquid to it will.

Every time a liquid transfer is to be made from a bottle 25, the working bottle must be identified or selected from a set of reserve bottles. When the transfer is started, the liquid transfer module controller 310 is provided with data containing limits within which the volume in the appropriate working bottle should be found. If controller 310 finds the volume within the identified reagent bottle 25 to be short or outside the limits, it aborts the transfer, discards any received liquid in the pipette 18 and communicates data relating to the measured volume to the instrument CPU board 306.

If no working bottle for a needed reagent can be identified by the software, a new working bottle must be selected. The reserve bottles of reagent are each marked in memory with a time of appearance on the tray 15. The oldest reserve bottle then becomes the next working bottle. If more than one reserve bottle is marked in memory with the same time of appearance, the one with the lowest numbered tray position will be arbitrarily selected.

The above rules are only followed for the lot number currently in use. If more than one lot of reagent is present, the working reagent bottle 25 will be chosen from the bottles of the working lot number. All bottles of other lots are considered reserve bottles.

The capacitive sensing system for detecting fluid levels within the instrument 24 is utilized to capture reagent volume information for each working bottle of reagent on a real-time basis during all operations. As pipette 18 is lowered into a reagent bottle 25, it is stopped by operation of the transfer module controller 310 when the liquid surface within the bottle is sensed. The controller 310 has data relating to the bottle identification, which implies the bottle's diameter and dead volume. The volume of reagent within the bottle 25 is then deduced by the controller 310 from the height of the pipette tip.

Each time a reagent bottle 25 is probed by pipette 18, the stored data relating to the volume of reagent remaining within it is verified and updated, if necessary. The controller 310 communicates data with respect to the volume of reagent in the reagent bottle 25 back to the instrument CPU board in microliters, excluding the dead volume. If a transfer was performed from the reagent bottle 25, the reported volume is corrected for the volume of reagent removed.

The instrument CPU board 306 is also programmed to respond to unexpected volumes of reagent measured by the probing action of pipette 18. When a fluid transfer from a reagent bottle 25 is performed, the liquid transfer module controller calculates the high and low limits to the acceptable volume that should be within the selected bottle. The software allows for a predetermined volume measurement error tolerance. If the tray access cover 8 has not been opened since the last time that the selected bottle 25 was probed, the volume of reagent within it should not deviate from the last-measured volume by more than the tolerance in either direction. If it does, this is reported as a warning to the operator. The operator's normal course of action in this case is to go to diagnostics.

If the tray access cover 8 has been opened since the last time the selected working reagent bottle 25 was probed, the instrument 24 will expect the volume of reagent within each reagent bottle 25 to be between the last volume (plus tolerance) and zero. If the measured volume of reagent within a probed bottle 25 is found to be too great, use of the bottle is not allowed. This guards against use of bottle contents that might have been accidently or purposefully contaminated or diluted during their use in the instrument.

The instrument 24 is programmed to respond to data indicating that the volume of reagent in a working bottle is short of that required for a requisitioned assay or test. Each time that such a reagent bottle 25 is probed, the transfer module controller 310 will report that its liquid content is empty. This is reported to the operator by a message on monitor 31.

If a reagent bottle 25 is found short during a fluid transfer, the contents of the probe are discarded, and the run being loaded is canceled. If other reagent bottles 25 of this type are on the tray, a new working bottle is selected and the run is rescheduled. Otherwise, the run is put on hold.

When the instrument CPU board 306 is re-initialized, it assumes that power has been removed from the chemistry instrument 24. Since the tray access cover 8 might have been opened while power was removed, the system behaves as if the cover 8 has been opened. The instrument CPU board 306 is capable of continuing to monitor the sensors that detect opening of cover 8 while carrying out diagnostic procedures, so the tray 15 is only scanned as necessary after diagnostics.

Every time the cover 8 has been opened, each reagent bottle 25 is marked in the controlling software as requiring reading of its label. This causes the bottle label to be read. When the cover 8 is again closed, the system scans the sample/reagent tray 15 to read all the bottle labels. The system remembers the tray status in memory until the new status is figured out completely. Thus, if the system is reset during a scan, the previous data is not lost. If power is lost while a new status is being written, the system starts a new scan.

When a reagent bottle 25 is recognized as a new working bottle, the working bottle expiration time is updated in the reagent data base. If a test uses an external reagent blank, a new blank value is stored when a new bottle is started for any reagent involved in the test's load sequence. The scheduling software within the instrument CPU board 306 will then load an external reagent blank cuvette for the first run of turntable 11 scheduled using the new reagent bottle 25.

If a patient or quality control test run is being loaded onto the turntable 11 and an external reagent blank has been loaded from a working reagent bottle, but a new bottle is started before the reaction cuvette for the test has been loaded, the test run must be rescheduled by the controlling software. Both the external reagent blank and the reaction cuvette must be loaded using reagent from the same reagent bottle 25.

Bottles 25 containing reagent of a lot other than the working lot are ignored until the system has no choice but to pick a new working reagent from them. A new working reagent is then selected from them by using the oldest appearance time or the lowest tray position, if the times are equal.

The system requires a test to be calibrated before running a patient or quality control test from a new lot. When a new working reagent must be selected, and all of the choices are from a new lot, the test is marked as requiring calibration. If a calibration request is waiting, a working bottle is selected and the calibration is scheduled.

This invention has been described in language more or less specific as to structural features. It is to be understood, however, that the invention is not limited to the specific features shown, since the means and construction herein disclosed comprise a preferred form of putting the invention into effect. The invention is, therefore, claimed in any of its forms or modifications within the proper scope of the appended claims appropriately interpreted to include appropriate equivalents.

We claim:

1. A method for operating a chemistry instrument, comprising:
    releasably mounting a plurality of individually disposable cuvettes, each having an upper end including an opening providing access to its interior for receipt of liquids, into equiangularly spaced radial compartments of a turntable that is rotatable about a first vertical axis;
    sequentially indexing the turntable to a stationary angular position about the first vertical axis with any randomly selected cuvette positioned at a cuvette access station or at a cuvette insertion station and then turning it about the first vertical axis while mixing or centrifuging the contents of cuvettes mounted to it;
    analyzing the contents of any randomly selected cuvettes mounted on the turntable as their contents are being centrifuged;
    indexing a tray containing a plurality of containers about a second vertical axis parallel to and spaced from the first vertical axis to a stationary angular position about the second vertical axis with any selected container positioned at a container access station;
    moving a pipette along an arcuate path centered about a third vertical axis that is parallel to the first vertical axis and intersects both the cuvette access station and the container access station to thereby selectively transfer liquids from any randomly accessed container positioned on the tray at the container access station to any randomly selected cuvette positioned on the turntable at the cuvette access station; and
    selectively inserting an individual cuvette into any randomly selected compartment of the turntable at the cuvette insertion station.

2. The method of claim 1 further comprising the following steps:
    puncturing an opening through a closure on a manually-delivered draw tube placed in a sample tube entry port; and
    subsequently inserting the pipette coaxially through the punctured opening in the closure to access the interior of the draw tube.

3. The method of claim 1 further comprising the following additional steps:
    receiving and coaxially orienting a manually placed draw tube beneath a puncture tube;
    moving the draw tube between a lowered position wherein the draw tube is clear of the puncture tube and a raised position wherein the puncture tube forms a temporary opening through a closure on the draw tube; and
    subsequently inserting the pipette coaxially through the opening in the closure to access the interior of the draw tube.

4. The method of claim 1 further comprising the following additional steps:
    receiving and coaxially orienting a manually placed draw tube beneath a puncture tube;
    moving the draw tube between a lowered position wherein the draw tube is clear of the puncture tube and a raised position wherein the puncture tube forms a temporary opening through a closure on the draw tube;
    subsequently inserting the pipette coaxially through the opening in the closure to access the interior of the draw tube; and
    detecting the level of liquid in the draw tube as it is approached by the pipette.

5. The method of claim 1 wherein the step of moving the pipette provides randomly accessible transfer of liquid from any randomly selected container on the tray to any randomly selected cuvette on the turntable.

6. The method of claim 1 further comprising the following step:
    cyclically transferring liquid from any randomly selected container on the tray to any randomly selected cuvette on the turntable, mixing liquids within the cuvettes on the turntable by turning it about the first vertical axis, and rotating the turntable about the first vertical axis.

7. The method of claim 1 wherein the step of turning the turntable comprises:
    mixing liquids within cuvettes located on the turntable by turning it about the first vertical axis, and subsequently centrifuging the liquids by rotating the turntable about the first vertical axis.

8. The method of claim 1 further comprising the following step:
    periodically monitoring the axial position of the pipette relative to a the remainder of the instrument.

9. The method of claim 1 further comprising the following step:
    periodically monitoring the radial position of the pipette relative to the third vertical axis.

10. The method of claim 1 wherein the analyzing step comprises:
    performing fluorescent tests on the contents of any randomly selected cuvette as the cuvettes are rotated by the turntable.

11. The method of claim 1 wherein the analyzing step comprises:
    performing absorbent tests on the contents of any randomly selected cuvette as the cuvettes are rotated by the turntable.

12. The method of claim 1 further comprising the following step:
  transferring liquids from any randomly selected container on the tray positioned at the container access station to a sample delivery station along the arcuate path of the pipette; and
  performing potentiometric tests on the liquid samples delivered to the sample delivery station.

13. The method of claim 1 further comprising the following step:
  capturing information from indicia on a container on the tray identifying the container contents and its working life.

14. The method of claim 1 further comprising the following step:
  maintaining a current record of the amount of liquid in containers on the tray.

15. The method of claim 1 further comprising the following step:
  recording the elapsed time that has occurred since introduction of each sample into the chemical analyzer.

16. The method of claim 1 further comprising the following step:
  detecting the level of liquid in a container on the tray by capacitive sensing as it is approached by the pipette.

17. A chemistry instrument, comprising:
  a turntable rotatably mounted about a first vertical axis, the turntable having a plurality of equiangularly spaced radial compartments;
  a plurality of individually disposable cuvettes releasably mounted within the compartments of the turntable, each cuvette having an upper end including an opening providing access to its interior for receipt of liquids;
  first power means operably connected to the turntable for alternately (1) indexing the turntable at a stationary angular position about the first vertical axis with any randomly selected cuvette positioned at a cuvette access station or (2) turning it about the first vertical axis while mixing or centrifuging the contents of cuvettes mounted within the compartments of the turntable;
  first analytical means adjacent to the turntable for performing optical tests on the contents of any randomly selected cuvettes;
  a tray rotatably mounted about a second vertical axis parallel to and spaced from the first axis;
  a plurality of containers positioned about the tray;
  second power means operably connected to the tray for indexing it to a stationary angular position about the second vertical axis with any randomly selected container positioned at a container access station;
  probe arm means movable about a third vertical axis parallel to and spaced from the first vertical axis, the probe arm means including a downwardly-extending open pipette movable along an arcuate path centered about the third vertical axis and intersecting the cuvette access station and container access station for transferring liquid from any randomly accessed container positioned on the tray at the container access station to any randomly selected cuvette positioned on the turntable at the cuvette access station; and
  cuvette delivery means adjacent to the turntable for selectively inserting an individual cuvette into any randomly selected compartment of the turntable.

18. The chemistry instrument of claim 17, further comprising:
  control means operably connected to the turntable for first mixing liquids within cuvettes located on the turntable by reversibly turning the turntable about the first vertical axis, and then centrifuging the liquids by rotating the turntable in a selected angular direction about the first vertical axis in a repetitive sequence of turntable operation.

19. The chemistry instrument of claim 17, wherein the first power means is operably connected to the turntable for locating any randomly selected compartment on the turntable at a cuvette insertion station while locating a cuvette at the cuvette access station;
  the cuvette delivery means further comprising:
    a magazine adapted to contain a plurality of cuvettes; and
    ram means for selectively moving a cuvette from the magazine to a compartment on the turntable located at the cuvette insertion station.

20. The chemistry instrument of claim 17, wherein the first power means is operably connected to the turntable for locating any randomly selected compartment on the turntable at a cuvette insertion station while locating a cuvette at the cuvette access station;
  the cuvette delivery means further comprising:
    a magazine adapted to contain a plurality of cuvette stacks, in which at least one stack includes cuvettes each containing a predetermined quantity of a reagent; and
    ram means for selectively moving a cuvette from the magazine to a compartment on the turntable located at the cuvette insertion station.

21. The chemistry instrument of claim 17, further comprising:
  probe detection means positioned at an alignment station along the arcuate path of the pipette for monitoring the axial position of the pipette relative to the third vertical axis of the probe arm means.

22. The chemistry instrument of claim 17, wherein the first analytical means performs fluorescent tests on the contents of any randomly selected cuvettes as they are turned about the first vertical axis while on the turntable.

23. The chemistry instrument of claim 17, wherein the first analytical means performs absorbent tests on the contents of any randomly selected cuvettes as they are turned about the first vertical axis while on the turntable.

24. The chemistry instrument of claim 17, further comprising:
  second analytical means located at a sample delivery station along the arcuate path of the pipette for performing potentiometric tests on liquid samples delivered to it by the pipette.

25. The chemistry instrument of claim of 17, further comprising:
  scanning means adjacent to the tray for capturing information from encoded indicia on a container positioned on the tray.

26. The chemistry instrument of claim 17, further comprising:
  monitoring means for maintaining a current record of the amount of liquid in containers on the tray.

27. The chemistry instrument of claim 17, wherein the containers comprise individually removable reagent bottles, individually removable sample cups positioned within ring segments attachable to the tray, and a plurality of open liquid wells integrally formed within ring segments attachable to the tray.

28. The chemistry instrument of claim 17, wherein the containers comprise individually removable reagent bottles, individually removable sample cups positioned within ring segments attachable to the tray, and a plurality of open liquid wells integrally formed within ring segments attachable to the tray; and
the probe arm means being operable for transferring liquids from one randomly selected well to a second randomly selected well.

29. The chemistry instrument of claim 17, wherein the containers comprise individually removable reagent bottles, individually removable sample cups positioned within ring segments attachable to the tray, and a plurality of open liquid wells integrally formed within ring segments attachable to the tray;
the probe arm means being operable for transferring liquids from any randomly selected cup to any randomly selected well.

30. The chemistry instrument of claim 17, wherein the containers comprise individually removable reagent bottles, individually removable sample cups positioned within ring segments attachable to the tray, and a plurality of open liquid wells integrally formed within ring segments attachable to the tray;
the probe arm means being operable for transferring liquids from any randomly selected reagent bottle to any randomly selected well.

31. The chemistry instrument of claim 17, wherein the containers comprise individually removable reagent bottles, individually removable sample cups positioned within ring segments attachable to the tray, and a plurality of open liquid wells integrally formed within ring segments attachable to the tray;
the probe arm means being operable for transferring liquids from any randomly selected reagent bottle to any randomly selected cuvette on the turntable.

32. The chemistry instrument of claim 17, wherein the containers comprise individually removable reagent bottles, individually removable sample cups and a plurality of open liquid wells integrally formed within ring segments attachable to the tray; and
monitoring means for maintaining a current record of the amount of liquid in each of the containers.

33. The chemistry instrument of claim 17, further comprising:
capacitive sensing means operably connected to the pipette and to a conductive member located adjacent to the tray for detecting the level of liquid in a container on the tray as it is approached by the pipette.

34. The chemistry instrument of claim 17, further comprising:
capacitive sensing means operably connected to the pipette and to a conductive member located adjacent to the tray for detecting the level of liquid in a well on the tray as it is approached by the pipette.

35. An automated chemistry analyzer system including first and second chemistry instruments, each chemistry instrument comprising:
a turntable rotatably mounted about a first vertical axis, the turntable having a plurality of equiangularly spaced radial compartments;
a plurality of individually disposable cuvettes releasably mounted within the compartments of the turntable, each cuvette having an upper end including an opening providing access to its interior for receipt of liquids;
first power means operably connected to the turntable for alternately (1) indexing the turntable at a stationary angular position about the first vertical axis with any randomly selected cuvette positioned at a cuvette access station or (2) turning it about the first vertical axis while mixing or centrifuging the contents of cuvettes mounted within the compartments of the turntable;
first analytical means adjacent to the turntable for performing optical tests on the contents of any randomly selected cuvettes;
a tray rotatably mounted about a second vertical axis parallel to and spaced from the first axis;
a plurality of containers positioned about the tray;
second power means operably connected to the tray for indexing it to a stationary angular position about the second vertical axis with any randomly selected container positioned at a container access station;
probe arm means movable about a third vertical axis parallel to and spaced from the first vertical axis, the probe arm means including a downwardly-extending open pipette movable along an arcuate path centered about the third vertical axis and intersecting the cuvette access station and container access station for selectively transferring liquids from randomly accessed containers positioned on the tray at the container access stations to any randomly selected cuvette positioned on the turntable at the cuvette access station;
cuvette delivery means adjacent to the turntable for selectively inserting an individual cuvette into any randomly selected compartment of the turntable; and
common controller means operably connected to both chemistry instruments.

36. The system of claim 35, wherein each chemistry instrument further comprises:
sample tube entry port means for supporting an individual draw tube after it has been manually delivered to a sample access station;
the common controller means being programmed to aliquot sufficient sample from a draw tube at each sample tube entry port means of the first and second chemistry instruments to carry out the tests that can be run by the respective chemistry instruments, as identified by reagents available on their trays and relevant calibration data, plus enough additional volume of sample to run tests for which neither chemistry instrument has requirements.

37. A chemistry instrument, comprising:
a turntable rotatably mounted about a first vertical axis, the turntable having a plurality of equiangularly spaced radial compartments;
a plurality of individually disposable cuvettes releasably mounted within the compartments of the turntable, each cuvette having an upper end including an opening providing access to its interior for receipt of liquids;
first power means operably connected to the turntable for alternately (1) indexing the turntable at a stationary angular position about the first vertical axis with any randomly selected cuvette positioned at a cuvette access station or (2) turning it about the first vertical axis while mixing or centrifuging the contents of cuvettes mounted within the compartments of the turntable;

first analytical means adjacent to the turntable for performing optical tests on the contents of any randomly selected cuvettes;

a tray rotatably mounted about a second vertical axis parallel to and spaced from the first axis;

a plurality of containers positioned about the tray;

second power means operably connected to the tray for indexing it to a stationary angular position about the second vertical axis with any randomly selected containers positioned at first and second container access stations;

probe arm means movable about a third vertical axis parallel to and spaced from the first vertical axis, the probe arm means including a downwardly-extending open pipette movable along an arcuate path centered about the third vertical axis and intersecting the cuvette access and container access station for transferring liquids from any randomly accessed container positioned on the tray at the first or second container access stations to any randomly selected cuvette positioned on the turntable at the cuvette access station; and cuvette delivery means adjacent to the turntable for selectively inserting an individual cuvette into any randomly selected compartment of the turntable.

38. The chemistry instrument of claim 37, wherein the probe arm means transfers liquids from a randomly selected container positioned on the tray at the first container access station to a randomly selected container positioned on the tray at the second container access station.

39. The chemistry instrument of claim 37, wherein the probe arm means transfers liquids from a first randomly selected container positioned on the tray at the second container access station to a second randomly selected container on the tray subsequently positioned on the tray at the second container access station.

40. A chemistry instrument, comprising:
a turntable rotatably mounted about a first vertical axis, the turntable having a plurality of equiangularly spaced radial compartments;

a plurality of individually disposable cuvettes releasably mounted within the compartments of the turntable, each cuvette having an upper end including an opening providing access to its interior for receipt of liquids;

first power means operably connected to the turntable for alternately (1) indexing the turntable at a stationary angular position about the first vertical axis with any randomly selected cuvette positioned at a cuvette access station or (2) turning it about the first vertical axis while mixing or centrifuging the contents of cuvettes mounted within the compartments of the turntable;

first analytical means adjacent to the turntable for performing optical tests on the contents of any randomly selected cuvettes;

a tray rotatably mounted about a second vertical axis parallel to and spaced from the first axis;

a plurality of containers positioned about the tray;

second power means operably connected to the tray for indexing it to a stationary angular position about the second vertical axis with randomly selected containers positioned at first and second container access stations;

sample tube entry port means for supporting an individual draw tube after it has been manually delivered to a sample access station;

probe arm means movable about a third vertical axis parallel to the first vertical axis, the probe arm means including a downwardly-extending open pipette movable along an arcuate path centered about the third vertical axis and intersecting the cuvette access station, container access stations, and sample access station for transferring liquids from a draw tube in the sample tube entry port positioned at the sample access station to any randomly selected container positioned on the tray at the first container access station or from any randomly accessed container positioned on the tray at the second container access station to any randomly selected cuvette positioned on the turntable at the cuvette access station; and cuvette delivery means adjacent to the turntable for selectively inserting an individual cuvette into any randomly selected compartment of the turntable.

41. The chemistry instrument of claim 40, wherein the sample tube entry port means further comprises:
puncturing means for temporarily forming an opening through a closure on a manually-delivered draw tube placed in the sample tube entry port means, the interior of the draw tube being accessible by subsequently inserting the pipette of the probe arm means coaxially through the puncturing means.

42. The chemistry instrument of claim 40, wherein the sample tube entry port means further comprises:
a stationary puncture tube centered along a fourth vertical axis parallel to the first vertical axis; and draw tube ram means positioned below the puncture tube for receiving and coaxially orienting a manually placed draw tube relative to the puncture tube and for moving the draw tube parallel to the fourth vertical axis between a lowered position wherein the draw tube is clear of the puncture tube and a raised position wherein the puncture tube forms a temporary opening through a draw tube closure for subsequent coaxial insertion of the pipette.

43. The chemistry instrument of claim 40, wherein the sample tube entry port means further comprises:
a stationary puncture tube centered along a fourth vertical axis parallel to the first vertical axis; and draw tube ram means positioned below the puncture tube for receiving and coaxially orienting a manually placed draw tube relative to the puncture tube and for moving the draw tube parallel to the fourth vertical axis between a lowered position wherein the draw tube is clear of the puncture tube and a raised position wherein the puncture tube forms a temporary opening through a draw tube closure for subsequent coaxial insertion of the pipette; and capacitive sensing means operably connected to the pipette and to a conductive member located adjacent to the draw tube ram means for detecting the level of liquid in a draw tube as it is approached by the pipette.

* * * * *